US008722877B2

(12) United States Patent
Chesworth et al.

(10) Patent No.: US 8,722,877 B2
(45) Date of Patent: *May 13, 2014

(54) 7-DEAZAPURINE MODULATORS OF HISTONE METHYLTRANSFERASE, AND METHODS OF USE THEREOF

(71) Applicant: Epizyme, Inc., Cambridge, MA (US)

(72) Inventors: Richard Chesworth, Concord, MA (US); Kevin Wayne Kuntz, Woburn, MA (US); Edward James Olhava, Newton, MA (US); Michael A. Patane, Andover, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/018,171

(22) Filed: Sep. 4, 2013

(65) Prior Publication Data
US 2014/0073597 A1     Mar. 13, 2014

Related U.S. Application Data

(63) Continuation of application No. 13/991,328, filed as application No. PCT/US2011/063314 on Dec. 5, 2011.

(60) Provisional application No. 61/419,504, filed on Dec. 3, 2010.

(51) Int. Cl.
*A01N 43/04*     (2006.01)
*A61K 31/70*     (2006.01)
*C07H 19/22*     (2006.01)

(52) U.S. Cl.
USPC ........................................ 536/27.14; 514/43

(58) Field of Classification Search
None
See application file for complete search history.

(56) References Cited

U.S. PATENT DOCUMENTS

| | | | |
|---|---|---|---|
| 4,794,174 A * | 12/1988 | Secrist, III | 536/27.3 |
| 7,576,069 B2 | 8/2009 | Rieger et al. | |
| 2004/0147464 A1 | 7/2004 | Roberts et al. | |
| 2006/0040889 A1 | 2/2006 | Rieger et al. | |
| 2006/0189636 A1 | 8/2006 | Critchley et al. | |
| 2006/0235037 A1 | 10/2006 | Purandare et al. | |
| 2007/0191293 A1 | 8/2007 | Langston et al. | |
| 2008/0064653 A1 | 3/2008 | Li et al. | |
| 2008/0132525 A1 | 6/2008 | Wahhab et al. | |
| 2009/0105476 A1 | 4/2009 | Fairhurst et al. | |
| 2010/0144655 A1 | 6/2010 | Chen et al. | |

FOREIGN PATENT DOCUMENTS

| | | |
|---|---|---|
| EP | 1138688 A1 | 10/2001 |
| EP | 2208721 A1 | 7/2010 |
| WO | WO-0172764 A1 | 10/2001 |
| WO | WO-0177075 A2 | 10/2001 |
| WO | WO-02100152 A2 | 12/2002 |
| WO | WO-03074083 A1 | 9/2003 |
| WO | WO-2004007512 A2 | 1/2004 |
| WO | WO-2004022572 A1 | 3/2004 |
| WO | WO-2006015357 A2 | 2/2006 |
| WO | WO-2006078752 A2 | 7/2006 |
| WO | WO-2006113615 A2 | 10/2006 |
| WO | WO-2007100304 A1 | 9/2007 |
| WO | WO-2008124150 A1 | 10/2008 |
| WO | WO-2009089425 A1 | 7/2009 |
| WO | WO-2010027005 A1 | 3/2010 |
| WO | WO-2010048149 A2 | 4/2010 |
| WO | WO-2012075381 A2 | 6/2012 |
| WO | WO-2012075492 A2 | 6/2012 |
| WO | WO-2012082436 A2 | 6/2012 |

OTHER PUBLICATIONS

Haynes et al. Journal of Pharmaceutical Sciences, vol. 94, No. 10, Oct. 2005.*
Daigle et al. "Selective Killing of Mixed Lineage Leukemia Cells by a Potent Small-Molecule DOT1L Inhibitor." *Cancer Cell.* 20(2011):53-65.
Deng et al. "Synthesis, Activity and Metabolic Stability of Non-Ribose Containing Inhibitors of Histone Methyltransferase DOT1L." *Med. Chem. Commun.* 4(2013):822-826.
Min et al. "Structure of the Catalytic Domain of Human DOT1L, a Non-SET Domain Nucleosomal Histone Methyltransferase." *Cell.* 112(2003):711-723.

* cited by examiner

*Primary Examiner* — Layla Bland
(74) *Attorney, Agent, or Firm* — Mintz Levin Cohn Ferris Glovsky and Popeo, P.C.; Heidi A. Erlacher; Lian Ouyang

(57) ABSTRACT

Disclosed are compounds, pharmaceutical compositions containing the compounds, uses of the compounds and compositions as modulators of histone methyltransferases, and methods for treating diseases influenced by modulation of histone methyltransferase activity.

12 Claims, 8 Drawing Sheets

Figure 5

*Inhibition of human histone methyltransferases (HMTs) by 16.*

| Enzyme | IC$_{50}$ (nM) [a] | Fold-selectivity [b] |
|---|---|---|
| DOT1L | 0.4 ± 0.1 | 1.0 |
| CARM1 | > 50,000 | > 100,000 |
| EHMT2 | > 50,000 | > 100,000 |
| EZH1 [c] | > 50,000 | > 100,000 |
| EZH2 [c] | > 50,000 | > 100,000 |
| PRMT1 | > 50,000 | > 100,000 |
| PRMT5 | 512 ± 85 | 1,280 |
| PRMT8 | > 50,000 | > 100,000 |
| SETD7 | > 50,000 | > 100,000 |
| WHSC1 | > 50,000 | > 100,000 |

[a] IC$_{50}$ is the concentration of compound resulting in 50% inhibition of enzyme activity.
[b] Fold-selectivity is relative to DOT1L, and is calculated as the ratio of the IC$_{50}$ for the enzyme under study over the IC$_{50}$ for DOT1L.
[c] Measured in the context of the PRC2 multi-protein complex.

Figure 6

*Concentration-dependent inhibition of cell proliferation by 16 in various cell types.*

| MLL-gene fusion | Cell type | IC50 (µM)[a] | 95% Confidence Interval for IC50 (µM) |
|---|---|---|---|
| MLL-AF4 | RS4;11 | 6.47 | 4.22 to 9.94 |
| MLL-AF4 | SEM | 1.72 | 1.21 to 2.46 |
| MLL-AF4 | MV4-11 | 0.17 | 0.15 to .19 |
| MLL-AF9 | THP-1 | 3.36 | 2.51 to 3.80 |
| MLL-AF9 | MOLM-13 | 0.72 | 0.65 to 0.80 |
| MLL-ENL | KOPN-8 | 0.62 | 0.49 to 0.79 |
| Non-rearranged | REH | 13.90 | 8.25 to 23.46 |
| Non-rearranged | Kasumi-1 | 32.99 | 30.03 to 36.24 |
| Non-rearranged | 697 | 36.57 | 34.77 to 38.46 |
| Non-rearranged | HL-60 | >50 | NA |
| Non-rearranged | Jurkat | >50 | NA |
| Non-rearranged | U937 | >50 | NA |

[a] $IC_{50}$ is the concentration of compound that results in a half-maximal degree of inhibition.

7-DEAZAPURINE MODULATORS OF HISTONE METHYLTRANSFERASE, AND METHODS OF USE THEREOF

CROSS-REFERENCE TO RELATED APPLICATIONS

This application is a continuation of U.S. patent application Ser. No. 13/991,328, which is a national stage application, filed under 35 U.S.C. §371, of International Application No. PCT/US2011/063314, filed Dec. 5, 2011, which claims priority to, and the benefit of, U.S. provisional application No. 61/419,504, filed Dec. 3, 2010, the contents of each of which are incorporated herein by reference in their entireties.

BACKGROUND OF THE INVENTION

In eukaryotic cells DNA is packaged with histones to form chromatin. Approximately 150 base pairs of DNA are wrapped twice around an octamer of histones (two each of histones 2A, 2B, 3 and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes such as differentiation, proliferation and apoptosis. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of a methyl group at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide temporal control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion Rearrangements of the mixed lineage leukemia (MLL) gene on chromosome 11q23 are associated with aggressive leukemias with a poor prognosis. MLL translocations result in aberrant recruitment of DOT1L, a histone methyltransferase that methylates lysine 79 of histone H3 (H3K79), to chromatin leading to ectopic H3K79 methylation and increased expression of genes involved in leukemogenesis. These rearrangements, which are found in over 70% of infant leukemias and approximately 10% of adult acute myeloid leukemias (AML), result in the expression of fusion proteins in which the C-terminal sequences of MLL, including a SET-domain that methylates lysine 4 of histone H3 (H3K4), are replaced with sequences derived from a variety of fusion partners, including AF4, AF9, and ENL. The majority of these fusion partners are components of transcriptional elongation complexes that, directly or indirectly, recruit DOT1L to genomic loci bound by the MLL-fusion protein. This results in elevated H3K79 methylation and increased mRNA expression of MLL-fusion target genes, such as HOXA9 and MEIS1 that are central to the pathogenesis of leukemia.

Mistargeted DOT1L enzymatic activity has therefore been proposed as a driver of disease in MLL patients, however in the absence of specific DOT1L methyltransferase inhibitors, this hypothesis has not been directly addressed in model systems.

Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes holds great promise for the treatment of a range of diseases.

SUMMARY OF THE INVENTION

One aspect of the present invention relates to compounds that selectively modulate the activity of the histone methyltransferase DOT1L. For example, one aspect of the invention relates to a compound of formula I:

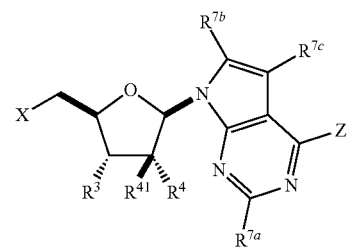

or a pharmaceutically acceptable salt, hydrate, enantiomer or stereoisomer thereof, wherein independently for each occurrence,

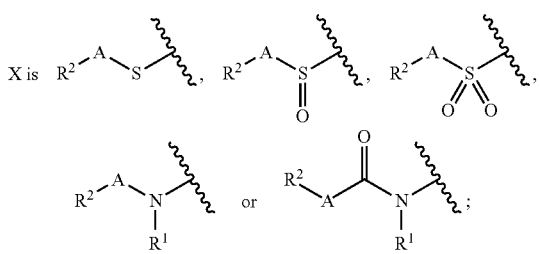

$R^1$ is hydrogen, alkyl, cycloalkyl, alkylcycloalkyl, alkylaryl, haloalkyl, formyl, heterocyclyl, heterocyclylalkyl,

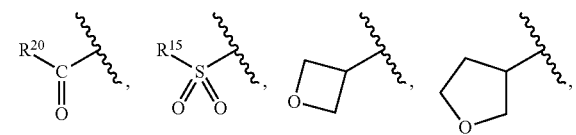

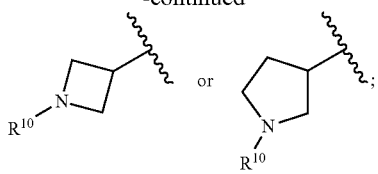 or or $(C_2-C_4)$alkyl substituted with

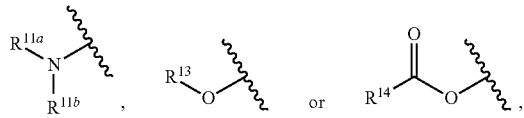

except that when X is

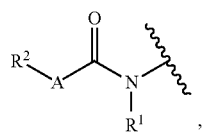

$R^1$ is not

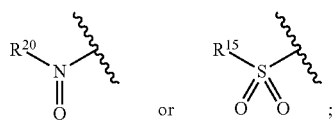

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl or silyl;
$R^{14}$ is hydrogen, alkyl, aryl, heteroaryl, aralkyl or heteroaralkyl;
$R^{15}$ is alkyl, cycloalkyl or cycloalkylalkyl;
$R^{20}$ is hydrogen, alkyl, cycloalkyl or cycloalkylalkyl;

A is 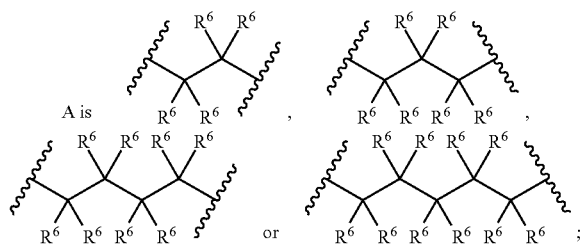

$R^2$ is 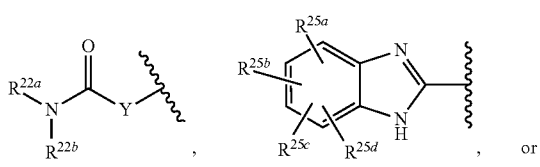

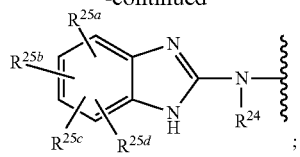

Y is —NH—, —N(alkyl)-, —O—, or —$CR^6_2$—;
$R^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;
$R^{22b}$ is hydrogen or alkyl;
$R^{24}$ is hydrogen or alkyl;
$R^{25a}$, $R^{25b}$, $R^{25c}$, and $R^{25d}$ independently are -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
$R^3$ is hydrogen, halogen, hydroxy, alkyloxy, aralkyloxy, alkylcarbonyloxy or silyloxy;
$R^4$ is hydrogen, halogen, hydroxy, alkyloxy, aralkyloxy, alkylcarbonyloxy or silyloxy;
$R^{41}$ is hydrogen, alkyl or alkynyl;
Z is hydrogen or

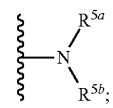

$R^{5a}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl:
$R^{5b}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with $R^{5a}$ and the nitrogen to which it is attached forms a 4- to 8-membered heterocyclyl comprising 0 or 1 additional heteroatoms;
$R^6$ is hydrogen, alkyl or halo; or two geminal $R^6$ taken together are ethylene, propylene or butylene;

$R^{7a}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo;

$R^{7b}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo; and $R^{7c}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo.

Another aspect of the invention relates to a pharmaceutical composition comprising an compound of the invention (e.g., a compound of formula I, or a pharmaceutically acceptable salt, hydrate, enantiomer or stereoisomer thereof), and one or more pharmaceutically acceptable carriers. A pharmaceutical composition of the invention may also comprise a second therapeutic agent. Such pharmaceutical compositions of the invention can be administered in accordance with a method of the invention (for example, as part of a therapeutic regimen for treatment or prevention of conditions and disorders related to cancer and/or neurodegenerative disorders). In one embodiment, the invention relates to a packaged pharmaceutical comprising a therapeutically effective amount of the compound or composition. In one embodiment, the invention relates to a packaged pharmaceutical comprising a prophylactically effective amount of the compound or composition.

Another aspect of the invention relates to a method of treating or preventing a disorder in which DOT1-mediated protein methylation plays a part, comprising administering to a subject in need thereof a therapeutically effective amount of a compound of the present invention. Such methods can be used to ameliorate any condition which is caused by or potentiated by the activity of DOT1.

Another aspect of the invention relates to a method of inhibiting or reducing the level of DOT1L activity in a cell comprising the step of contacting a cell with or providing to a subject a compound of the present invention.

Another aspect of the invention relates to a method of inhibiting or reducing the level of histone H3 lysine residue 79 (H3K79) methylation in a cell comprising the step of contacting a cell with or providing to a subject a compound of the present invention. Such methods can be used to ameliorate any condition which is caused by or potentiated by the activity of DOT1 through H3K79 methylation.

Another aspect of the invention relates to a method of treating or preventing specific disorders in which DOT1 methylation plays a part, for example, in cancer or a neurological disorder. Such methods comprise the step of administering to a subject in need thereof a therapeutically effective amount of a compound or pharmaceutical composition of the invention.

BRIEF DESCRIPTION OF THE FIGURES

FIG. 5 tabulates inhibition ($IC_{50}$ values) of human histone methyltransferases (HMTs) by compound 16.

FIG. 6 tabulates concentration-dependent inhibition of cell proliferation by compound 16 in various cell types.

DETAILED DESCRIPTION

Underlying Molecular Biology

Figure 1:
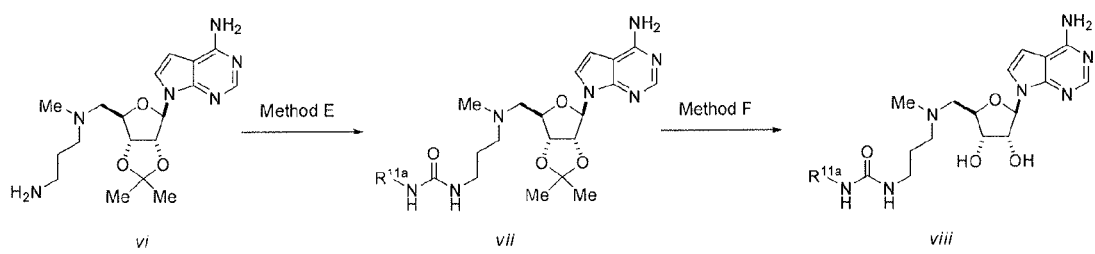
FIG. 1 depicts general routes for preparing compounds of the invention.

Chromatin structure is important in gene regulation and epigenetic inheritance. Post-translational modifications of histones are involved in the establishment and maintenance of higher-order chromatin structure; for example, the tails of certain core histones are modified by acetylation, methylation, phosphorylation, ribosylation and ubiquitination.

One aspect of the present invention relates to compounds that selectively modulate the activity of the histone methyltransferase DOT1L, an enzyme known to methylate lysine 79 of histone H3 ("H3K79") in vivo (Feng et al. (2002) *Curr. Biol.* 12:1052-1058). Similar to other HMTases, DOT1L contains a S-adenosylmethionine (SAM) binding site and uses SAM as a methyl donor. However, unlike other reported HMTases, the DOT1 polypeptides do not contain a SET domain.

DOT1L nucleic acid and polypeptides have previously been described (see, e.g., U.S. Patent Application Publication No. 2005-0048634 A1 (incorporated by reference); Feng et al. (2002) *Curr. Biol.* 12:1052-1058; and Okada et al. (2005) *Cell* 121:167-78). The yeast homolog of DOT1 was originally identified as a Disruptor of Telomeric silencing (the protein and nucleic acid sequences of yeast DOT1 can be found at GenBank Accession No. NP010728, incorporated herein by reference in its entirety). The human DOT1 homolog has been cloned, isolated, and designated as hDOT1L (human DOT1-like protein). The sequences of the human nucleic acid and protein have been deposited under GenBank Accession No. AF509504, which is hereby incorporated by reference in its entirety. Only the approximately 360 N-terminal amino acids of hDOT1L share significant sequence similarity with the yeast DOT1. In addition, DOT1 homologs from *C. elegans* (GenBank Accession Nos. NP510056 and CAA90610), *Drosophila* (GenBank Accession Nos. CG10272 and AAF54122), mouse (GenBank Accession No. XP125730), *Anopheles gambiae* (GenBank Accession No. EAA03558), and *Neurospora crassa* (GenBank Accession No. EAA33634) are available in public databases (the disclosures of which are incorporated by reference herein in their entireties). The SAM binding domain among these homologs is conserved (approximately 30-100% amino acid sequence identity and 50-100% amino acid similarity). Various aspects of the present invention can be practiced with any DOT1L polypeptide or nucleic acid.

The 2.5 angstrom resolution structure of a fragment of the hDOT1L protein containing the catalytic domain (amino acids 1-416) has been solved; and the atomic coordinates for amino acids 1-416 of hDOT1L have been determined and deposited in the RCSB database under ID code 1NW3 and described in the scientific literature (see Min, et al. (2003) *Cell* 112:711-723), the disclosures of both of which are incorporated herein by reference in their entireties.

It has recently been demonstrated that hDOT1L plays an important role in MLL-AF10-mediated leukemogenesis (Okada et al. (2005) *Cell* 121:167-78). It was also shown that mistargeting of hDOT1L to the Hoxa9 gene by MLL-AF10 results in H3K79 methylation and Hoxa9 upregulation which contributes to leukemic transformation (Okada et al. (2005) *Cell* 121:167-78). It was further demonstrated that the hDOT1L and MLL-AF10 interaction involves the OM-LZ (octapeptide motif-leucine zipper) region of AF10, required for MLL-AF10-mediated leukemic transformation (DiMartino et al. (2002) *Blood* 99:3780-5). It has also been shown that CALM-AF10 fusion appears to be both necessary and sufficient to mediate leukemogenesis in vitro and in vivo; that hDOT1L and its H3K79 methyltransferase activity are implicated in CALM-AF10-mediated leukemic transformation; and that the Hoxa5 gene is involved in CALM-AF10-mediated transformation (U.S. Patent Application Publication No. 2009-0061443 A1, which is hereby incorporated by reference in its entirety). Aberrant recruitment of DOT1L leading to deregulated gene expression may be a common feature of many other oncogenic MLL-fusion proteins. For example, the MLL fusion partners ENL, AF4, and AF9 are normally found in nuclear complexes with DOT1L (Bitoun et al. (2007) *Hum. Mol. Genet.* 16:92-106, Mueller et al. (2007) *Blood* 110:4445-54, Zhang et al. (2006) *J. Biol. Chem.* 281:18059-68), and altered H3K79 methylation profiles are a feature of murine and human MLL-AF4 leukemias (Krivstov et al. (2008) *Cancer Cell* 14:355-368).

Compounds

One aspect of the invention relates to a compound of formula I:

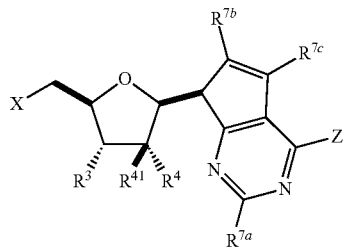

or a pharmaceutically acceptable salt, hydrate, enantiomer or stereoisomer thereof, wherein independently for each occurrence, X is

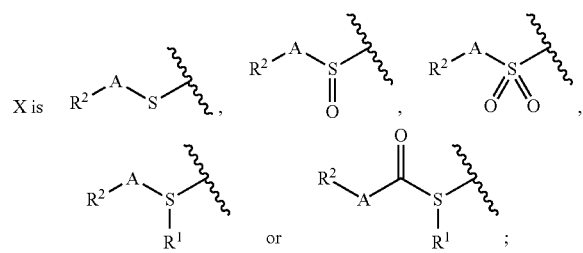

$R^1$ is hydrogen, alkyl, cycloalkyl, alkylcycloalkyl, alkylaryl, haloalkyl, formyl, heterocyclyl, heterocyclylalkyl,

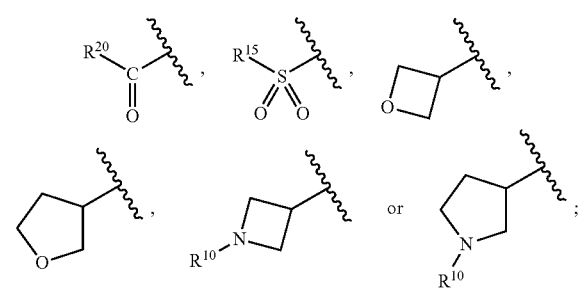

or $(C_2-C_4)$ alkyl substituted with

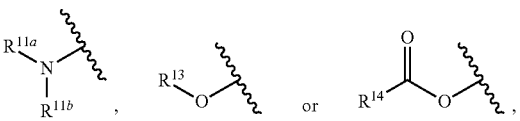

except that when X is

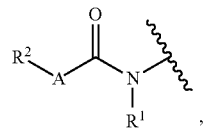

$R^1$ is not

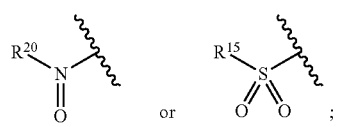

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl or silyl;
$R^{14}$ is hydrogen, alkyl, aryl, heteroaryl, aralkyl or heteroaralkyl;
$R^{15}$ is alkyl, cycloalkyl or cycloalkylalkyl;
$R^{20}$ is hydrogen, alkyl, cycloalkyl or cycloalkylalkyl;

A is

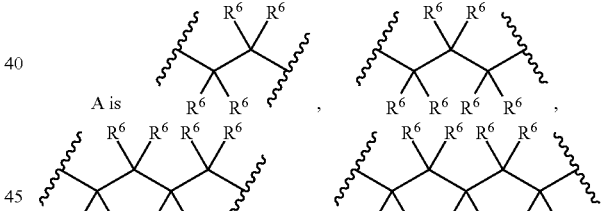

$R^2$ is

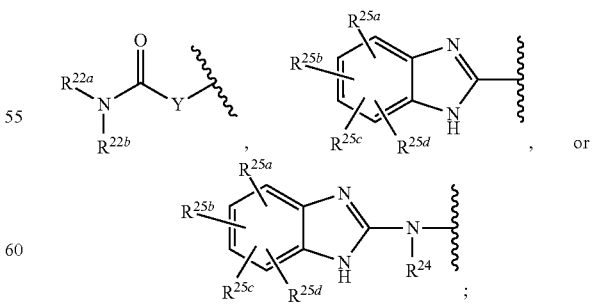

Y is —NH—, —N(alkyl)-, —O—, or —$CR^6_2$—;
$R^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;

$R^{22b}$ is hydrogen or alkyl;

$R^{24}$ is hydrogen or alkyl;

$R^{25a}$, $R^{25b}$, $R^{25c}$, and $R^{25d}$ independently are $-M_2-T_2$, in which $M_2$ is a bond, $SO_2$, $SO$, $S$, $CO$, $CO_2$, $O$, $O-C_1-C_4$ alkyl linker, $C_1-C_4$ alkyl linker, NH, or $N(R_t)$, $R_t$ being $C_1-C_6$ alkyl, and $T_2$ is H, halo, or $R_{S4}$, $R_{S4}$ being $C_1-C_6$ alkyl, $C_2-C_6$ alkenyl, $C_2-C_6$ alkynyl, $C_3-C_8$ cycloalkyl, $C_6-C_{10}$ aryl, 4 to 8-membered heterocycloalkyl, or 5 to 10-membered heteroaryl, and each of $O-C_1-C_4$ alkyl linker, $C_1-C_4$ alkyl linker, $R_t$, and $R_{S4}$ being optionally substituted with one or more substituents selected from the group consisting of halo, hydroxyl, carboxyl, cyano, $C_1-C_6$ alkyl, $C_2-C_6$ alkenyl, $C_2-C_6$ alkynyl, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, and 5 to 6-membered heteroaryl;

$R^3$ is hydrogen, halogen, hydroxy, alkyloxy, aralkyloxy, alkylcarbonyloxy or silyloxy;

$R^4$ is hydrogen, halogen, hydroxy, alkyloxy, aralkyloxy, alkylcarbonyloxy or silyloxy;

$R^{41}$ is hydrogen, alkyl or alkynyl;

Z is hydrogen or

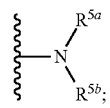

$R^{5a}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl:

$R^{5b}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with $R^{5a}$ and the nitrogen to which it is attached forms a 4- to 8-membered heterocyclyl comprising 0 or 1 additional heteroatoms;

$R^6$ is hydrogen, alkyl or halo; or two geminal $R^6$ taken together are ethylene, propylene or butylene;

$R^{7a}$ is hydrogen, lower alkyl, lower haloalkyl, cyano, halo, lower alkoxy, or $C_3-C_5$ cycloalkyl, optionally substituted with 1, 2 or 3 substituents independently selected from the group consisting of cyano, lower alkoxy and halo;

$R^{7b}$ is hydrogen, lower alkyl, lower haloalkyl, cyano, halo, lower alkoxy, or $C_3-C_5$ cycloalkyl, optionally substituted with 1, 2 or 3 substituents independently selected from the group consisting of cyano, lower alkoxy and halo; and $R^{7c}$ is hydrogen, lower alkyl, lower haloalkyl, cyano, halo, lower alkoxy, or $C_3-C_5$ cycloalkyl, optionally substituted with 1, 2 or 3 substituents independently selected from the group consisting of cyano, lower alkoxy and halo.

In certain embodiments, the invention relates to any one of the aforementioned compounds, wherein X is

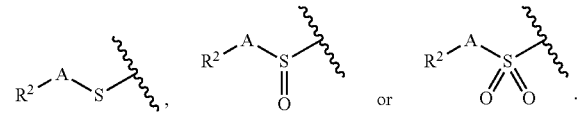

In certain embodiments, the invention relates to any one of the aforementioned compounds, wherein X is

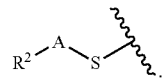

In certain embodiments, the invention relates to any one of the aforementioned compounds, wherein X is

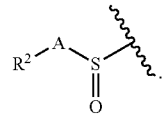

In certain embodiments, the invention relates to any one of the aforementioned compounds, wherein X is

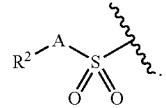

In certain embodiments, the invention relates to any one of the aforementioned compounds, wherein X is

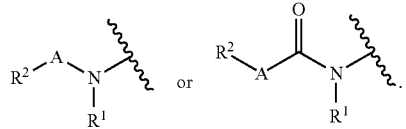

In certain embodiments, the invention relates to any one of the aforementioned compounds, wherein X is

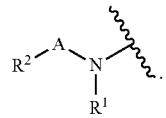

In certain embodiments, the invention relates to any one of the aforementioned compounds, wherein X is

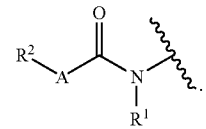

In certain embodiments, the invention relates to any one of the aforementioned compounds, wherein R² is

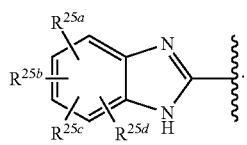

In certain embodiments, the invention relates to any one of the aforementioned compounds, wherein R² is

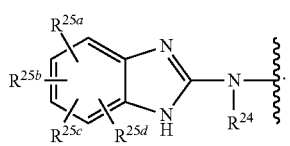

In certain embodiments, the invention relates to any one of the aforementioned compounds, wherein R²⁴ is hydrogen or alkyl.

In certain embodiments, the invention relates to any one of the aforementioned compounds, wherein R²⁴ is hydrogen.

In certain embodiments, the invention relates to any one of the aforementioned compounds, wherein R²⁵ᵃ is hydrogen, alkyl, —O-alkyl, halogen, trifluoroalkyl, —O-trifluoromethyl, or —SO₂-trifluoromethyl.

In certain embodiments, the invention relates to any one of the aforementioned compounds, wherein R²⁵ᵇ hydrogen, alkyl, halogen, or trifluoroalkyl.

In certain embodiments, the invention relates to any one of the aforementioned compounds, wherein R²⁵ᶜ is hydrogen, alkyl, or halogen.

In certain embodiments, the invention relates to any one of the aforementioned compounds, wherein R²⁵ᶜ is hydrogen or halogen.

In certain embodiments, the invention relates to any one of the aforementioned compounds, wherein R² is

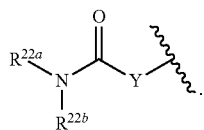

In certain embodiments, the invention relates to any one of the aforementioned compounds, wherein Y is —NH— or —N(alkyl)-.

In certain embodiments, the invention relates to any one of the aforementioned compounds, wherein Y is —NH—.

In certain embodiments, the invention relates to any one of the aforementioned compounds, wherein Y is —N(CH₃)—.

In certain embodiments, the invention relates to any one of the aforementioned compounds, wherein Y is —O—.

In certain embodiments, the invention relates to any one of the aforementioned compounds, wherein Y is —CH₂—.

In certain embodiments, the invention relates to any one of the aforementioned compounds, wherein R²²ᵃ is aryl or aralkyl.

In certain embodiments, the invention relates to any one of the aforementioned compounds, wherein R²²ᵃ is substituted phenyl or substituted benzyl.

In certain embodiments, the invention relates to any one of the aforementioned compounds, wherein R²²ᵃ is

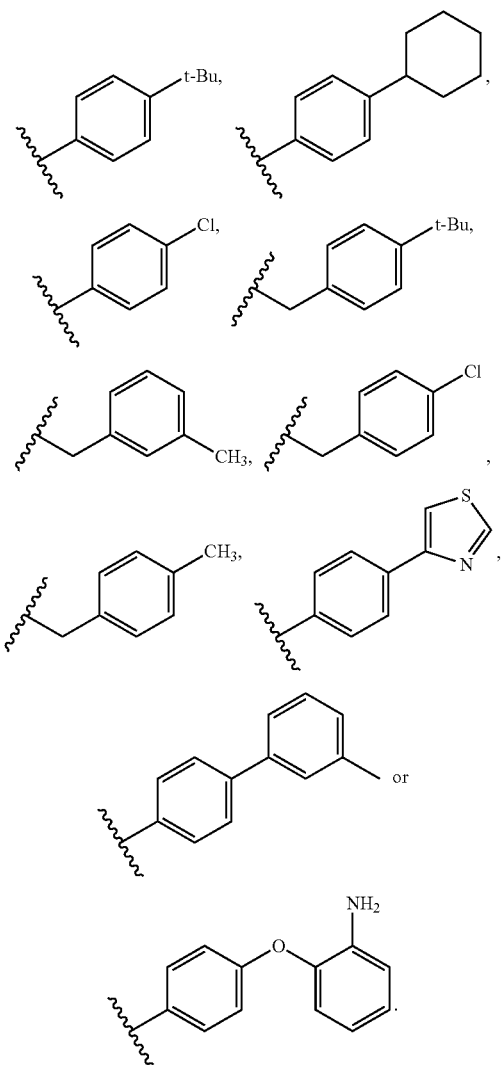

In certain embodiments, the invention relates to any one of the aforementioned compounds, wherein R²²ᵃ is

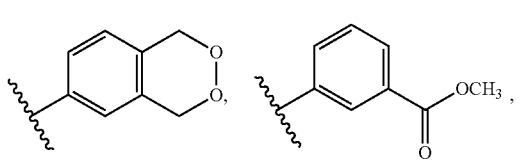

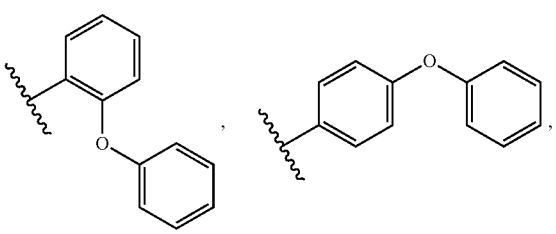

-continued

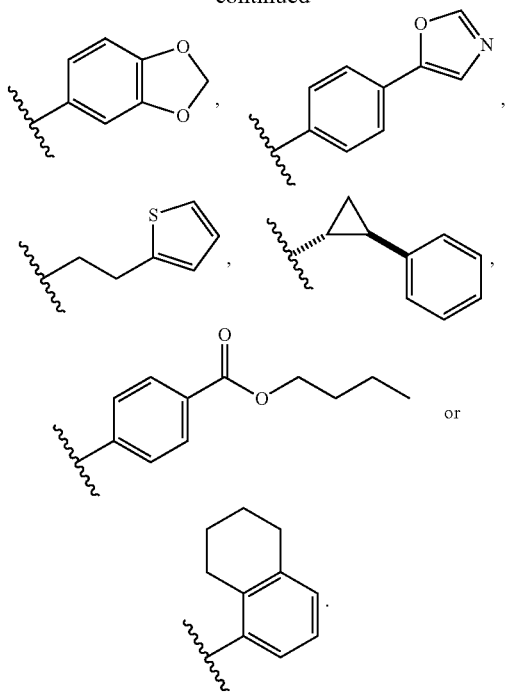

or

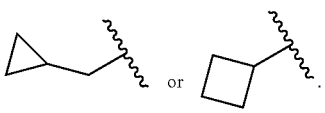 [SMILES: *CC1CC1 ; *C1CCC1]

In certain embodiments, the invention relates to any one of the aforementioned compounds, wherein $R^{22b}$ is hydrogen.

In certain embodiments, the invention relates to any one of the aforementioned compounds, wherein $R^{22b}$ is methyl.

In certain embodiments, the invention relates to any one of the aforementioned compounds, wherein $R^1$ is hydrogen.

In certain embodiments, the invention relates to any one of the aforementioned compounds, wherein $R^1$ is alkyl.

In certain embodiments, the invention relates to any one of the aforementioned compounds, wherein $R^1$ is —CH$_3$, —CH$_2$CH$^3$, —CH$_2$CH(CH$_3$)$_2$ or —CH$_2$CH$_2$CH(CH$_3$)$_2$.

In certain embodiments, the invention relates to any one of the aforementioned compounds, wherein $R^1$ is $C_3$-$C_7$ cycloalkyl.

In certain embodiments, the invention relates to any one of the aforementioned compounds, wherein $R^1$ is cyclopropyl, cyclopropylmethyl, 2-cyclopropylethyl, cyclobutyl, cyclobutylmethyl, 2-cyclobutylethyl, cyclopentyl, cyclopentylmethyl, or 2-cyclopentylethyl.

In certain embodiments, the invention relates to any one of the aforementioned compounds, wherein $R^1$ is

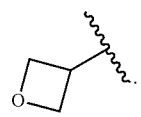

In certain embodiments, the invention relates to any one of the aforementioned compounds, wherein $R^1$ is —CH$_2$CF$_3$.

In certain embodiments, the invention relates to any one of the aforementioned compounds, wherein $R^1$ is —CH$_2$Ph.

In certain embodiments, the invention relates to any one of the aforementioned compounds, wherein $R^1$ is —C(=O)H.

In certain embodiments, the invention relates to any one of the aforementioned compounds, wherein $R^1$ is —C(=O)CH$_3$.

In certain embodiments, the invention relates to any one of the aforementioned compounds, wherein $R^1$ is heterocyclyl or heterocyclylalkyl.

In certain embodiments, the invention relates to any one of the aforementioned compounds, wherein $R^1$ is

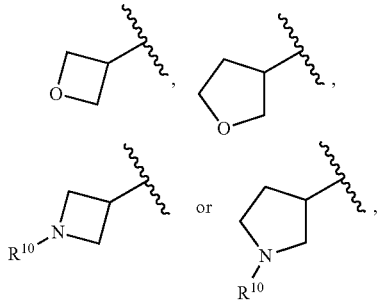

In certain embodiments, the invention relates to any one of the aforementioned compounds, wherein $R^1$ is

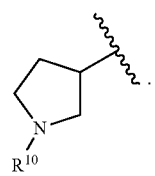

In certain embodiments, the invention relates to any one of the aforementioned compounds, wherein $R^1$ is

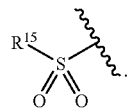

In certain embodiments, the invention relates to any one of the aforementioned compounds, wherein $R^1$ is In certain embodiments, the invention relates to any one of the aforementioned compounds, wherein $R^{15}$ is alkyl.

In certain embodiments, the invention relates to any one of the aforementioned compounds, wherein $R^{15}$ is cycloalkyl.

In certain embodiments, the invention relates to any one of the aforementioned compounds, wherein $R^{15}$ is cycloalkylalkyl.

In certain embodiments, the invention relates to any one of the aforementioned compounds, wherein $R^1$ is ($C_2$-$C_4$) alkyl substituted with

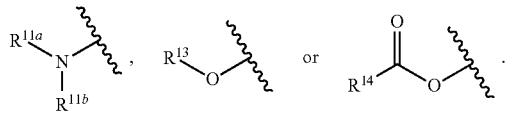

In certain embodiments, the invention relates to any one of the aforementioned compounds, wherein $R^1$ is

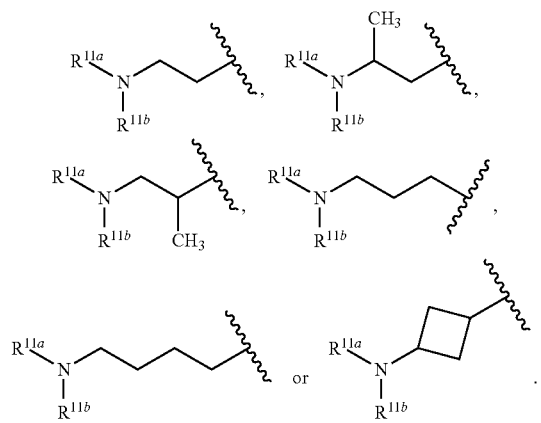

In certain embodiments, the invention relates to any one of the aforementioned compounds, wherein $R^{11a}$ is hydrogen, alkyl, or alkyl-cycloalkyl.

In certain embodiments, the invention relates to any one of the aforementioned compounds, wherein $R^{11a}$ is hydrogen, methyl, or i-propyl.

In certain embodiments, the invention relates to any one of the aforementioned compounds, wherein $R^1$ is

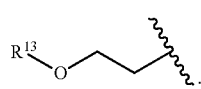

In certain embodiments, the invention relates to any one of the aforementioned compounds, wherein $R^{13}$ is hydrogen.

In certain embodiments, the invention relates to any one of the aforementioned compounds, wherein $R^1$ is

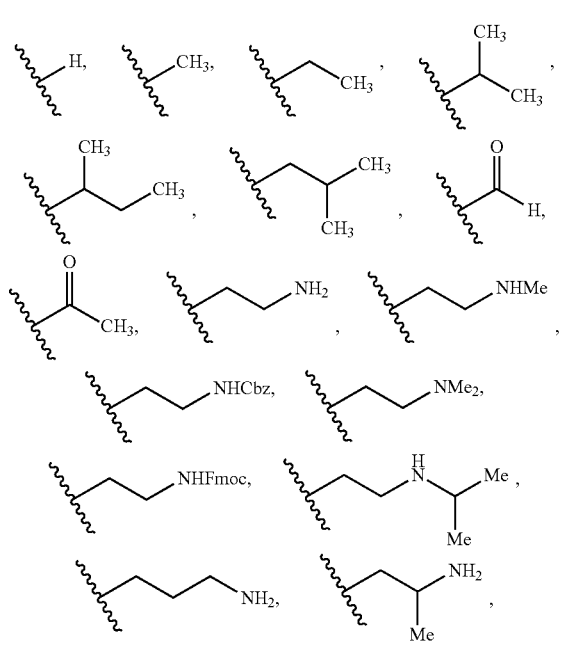

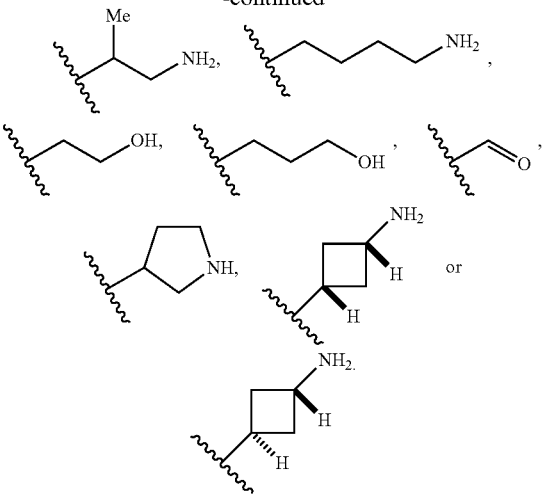

In certain embodiments, the invention relates to any one of the aforementioned compounds, wherein A is

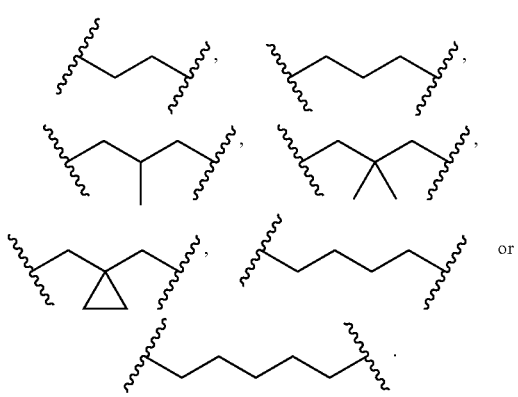

In certain embodiments, the invention relates to any one of the aforementioned compounds, wherein A is

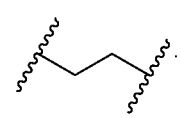

In certain embodiments, the invention relates to any one of the aforementioned compounds, wherein A is

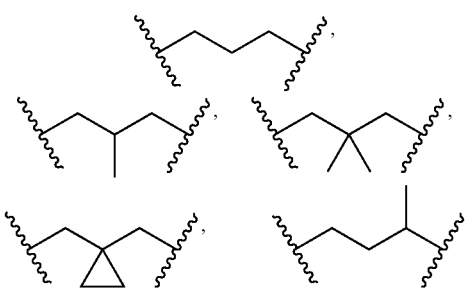

-continued

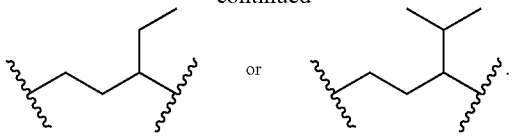

In certain embodiments, the invention relates to any one of the aforementioned compounds, wherein A is

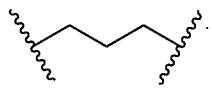 [SMILES: *CCC*]

In certain embodiments, the invention relates to any one of the aforementioned compounds, wherein A is

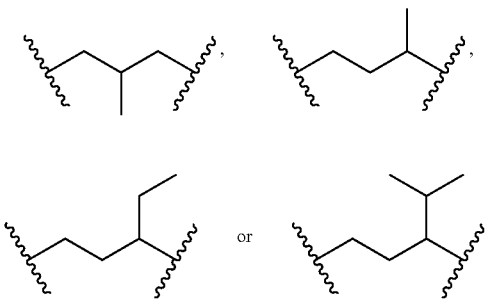

In certain embodiments, the invention relates to any one of the aforementioned compounds, wherein A is

In certain embodiments, the invention relates to any one of the aforementioned compounds, wherein A is

In certain embodiments, the invention relates to any one of the aforementioned compounds, wherein A is

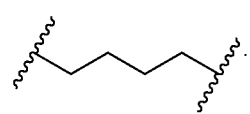 [SMILES: *CCCC*]

In certain embodiments, the invention relates to any one of the aforementioned compounds, wherein A is

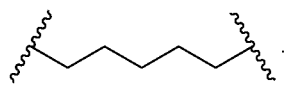 [SMILES: *CCCCC*]

In certain embodiments, the invention relates to any one of the aforementioned compounds, wherein A is

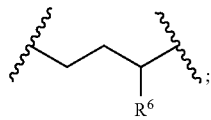

and $R^6$ is alkyl.

In certain embodiments, the invention relates to any one of the aforementioned compounds, wherein A is

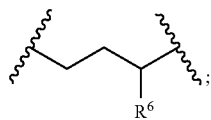

and $R^6$ is methyl, ethyl or isopropyl.

In certain embodiments, the invention relates to any one of the aforementioned compounds, wherein $R^3$ is hydroxyl.

In certain embodiments, the invention relates to any one of the aforementioned compounds, wherein $R^3$ is hydrogen.

In certain embodiments, the invention relates to any one of the aforementioned compounds, wherein $R^4$ is hydroxyl.

In certain embodiments, the invention relates to any one of the aforementioned compounds, wherein $R^4$ is hydrogen.

In certain embodiments, the invention relates to any one of the aforementioned compounds, wherein $R^{41}$ is hydrogen.

In certain embodiments, the invention relates to any one of the aforementioned compounds, wherein $R^{41}$ is methyl.

In certain embodiments, the invention relates to any one of the aforementioned compounds, wherein $R^3$ is hydroxyl; and $R^4$ is hydroxyl.

In certain embodiments, the invention relates to any one of the aforementioned compounds, wherein $R^3$ is hydroxyl; $R^4$ is hydroxyl; and $R^{41}$ is hydrogen.

In certain embodiments, the invention relates to any one of the aforementioned compounds, wherein $R^3$ is hydroxyl; $R^4$ is hydroxyl; and $R^{41}$ is methyl.

In certain embodiments, the invention relates to any one of the aforementioned compounds, wherein $R^3$ is hydrogen; and $R^4$ is hydroxyl.

In certain embodiments, the invention relates to any one of the aforementioned compounds, wherein $R^3$ is hydrogen; $R^4$ is hydroxyl; and $R^{41}$ is hydrogen.

In certain embodiments, the invention relates to any one of the aforementioned compounds, wherein $R^3$ is hydrogen; $R^4$ is hydroxyl; and $R^{41}$ is methyl.

In certain embodiments, the invention relates to any one of the aforementioned compounds, wherein $R^3$ is hydroxyl; and $R^4$ is hydrogen.

In certain embodiments, the invention relates to any one of the aforementioned compounds, wherein $R^3$ is hydroxyl; $R^4$ is hydrogen; and $R^{41}$ is hydrogen.

In certain embodiments, the invention relates to any one of the aforementioned compounds, wherein $R^3$ is hydroxyl; $R^4$ is hydrogen; and $R^{41}$ is methyl.

In certain embodiments, the invention relates to any one of the aforementioned compounds, wherein Z is hydrogen or

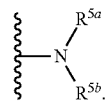

In certain embodiments, the invention relates to any one of the aforementioned compounds, wherein Z is hydrogen.

In certain embodiments, the invention relates to any one of the aforementioned compounds, wherein Z is

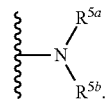

In certain embodiments, the invention relates to any one of the aforementioned compounds, wherein $R^{5a}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned compounds, wherein $R^{5a}$ is hydrogen, aralkyloxyalkyl, alkyl, aryl, aralkyl, aminoalkyl or hydroalkyl.

In certain embodiments, the invention relates to any one of the aforementioned compounds, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_2$Ph, —CH$_2$CH$_2$NH$_2$, —CH$_2$(cyclohexyl) or —CH$_2$CH$_2$OH.

In certain embodiments, the invention relates to any one of the aforementioned compounds, wherein $R^{5b}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned compounds, wherein $R^{5b}$ is hydrogen, aralkyloxyalkyl, alkyl, aryl, aralkyl, aminoalkyl or hydroalkyl.

In certain embodiments, the invention relates to any one of the aforementioned compounds, wherein $R^{5b}$ is hydrogen.

In certain embodiments, the invention relates to any one of the aforementioned compounds, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$ (cyclohexyl) or —CH$_2$CH$_2$OH; and $R^{5b}$ is —H.

In certain embodiments, the invention relates to any one of the aforementioned compounds, wherein $R^7$ is hydrogen or lower alkyl.

In certain embodiments, the invention relates to any one of the aforementioned compounds, wherein $R^{7a}$ is hydrogen.

In certain embodiments, the invention relates to any one of the aforementioned compounds, wherein $R^{7b}$ is hydrogen or lower alkyl.

In certain embodiments, the invention relates to any one of the aforementioned compounds, wherein $R^{7b}$ is hydrogen.

In certain embodiments, the invention relates to any one of the aforementioned compounds, wherein $R^{7c}$ is hydrogen or lower alkyl.

In certain embodiments, the invention relates to any one of the aforementioned compounds, wherein $R^{7c}$ is hydrogen.

One aspect of the invention relates to a compound, or a pharmaceutically acceptable salt, hydrate, enantiomer or stereoisomer thereof, is selected from the group consisting of

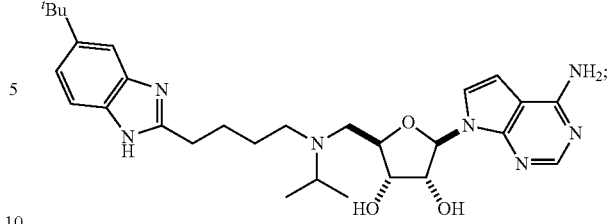

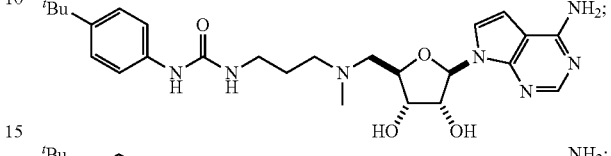

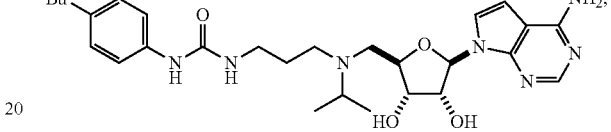

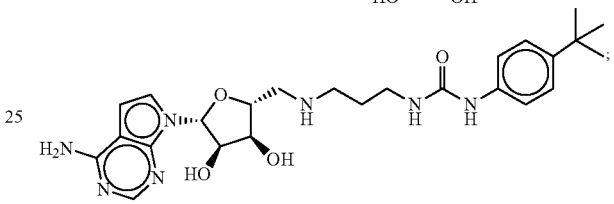

and

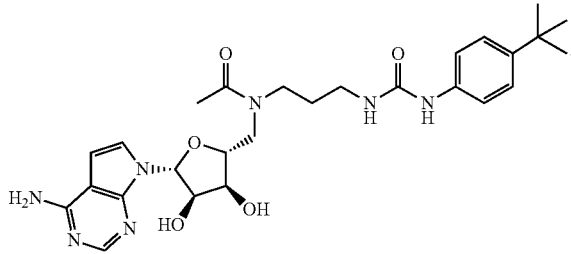

In certain embodiments, the invention relates to any one of the aforementioned compounds, wherein the compound inhibits DOT1L with an IC$_{50}$ of less than about 10 µM. In certain embodiments, the invention relates to any one of the aforementioned compounds, wherein the compound inhibits DOT1L with an IC$_{50}$ of less than about 5 µM. In certain embodiments, the invention relates to any one of the aforementioned compounds, wherein the compound inhibits DOT1L with an IC$_{50}$ of less than about 1 µM. In certain embodiments, the invention relates to any one of the aforementioned compounds, wherein the compound inhibits DOT1L with an IC$_{50}$ of less than about 750 nM. In certain embodiments, the invention relates to any one of the aforementioned compounds, wherein the compound inhibits DOT1L with an IC$_{50}$ of less than about 500 nM. In certain embodiments, the invention relates to any one of the aforementioned compounds, wherein the compound inhibits DOT1L with an IC$_{50}$ of less than about 250 nM. In certain embodiments, the invention relates to any one of the aforementioned compounds, wherein the compound inhibits DOT1L with an IC$_{50}$ of less than about 100 nM.

In certain embodiments, the invention relates to any one of the aforementioned compounds, wherein the compound is a selective inhibitor of DOT1L.

In certain embodiments, the invention relates to any one of the aforementioned compounds, wherein the compound inhibits both DOT1L and EZH2; the compound has a DOT1L $IC_{50}$ of between about 0.001 µM and about 10 µM; and the ratio of the EZH2 $IC_{50}$ to the DOT1L $IC_{50}$ is between about 10 and about 50. In certain embodiments, the invention relates to any one of the aforementioned compounds, wherein the compound inhibits both DOT1L and EZH2; the compound has a DOT1L $IC_{50}$ of between about 0.001 µM and about 10 µM; and the ratio of the EZH2 $IC_{50}$ to the DOT1L $IC_{50}$ is between about 50 and about 100. In certain embodiments, the invention relates to any one of the aforementioned compounds, wherein the compound inhibits both DOT1L and EZH2; the compound has a DOT1L $IC_{50}$ of between about 0.001 µM and about 10 µM; and the ratio of the EZH2 $IC_{50}$ to the DOT1L $IC_{50}$ is between about 100 and about 1,000.

In certain embodiments, the invention relates to any one of the aforementioned compounds, wherein the compound inhibits both DOT1L and EHMT2; the compound has a DOT1L $IC_{50}$ of between about 0.001 µM and about 10 µM; and the ratio of the EHMT2 $IC_{50}$ to the DOT1L $IC_{50}$ is between about 10 and about 50. In certain embodiments, the invention relates to any one of the aforementioned compounds, wherein the compound inhibits both DOT1L and EHMT2; the compound has a DOT1L $IC_{50}$ of between about 0.001 µM and about 10 µM; and the ratio of the EHMT2 $IC_{50}$ to the DOT1L $IC_{50}$ is between about 50 and about 100. In certain embodiments, the invention relates to any one of the aforementioned compounds, wherein the compound inhibits both DOT1L and EHMT2; the compound has a DOT1L $IC_{50}$ of between about 0.001 µM and about 10 µM; and the ratio of the EHMT2 $IC_{50}$ to the DOT1L $IC_{50}$ is between about 100 and about 1,000.

In certain embodiments, the invention relates to any one of the aforementioned compounds, wherein the compound inhibits both DOT1L and CARM1; the compound has a DOT1L $IC_{50}$ of between about 0.001 µM and about 10 µM; and the ratio of the CARM1 $IC_{50}$ to the DOT1L $IC_{50}$ is between about 10 and about 50. In certain embodiments, the invention relates to any one of the aforementioned compounds, wherein the compound inhibits both DOT1L and CARM1; the compound has a DOT1L $IC_{50}$ of between about 0.001 µM and about 10 µM; and the ratio of the CARM1 $IC_{50}$ to the DOT1L $IC_{50}$ is between about 50 and about 100. In certain embodiments, the invention relates to any one of the aforementioned compounds, wherein the compound inhibits both DOT1L and CARM1; the compound has a DOT1L $IC_{50}$ of between about 0.001 µM and about 10 µM; and the ratio of the CARM1 $IC_{50}$ to the DOT1L $IC_{50}$ is between about 100 and about 1,000.

In certain embodiments, the invention relates to any one of the aforementioned compounds, wherein the compound inhibits both DOT1L and PRMT5; the compound has a DOT1L $IC_{50}$ of between about 0.001 µM and about 10 µM; and the ratio of the PRMT5 $IC_{50}$ to the DOT1L $IC_{50}$ is between about 10 and about 50. In certain embodiments, the invention relates to any one of the aforementioned compounds, wherein the compound inhibits both DOT1L and PRMT5; the compound has a DOT1L $IC_{50}$ of between about 0.001 µM and about 10 µM; and the ratio of the PRMT5 $IC_{50}$ to the DOT1L $IC_{50}$ is between about 50 and about 100. In certain embodiments, the invention relates to any one of the aforementioned compounds, wherein the compound inhibits both DOT1L and PRMT5; the compound has a DOT1L $IC_{50}$ of between about 0.001 µM and about 10 µM; and the ratio of the PRMT5 $IC_{50}$ to the DOT1L $IC_{50}$ is between about 100 and about 1,000.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes such salts.

Pharmaceutically acceptable acid addition salts include those formed with mineral acids such as hydrochloric acid and hydrobromic acid, and also those formed with organic acids such as maleic acid. For example, acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystalline form (i.e., polymorph); the present invention includes each of the crystal forms and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures thereof. The enantiomers may be resolved by methods known to those skilled in the art; for example, enantiomers may be resolved by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, via enzymatic esterification; or gas-liquid or liquid chromatography in a chiral environment, for example, on a chiral support; suitable include chiral supports (e.g., silica with a bound chiral ligand) or in the presence of a chiral solvent. Where the desired enantiomer is converted into another chemical entity by one of the separation procedures described above, a further step may be used to liberate the desired purified enantiomer. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the various diastereoisomers of compounds of the invention, and mixtures thereof. Compounds of the invention may exist in different tautomeric forms or as different geometric isomers, and the present invention includes each tautomer and/or geometric isomer of compounds of the invention, and mixtures thereof. Compounds of the invention may exist in zwitterionic form. The present invention includes each zwitterionic form of compounds of the invention, and mixtures thereof.

As used herein the term "prodrug" refers to an agent which is converted into the parent drug in vivo by some physiological chemical process (e.g., a prodrug on being brought to the physiological pH is converted to the desired drug form). Prodrugs are often useful because, in some situations. they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial. Prodrugs have many useful properties. For example, a prodrug may be more water soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Exemplary prodrugs release an amine of a compound of the invention wherein the free hydrogen of an amine or alcohol is replaced by $(C_1-C_6)$alkanoyloxymethyl, 1-(($(C_1-C_6)$alkanoyloxy)ethyl, 1-methyl-1-(($(C_1-C_6)$alkanoyloxy)ethyl, $(C_1-C_6)$ alkoxycarbonyl-oxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O$(C_1-C_6)$alkyl)$_2$ or glycosyl (the radical resulting from detachment of the hydroxyl of the hemiacetal of a carbohydrate).

Other exemplary prodrugs upon cleavage release a corresponding free acid, and such hydrolyzable ester-forming residues of the compounds of the invention include but are not limited to carboxylic acid substituents (e.g., —(CH$_2$)C(O)OH or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$ alkyl.

General Synthetic Schemes

Figure 2:
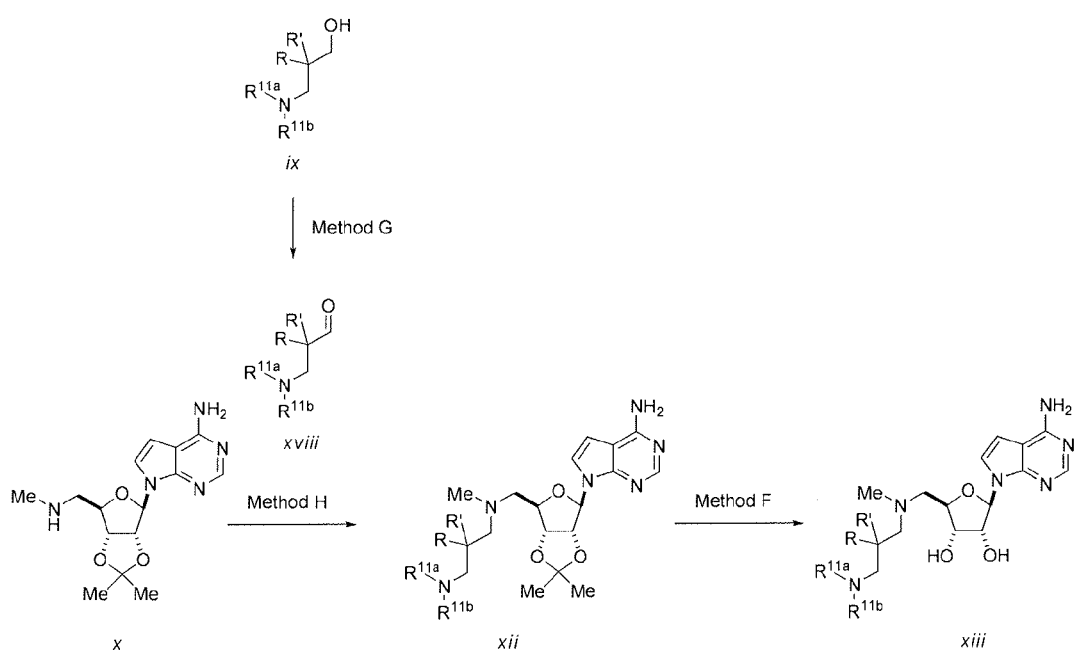
FIG. 2 depicts general routes for preparing compounds of the invention.

The following describes the general synthetic procedures shown in FIGS. 1 and 2. Unless noted otherwise, none of the specific conditions and reagents noted in the following is to be construed as limiting the scope of the instant invention and are provided for illustrative purposes only. All of the general procedures have been successfully performed and exemplifications of each general procedure are also provided.

FIG. 1 shows a general route for preparing compounds of formula viii, where $R^{11a}$ is defined in the claim set. Conversion of vi to vii is accomplished by treating with the appropriate isocyanate in a solvent, such as dimethylformamide. Treatment of the resultant urea vii with a protic acid, such as trifluoroacetic acid, in the presence of water, will produce compounds of formula viii.

FIG. 2 shows a general route for the preparation of compounds of formula xiii, where R, R', $R^{11a}$ and $R^{11b}$ is defined in the claim set. Conversion of ix to xviii may be accomplished by treatment with the appropriate oxidizing agent, such as IBX, in the appropriate solvent, such as ethyl acetate. A reductive amination between xviii and x may be accomplished by combining the two reagents in a standard solvent, such as methanol, with a suitable catalyst, such as acetic acid, and an appropriate reductant, such as sodium cyanoborohydride. Treatment of compounds of formula xii under the conditions of method F will result in compounds of formula xiii.

In general, it may be convenient or desirable to prepare, purify, and/or handle any of the compounds in FIGS. 1 and 2 in a chemically protected form. The term "chemically protected form," as used herein, pertains to a compound in which one or more reactive functional groups are protected from undesirable chemical reactions (i.e., they have been modified with a protecting group).

By protecting a reactive functional group, reactions involving other unprotected reactive functional groups can be performed without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$,—OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

For example, a benzimidazole group may be protected with a SEM or benzyl protecting group "Tautomer" is one of two or more structural isomers that exist in equilibrium and which readily convert from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs include: ketone-enol, amide-nitrile, lactam-lactim, amide-imidic acid tautomerism in heterocyclic rings (e.g., in nucleobases such as guanine, thymine and cytosine), amine-enamine and enamine-enamine.

Benzimidazoles also exhibit tautomerism: when the benzimidazole contains one or more substituents in the 4-, 5-, 6- or 7-positions, the possibility of different isomers arises. For example, 2,5-dimethyl-1H-benzo[d]imidazole can exist in equilibrium with its isomer 2,6-dimethyl-1H-benzo[d]imidazole via tautomerization.

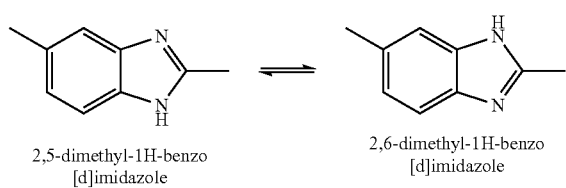

2,5-dimethyl-1H-benzo[d]imidazole 2,6-dimethyl-1H-benzo[d]imidazole

It is to be understood that the compounds of the present invention may be depicted as different tautomers. It should also be understood that when compounds have tautomeric forms, all tautomeric forms are intended to be included in the scope of the present invention, and the specific naming convention used for a particular compound does not exclude any tautomer form.

Pharmaceutical Compositions

One or more compounds of the invention can be administered to a human patient by themselves or in pharmaceutical compositions where they are mixed with suitable carriers or excipient(s) at doses to treat or ameliorate a disease or condition as described herein. Mixtures of these compounds can also be administered to the patient as a simple mixture or in suitable formulated pharmaceutical compositions. For example, one aspect of the invention relates to pharmaceutical composition comprising a therapeutically effective dose of a compound of formula I, or a pharmaceutically acceptable salt, hydrate, enantiomer or stereoisomer thereof; and a pharmaceutically acceptable diluent or carrier; wherein the compound of formula I is represented by

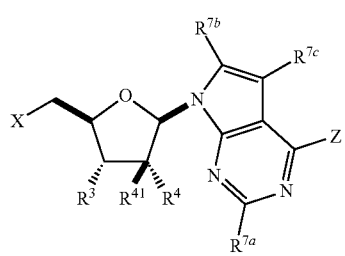

wherein independently for each occurrence,

X is 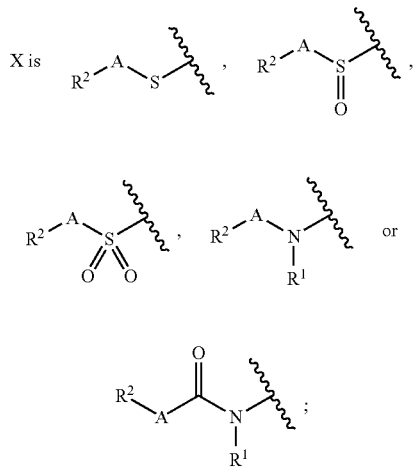

$R^1$ is hydrogen, alkyl, cycloalkyl, alkylcycloalkyl, alkylaryl, haloalkyl, formyl, heterocyclyl, heterocyclylalkyl,

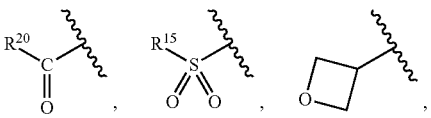

-continued

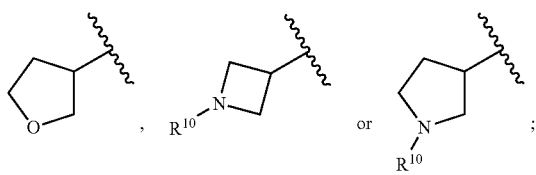

or (C$_2$-C$_4$)alkyl substituted with

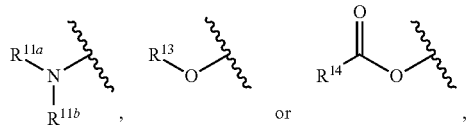

except that when X is

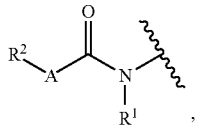

R$^1$ is not

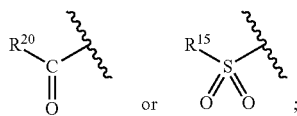

R$^{10}$ is hydrogen or alkyl;

R$^{11a}$ is hydrogen, alkyl, or alkyl-cycloalkyl;

R$^{11b}$ is hydrogen or alkyl; or taken together with R$^{11a}$ and the nitrogen to which it is attached forms a 4- to 8-membered heterocyclyl comprising 0 or 1 additional heteroatoms;

R$^{13}$ is hydrogen, alkyl, aryl, heteroaryl, aralkyl, heteroaralkyl or silyl;

R$^{14}$ is hydrogen, alkyl, aryl, heteroaryl, aralkyl or heteroaralkyl;

R$^{15}$ is alkyl, cycloalkyl or cycloalkylalkyl;

R$^{20}$ is hydrogen, alkyl, cycloalkyl or cycloalkylalkyl;

A is

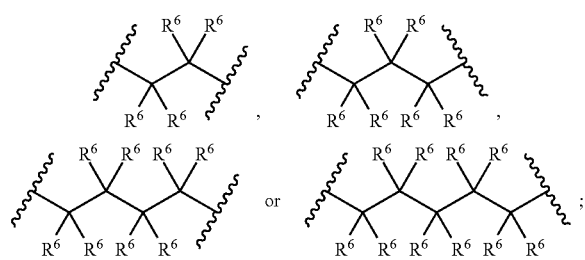

R$^2$ is

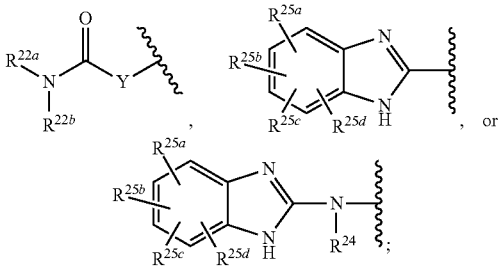

Y is —NH—, —N(alkyl)-, —O—, or —CR$^6_2$—;

R$^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;

R$^{22b}$ is hydrogen or alkyl;

R$^{24}$ is hydrogen or alkyl;

R$^{25a}$, R$^{25b}$, R$^{25c}$, and R$^{25d}$ independently are -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$^3$ is hydrogen, halogen, hydroxy, alkyloxy, aralkyloxy, alkylcarbonyloxy or silyloxy;

R$^4$ is hydrogen, halogen, hydroxy, alkyloxy, aralkyloxy, alkylcarbonyloxy or silyloxy;

R$^{41}$ is hydrogen, alkyl or alkynyl;

Z is hydrogen or

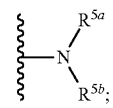

R$^{5a}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl:

R$^{5b}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with R$^{5a}$ and the nitrogen to which it is attached forms a 4- to 8-membered heterocyclyl comprising 0 or 1 additional heteroatoms;

$R^6$ is hydrogen, alkyl or halo; or two geminal $R^6$ taken together are ethylene, propylene or butylene;

$R^{7a}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo;

$R^{7b}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo; and $R^{7c}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo.

Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer a compound in a local rather than a systemic manner, for example, via injection of the compound directly into an edematous site, often in a depot or sustained release formulation.

Furthermore, one may administer a compound in a targeted drug delivery system, for example, in a liposome coated with endothelial-cell-specific antibody.

The pharmaceutical compositions of the present invention may be manufactured, e.g., by conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for reconstitution before use with a suitable vehicle, e.g., sterile pyrogen-free water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical compounds may be employed. Liposomes and emulsions are examples of delivery vehicles or carriers for hydrophobic drugs. Certain organic solvents such as dimethylsulfoxide also may be employed. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Methods of Treatment

Provided herein are methods of treating or preventing conditions and diseases the course of which can be influenced by modulating the methylation status of histones or other proteins, wherein said methylation status is mediated at least in part by the activity of DOT1. Modulation of the methylation status of histones can in turn influence the level of expression of target genes activated by methylation, and/or target genes suppressed by methylation. For example, one aspect of the invention relates to a method comprising administering to a subject in need thereof a therapeutically effective amount of a compound of formula I, or a pharmaceutically acceptable salt, hydrate, enantiomer or stereoisomer thereof; wherein the compound of formula I is represented by

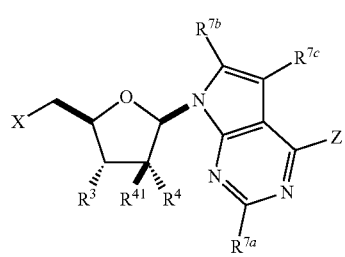

I wherein independently for each occurrence,

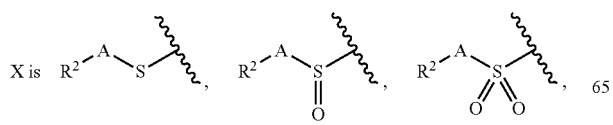

X is

-continued

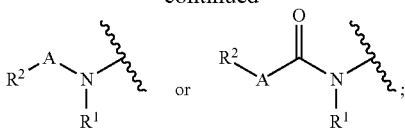

$R^1$ is hydrogen, alkyl, cycloalkyl, alkylcycloalkyl, alkylaryl, haloalkyl, formyl, heterocyclyl, heterocyclylalkyl,

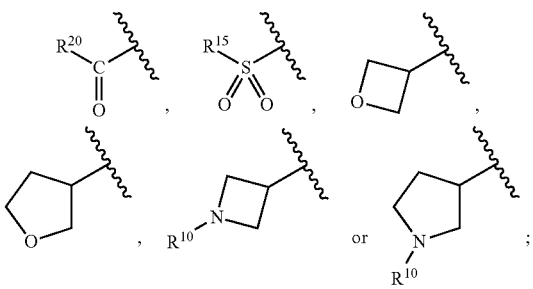

or $(C_2-C_4)$alkyl substituted with

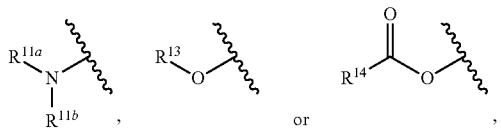

except that when X is

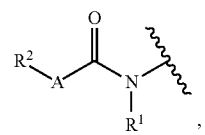

$R^1$ is not

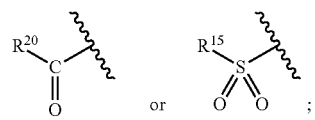

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl or silyl;
$R^{14}$ is hydrogen, alkyl, aryl, heteroaryl, aralkyl or heteroaralkyl;
$R^{15}$ is alkyl, cycloalkyl or cycloalkylalkyl;
$R^{20}$ is hydrogen, alkyl, cycloalkyl or cycloalkylalkyl;
A is

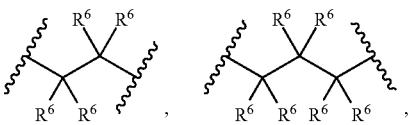

-continued

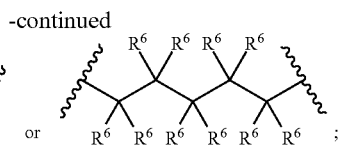

$R^2$ is

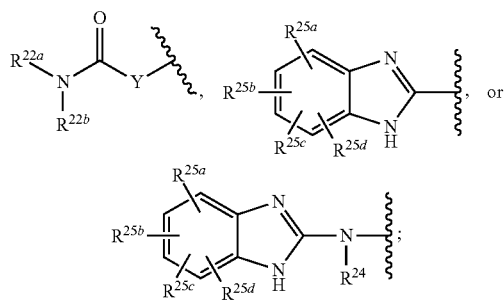

Y is —NH—, —N(alkyl)-, —O—, or —CR$^6$$_2$—;

R$^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;

R$^{22b}$ is hydrogen or alkyl;

R$^{24}$ is hydrogen or alkyl;

R$^{25a}$, R$^{25b}$, R$^{25c}$, and R$^{25d}$ independently are -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$^3$ is hydrogen, halogen, hydroxy, alkyloxy, aralkyloxy, alkylcarbonyloxy or silyloxy;

R$^4$ is hydrogen, halogen, hydroxy, alkyloxy, aralkyloxy, alkylcarbonyloxy or silyloxy;

R$^{41}$ is hydrogen, alkyl or alkynyl;

R$^{5a}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl:

R$^{5b}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl: or taken together with R$^{5a}$ and the nitrogen to which it is attached forms a 4- to 8-membered heterocyclyl comprising 0 or 1 additional heteroatoms;

R$^6$ is hydrogen, alkyl or halo; or two geminal R$^6$ taken together are ethylene, propylene or butylene;

R$^{7a}$ is hydrogen, lower alkyl, lower haloalkyl, cyano, halo, lower alkoxy, or C$_3$-C$_5$ cycloalkyl, optionally substituted with 1, 2 or 3 substituents independently selected from the group consisting of cyano, lower alkoxy and halo;

R$^{7b}$ is hydrogen, lower alkyl, lower haloalkyl, cyano, halo, lower alkoxy, or C$_3$-C$_5$ cycloalkyl, optionally substituted with 1, 2 or 3 substituents independently selected from the group consisting of cyano, lower alkoxy and halo; and R$^{7c}$ is hydrogen, lower alkyl, lower haloalkyl, cyano, halo, lower alkoxy, or C$_3$-C$_5$ cycloalkyl, optionally substituted with 1, 2 or 3 substituents independently selected from the group consisting of cyano, lower alkoxy and halo.

In certain embodiments, the invention related to any one of the aforementioned methods, wherein Z is hydrogen.

In certain embodiments, the invention related to any one of the aforementioned methods, wherein Z is

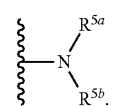

In certain embodiments, the invention relates to any one of the aforementioned methods, wherein X is

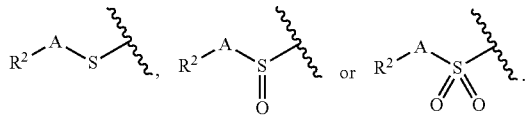

In certain embodiments, the invention relates to any one of the aforementioned methods, wherein X is

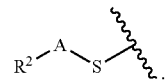

In certain embodiments, the invention relates to any one of the aforementioned methods, wherein X is

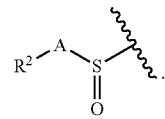

In certain embodiments, the invention relates to any one of the aforementioned methods, wherein X is

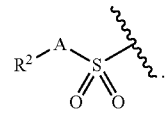

In certain embodiments, the invention relates to any one of the aforementioned methods, wherein X is

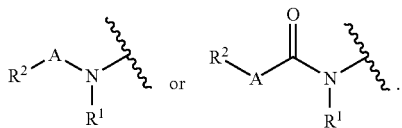

In certain embodiments, the invention relates to any one of the aforementioned methods, wherein X is

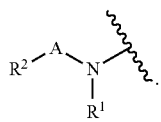

In certain embodiments, the invention relates to any one of the aforementioned methods, wherein X is

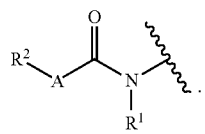

In certain embodiments, the invention relates to any one of the aforementioned methods, wherein $R^2$ is

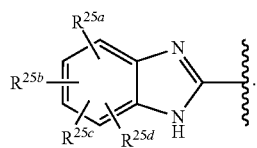

In certain embodiments, the invention relates to any one of the aforementioned methods, wherein $R^2$ is

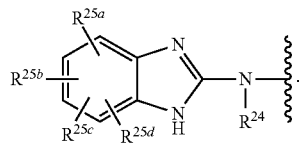

In certain embodiments, the invention relates to any one of the aforementioned methods, wherein $R^{24}$ is hydrogen or alkyl.

In certain embodiments, the invention relates to any one of the aforementioned methods, wherein $R^{24}$ is hydrogen.

In certain embodiments, the invention relates to any one of the aforementioned methods, wherein $R^{25a}$ is hydrogen, alkyl, —O-alkyl, halogen, trifluoroalkyl, —O-trifluoromethyl, or —SO$_2$-trifluoromethyl.

In certain embodiments, the invention relates to any one of the aforementioned methods, wherein $R^{25b}$ is hydrogen, alkyl, halogen, or trifluoroalkyl.

In certain embodiments, the invention relates to any one of the aforementioned methods, wherein $R^{25c}$ is hydrogen, alkyl, or halogen.

In certain embodiments, the invention relates to any one of the aforementioned methods, wherein $R^{25c}$ is hydrogen or halogen.

In certain embodiments, the invention relates to any one of the aforementioned methods, wherein $R^2$ is

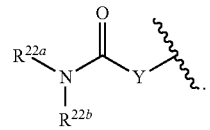

In certain embodiments, the invention relates to any one of the aforementioned methods, wherein Y is —NH— or —N(alkyl)-.

In certain embodiments, the invention relates to any one of the aforementioned methods, wherein Y is —NH—.

In certain embodiments, the invention relates to any one of the aforementioned methods, wherein Y is —N(CH$_3$)—.

In certain embodiments, the invention relates to any one of the aforementioned methods, wherein Y is —O—.

In certain embodiments, the invention relates to any one of the aforementioned methods, wherein Y is —CH$_2$—.

In certain embodiments, the invention relates to any one of the aforementioned methods, wherein $R^{22a}$ is aryl or aralkyl.

In certain embodiments, the invention relates to any one of the aforementioned methods, wherein $R^{22a}$ is substituted phenyl or substituted benzyl.

In certain embodiments, the invention relates to any one of the aforementioned methods, wherein $R^{22a}$ is

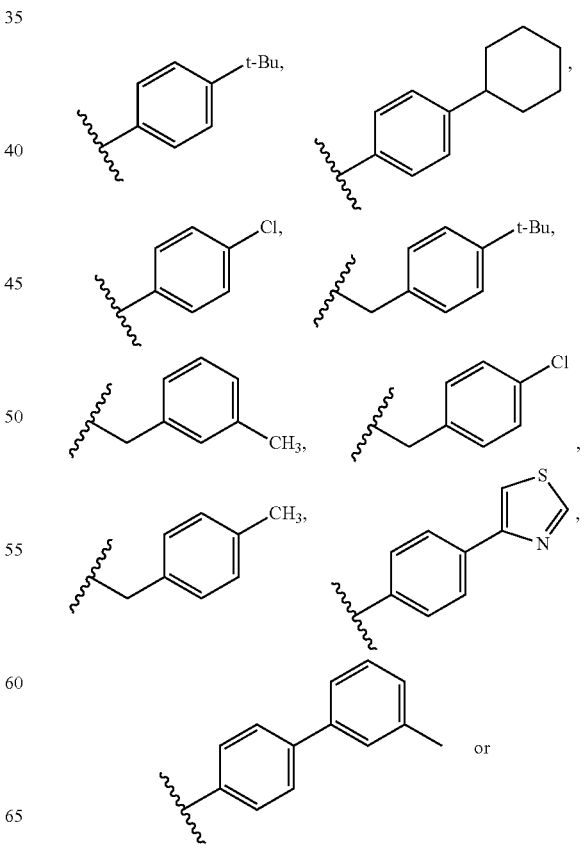

-continued

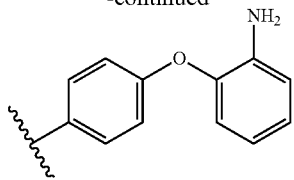

In certain embodiments, the invention relates to any one of the aforementioned methods, wherein $R^{22a}$ is

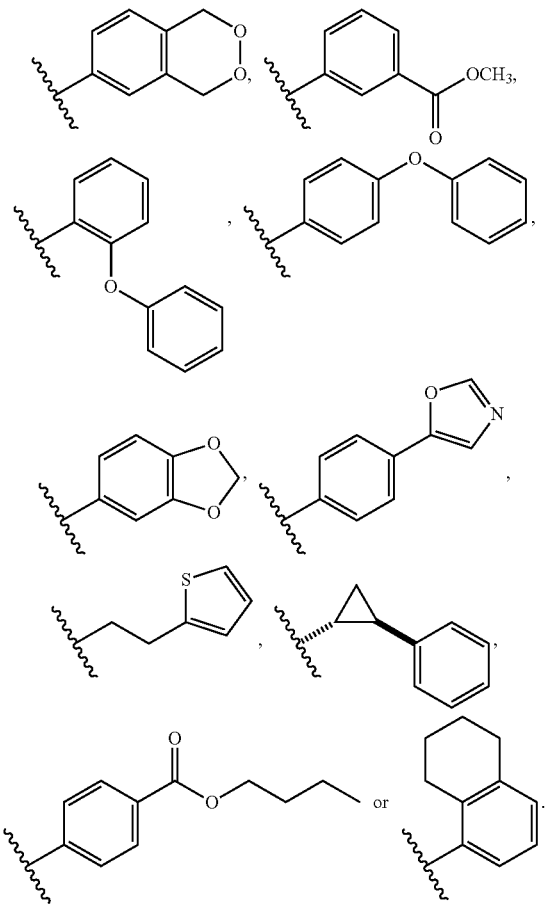

In certain embodiments, the invention relates to any one of the aforementioned methods, wherein $R^{22b}$ is hydrogen.

In certain embodiments, the invention relates to any one of the aforementioned methods, wherein $R^{22b}$ is methyl.

In certain embodiments, the invention relates to any one of the aforementioned methods, wherein $R^1$ is hydrogen.

In certain embodiments, the invention relates to any one of the aforementioned methods, wherein $R^1$ is alkyl.

In certain embodiments, the invention relates to any one of the aforementioned methods, wherein $R^1$ is —CH$_3$, —CH$_2$CH$_3$, —CH$_2$CH(CH$_3$)$_2$ or —CH$_2$CH$_2$CH(CH$_3$)$_2$.

In certain embodiments, the invention relates to any one of the aforementioned methods, wherein $R^1$ is $C_3$-$C_7$ cycloalkyl.

In certain embodiments, the invention relates to any one of the aforementioned methods, wherein $R^1$ is cyclopropyl, cyclopropylmethyl, 2-cyclopropylethyl, cyclobutyl, cyclobutylmethyl, 2-cyclobutylethyl, cyclopentyl, cyclopentylmethyl, or 2-cyclopentylethyl.

In certain embodiments, the invention relates to any one of the aforementioned methods, wherein $R^1$ is

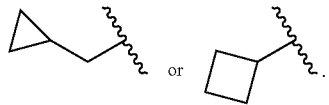 [SMILES: *CC1CC1 ; *C1CCC1]

In certain embodiments, the invention relates to any one of the aforementioned methods, wherein $R^1$ is —CH$_2$CF$_3$.

In certain embodiments, the invention relates to any one of the aforementioned methods, wherein $R^1$ is —CH$_2$Ph.

In certain embodiments, the invention relates to any one of the aforementioned methods, wherein $R^1$ is —C(=O)H.

In certain embodiments, the invention relates to any one of the aforementioned methods, wherein $R^1$ is —C(=O)CH$_3$.

In certain embodiments, the invention relates to any one of the aforementioned compounds, wherein $R^1$ is heterocyclyl or heterocyclylalkyl.

In certain embodiments, the invention relates to any one of the aforementioned compounds, wherein $R^1$ is

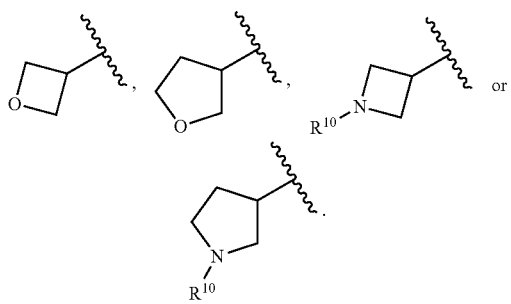

In certain embodiments, the invention relates to any one of the aforementioned methods, wherein $R^1$ is

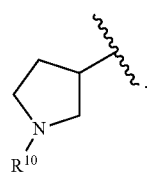

In certain embodiments, the invention relates to any one of the aforementioned compounds, wherein $R^1$ is

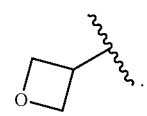

In certain embodiments, the invention relates to any one of the aforementioned methods, wherein $R^1$ is

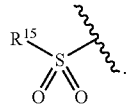

In certain embodiments, the invention relates to any one of the aforementioned methods, wherein $R^{15}$ is alkyl.

In certain embodiments, the invention relates to any one of the aforementioned methods, wherein $R^{15}$ is cycloalkyl.

In certain embodiments, the invention relates to any one of the aforementioned methods, wherein $R^{15}$ is cycloalkylalkyl.

In certain embodiments, the invention relates to any one of the aforementioned methods, wherein $R^1$ is $(C_2\text{-}C_4)$alkyl substituted with

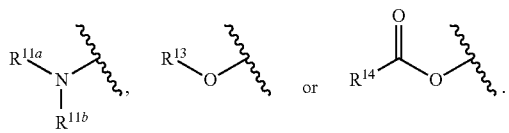

In certain embodiments, the invention relates to any one of the aforementioned methods, wherein $R^1$ is

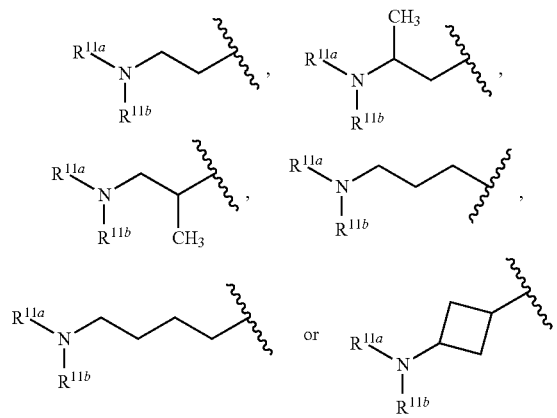

In certain embodiments, the invention relates to any one of the aforementioned methods, wherein $R^{11a}$ is hydrogen, alkyl, or alkyl-cycloalkyl.

In certain embodiments, the invention relates to any one of the aforementioned methods, wherein $R^{11a}$ is hydrogen, methyl, or i-propyl.

In certain embodiments, the invention relates to any one of the aforementioned methods, wherein $R^1$ is

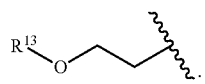

In certain embodiments, the invention relates to any one of the aforementioned methods, wherein $R^{13}$ is hydrogen.

In certain embodiments, the invention relates to any one of the aforementioned methods, wherein $R^1$ is

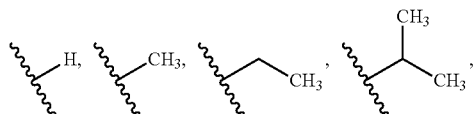

-continued

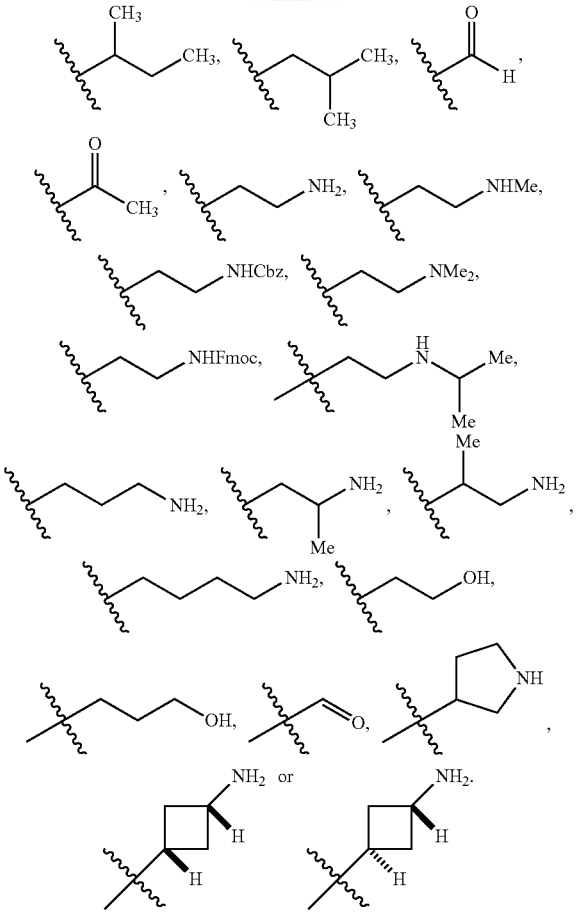

In certain embodiments, the invention relates to any one of the aforementioned methods, wherein A is

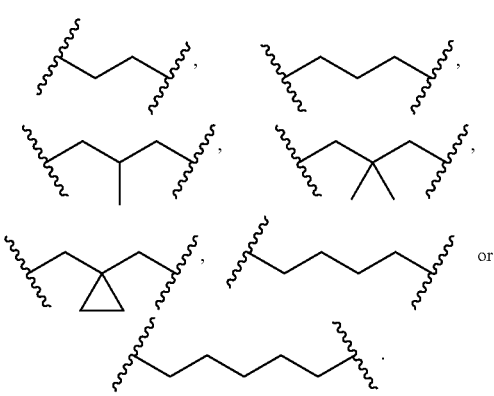

In certain embodiments, the invention relates to any one of the aforementioned methods, wherein A is

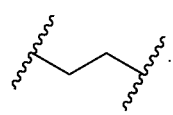 [SMILES: *CC*]

In certain embodiments, the invention relates to any one of the aforementioned methods, wherein A is

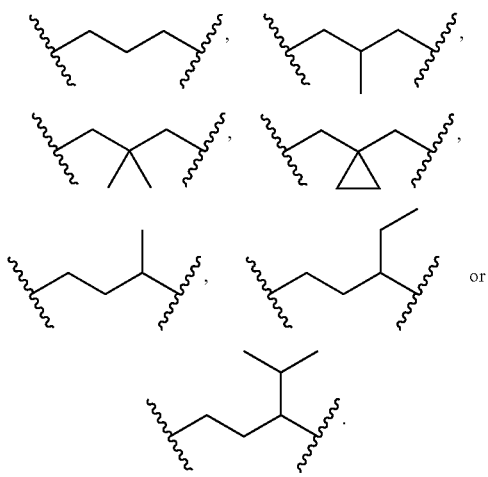

In certain embodiments, the invention relates to any one of the aforementioned methods, wherein A is

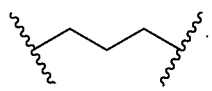

In certain embodiments, the invention relates to any one of the aforementioned methods, wherein A is

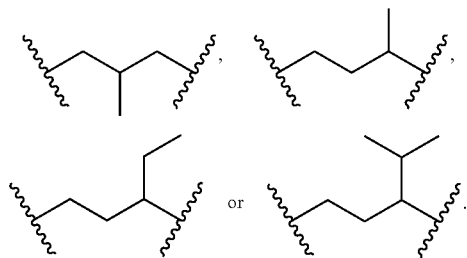

In certain embodiments, the invention relates to any one of the aforementioned methods, wherein A is

In certain embodiments, the invention relates to any one of the aforementioned methods, wherein A is

In certain embodiments, the invention relates to any one of the aforementioned methods, wherein A is

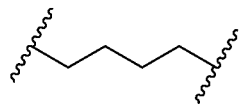

In certain embodiments, the invention relates to any one of the aforementioned methods, wherein A is

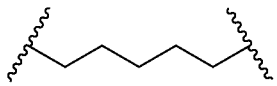

In certain embodiments, the invention relates to any one of the aforementioned methods, wherein A is

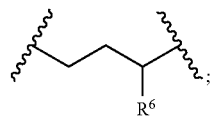

and $R^6$ is alkyl.

In certain embodiments, the invention relates to any one of the aforementioned methods, wherein A is

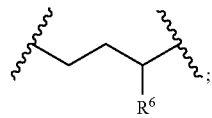

and $R^6$ is methyl, ethyl or isopropyl.

In certain embodiments, the invention relates to any one of the aforementioned methods, wherein $R^3$ is hydroxyl.

In certain embodiments, the invention relates to any one of the aforementioned methods, wherein $R^3$ is hydrogen.

In certain embodiments, the invention relates to any one of the aforementioned methods, wherein $R^4$ is hydroxyl.

In certain embodiments, the invention relates to any one of the aforementioned methods, wherein $R^4$ is hydrogen.

In certain embodiments, the invention relates to any one of the aforementioned methods, wherein $R^{41}$ is hydrogen.

In certain embodiments, the invention relates to any one of the aforementioned methods, wherein $R^{41}$ is methyl.

In certain embodiments, the invention relates to any one of the aforementioned methods, wherein $R^3$ is hydroxyl; and $R^4$ is hydroxyl.

In certain embodiments, the invention relates to any one of the aforementioned methods, wherein $R^3$ is hydroxyl; $R^4$ is hydroxyl; and $R^{41}$ is hydrogen.

In certain embodiments, the invention relates to any one of the aforementioned methods, wherein $R^3$ is hydroxyl; $R^4$ is hydroxyl; and $R^{41}$ is methyl.

In certain embodiments, the invention relates to any one of the aforementioned methods, wherein $R^3$ is hydrogen; and $R^4$ is hydroxyl.

In certain embodiments, the invention relates to any one of the aforementioned methods, wherein $R^3$ is hydrogen; $R^4$ is hydroxyl; and $R^{41}$ is hydrogen.

In certain embodiments, the invention relates to any one of the aforementioned methods, wherein $R^3$ is hydrogen; $R^4$ is hydroxyl; and $R^{41}$ is methyl.

In certain embodiments, the invention relates to any one of the aforementioned methods, wherein $R^3$ is hydroxyl; and $R^4$ is hydrogen.

In certain embodiments, the invention relates to any one of the aforementioned methods, wherein Z is hydrogen or

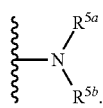

In certain embodiments, the invention relates to any one of the aforementioned methods, wherein Z is hydrogen.

In certain embodiments, the invention relates to any one of the aforementioned methods, wherein Z is

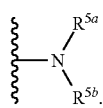

In certain embodiments, the invention relates to any one of the aforementioned methods, wherein $R^{5a}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned methods, wherein $R^{5a}$ is hydrogen, aralkyloxyalkyl, alkyl, aryl, aralkyl, aminoalkyl or hydroalkyl.

In certain embodiments, the invention relates to any one of the aforementioned methods, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH.

In certain embodiments, the invention relates to any one of the aforementioned methods, wherein $R^{5b}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned methods, wherein $R^{5b}$ is hydrogen, aralkyloxyalkyl, alkyl, aryl, aralkyl, aminoalkyl or hydroalkyl.

In certain embodiments, the invention relates to any one of the aforementioned methods, wherein $R^{5b}$ is hydrogen.

In certain embodiments, the invention relates to any one of the aforementioned methods, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH; and $R^{5b}$ is —H.

In certain embodiments, the invention relates to any one of the aforementioned methods, wherein $R^{7a}$ is hydrogen or lower alkyl.

In certain embodiments, the invention relates to any one of the aforementioned methods, wherein $R^{7a}$ is hydrogen.

In certain embodiments, the invention relates to any one of the aforementioned methods, wherein $R^{7b}$ is hydrogen or lower alkyl.

In certain embodiments, the invention relates to any one of the aforementioned methods, wherein $R^{7b}$ is hydrogen.

In certain embodiments, the invention relates to any one of the aforementioned methods, wherein $R^{7c}$ is hydrogen or lower alkyl.

In certain embodiments, the invention relates to any one of the aforementioned methods, wherein $R^{7c}$ is hydrogen.

In certain embodiments, the invention relates to any one of the aforementioned methods, wherein the compound, or a pharmaceutically acceptable salt, hydrate, enantiomer or stereoisomer thereof, is selected from the group consisting of

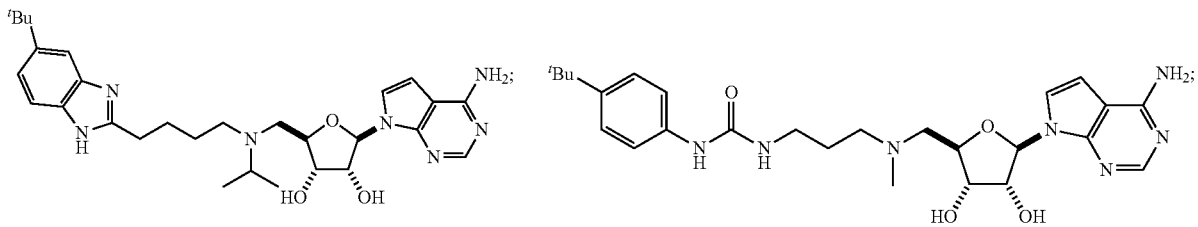

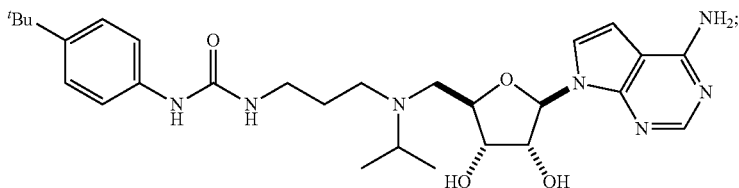

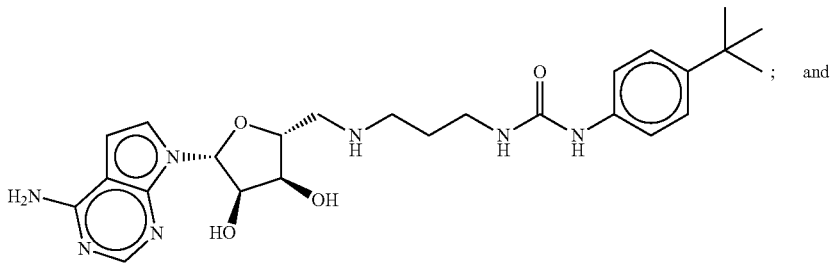

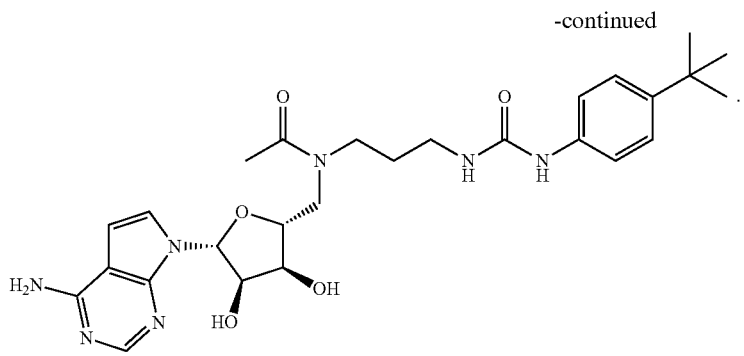

Diseases such as cancers and neurological disease can be treated by administration of modulators of protein (e.g., histone) methylation, e.g., modulators of histone methyltransferase, or histone demethylase enzyme activity. Histone methylation has been reported to be involved in aberrant expression of certain genes in cancers, and in silencing of neuronal genes in non-neuronal cells. Modulators described herein can be used to treat these diseases, i.e., to restore normal methylation states of histones or other proteins to affected cells.

Based at least on the fact that increased histone methylation has been found to be associated with certain cancers, a method for treating cancer in a subject comprises administering to the subject in need thereof a therapeutically effective amount of a compound that decreases methylation or restores methylation to roughly its level in counterpart normal cells. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation, Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth.

Exemplary cancers that may be treated include leukemias, e.g., acute lymphoid leukemia and myeloid leukemia, mixed lineage leukemia and carcinomas, such as colorectal carcinoma and hepatocarcinoma. Other cancers include Acute Lymphoblastic Leukemia; Acute Lymphoblastic Leukemia; Acute Myeloid Leukemia; Acute Myeloid Leukemia; Adrenocortical Carcinoma Adrenocortical Carcinoma; AIDS-Related Cancers; AIDS-Related Lymphoma; Anal Cancer: Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor. Ependymoma; Brain Tumor, Medulloblastoma; Brain Tumor, Supratentoria I Primitive Neuroectodermal Tumors; Brain Tumor, Visual Pathway and Hypothalamic Glioma; Brain Tumor; Breast Cancer; Breast Cancer and Pregnancy; Breast Cancer; Breast Cancer, Male; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cerebral Astrocytoma/Malignant Glioma; Cervical Cancer; Childhood Cancers; Chronic Lymphocytic Leukemia; Chronic Myelogenous Leukemia; Chronic Myeloproliferative Disorders; Colon Cancer; Colorectal Cancer; Cutaneous T-Cell Lymphoma, see Mycosis Fungoides and Sezary Syndrome; Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's; Lymphoma, Hodgkin's During Pregnancy; Lymphoma, Non-Hodgkin's; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer; Neuroblastoma; Non-Hodgkin's Lymphoma; Non-Hodgkin's Lymphoma; Non-Hodgkin's Lymphoma During Pregnancy; Non-Small Cell Lung Cancer; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Unknown Primary Site, Carcinoma of; Unknown Primary Site, Cancer of; Unusual Cancers of Childhood; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SB MA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by DOT1, plays a role may be treatable or preventable using compounds and methods described herein.

Combination Therapy

In one aspect of the invention, a compound of the invention, or a pharmaceutically acceptable salt thereof, can be used in combination with another therapeutic agent to treat diseases such cancer and/or neurological disorders. For example, the additional agent can be a therapeutic agent that is art-recognized as being useful to treat the disease or condition being treated by the compound of the present invention. The additional agent also can be an agent that imparts a beneficial attribute to the therapeutic composition (e.g., an agent that affects the viscosity of the composition).

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

The agents set forth below are for illustrative purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, one aspect of the invention relates to the use of a compound of the invention (e.g., those of formula I) in combination with another anticancer agent, e.g., a compound that effects histone modifications, such as an HDAC inhibitor, for the treatment of cancer and/or a neurological disorder. In certain embodiments, the other anticancer agent is selected from the group consisting of chemotherapetics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®) biologics (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™) corticosteroids, (such as dexamethasone sodium phosphate, DeltaSone® and Delta-Cortef®), hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®) and radiopharmaceuticals (such as Iodotope®, Metastron®, Phosphocol® and Samarium SM-153).

Dosage

As used herein, a "therapeutically effective amount" or "therapeutically effective dose" is an amount of a compound of the invention or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount may be determined by methods known to those of skill in the art.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. Dosage may also be guided by monitoring compound effects on pharmacodynamic markers of enzyme inhibition (e.g., histone methylation or target gene expression) in diseased or surrogate tissue. Cell culture or animal experiments can be used to determine the relationship between doses required for changes in pharmacodynamic markers and doses required for therapeutic efficacy can be determined in cell culture or animal experiments or early stage clinical trials. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the methyltransferase modulating effects, or minimal effective concentration (MEC) for the required period of time to achieve therapeutic efficacy. The MEC will vary for each compound but can be estimated from in vitro data and animal experiments. Dosages necessary to achieve the MEC will depend on individual characteristics and route of administration. However, HPLC assays or bioassays can be used to determine plasma concentrations.

Dosage intervals can also be determined using the MEC value. In certain embodiments, compounds should be administered using a regimen which maintains plasma levels above the MEC for 10-90% of the time, preferably between 30-90% and most preferably between 50-90% until the desired amelioration of symptoms is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and the amount of composition administered will, of course, be dependent on the subject being treated, on the subject's weight, the severity of the affliction, the manner of administration and the judgment of the prescribing physician.

Kits

The compounds and compositions of the invention (e.g., compounds and compositions of formula I) may, if desired, be presented in a kit (e.g., a pack or dispenser device) which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Instructions for use may also be provided.

Assessment of Activity of Compounds

DOT1L polypeptides and nucleic acids can be used to screen for compounds that bind to and/or modulate (e.g., increase or decrease) one or more biological activities of DOT1L, including but not limited to H3K79 HMTase activity, SAM binding activity, histone and/or nucleosome binding activity, AF10 binding activity, AF10-MLL or other MLL fusion protein binding activity, and/or any other biological activity of interest. A DOT1L polypeptide can be a functional fragment of a full-length DOT1L polypeptide or functional equivalent thereof, and may comprise any DOT1 domain of interest, including but not limited to the catalytic domain, the SAM binding domain and/or the positively charged domain, the AF10 interaction domain and/or a nuclear export signal.

Methods of assessing DOT1L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1L H3K79 HMTase activity can be verified by: contacting a DOT1L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

Any compound of interest can be screened according to the present invention. Suitable test compounds include small organic compounds. Small organic compounds include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof.

DEFINITIONS

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "hydrate" refers to a pharmaceutically acceptable form of a specified compound, with one or more water molecules, that retains the biological effectiveness of such compound.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e., six carbons or less). For example "lower alkyl" refers to an alkyl group containing 1-6 carbons, and "lower alkenyl" refers to an alkenyl group containing 2-6 carbons.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing $4n+2$ electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic hydrocarbon radical containing from 1 to 20 carbon atoms. In one embodiment the term "alkyl" refers to an aliphatic hydrocarbon radical containing from 1 to 15 carbon atoms. In one embodiment the term "alkyl" refers to an aliphatic hydrocarbon radical containing from 1 to 10 carbon atoms. In one embodiment the term "alkyl" refers to an aliphatic hydrocarbon radical containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, 1-(1-ethylcyclopropyl)ethyl and 1-cyclohexylethyl.

The term "cycloalkyl" refers to a cyclic hydrocarbon radical containing from 3 to 15 carbon atoms. In one embodiment the term "cycloalkyl" refers to a cyclic hydrocarbon radical containing from 3 to 10 carbon atoms. In one embodiment the term "cycloalkyl" refers to a cyclic hydrocarbon radical containing from 3 to 7 carbon atoms. Representative examples of cycloalkyl include, but are not limited to, cyclopropyl and cyclobutyl.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene," is art-recognized, and as used herein pertains to a diradical obtained by removing two hydrogen atoms of an alkyl group, as defined above.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein refers to a radical of a non-aromatic, ring system, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydropyranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fiuoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fiuoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fiuoroalkoxysulfonyloxy, alkenyloxysulfonyloxy, alkynyloxysulfonyloxy, alkylsulfinyloxy, haloalkylsulfinyloxy, fiuoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "aryl," as used herein means a phenyl, naphthyl, phenanthrenyl, or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "arylene," is art-recognized, and as used herein pertains to a diradical obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-yl-ethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-methoxyphenyl)pyridinyl.

The term "fused bicyclyl" as used herein means the radical of a bicyclic ring system wherein the two rings are ortho-fused, and each ring, contains a total of four, five, six or seven atoms (i.e. carbons and heteroatoms) including the two fusion atoms, and each ring can be completely saturated, can contain one or more units of unsaturation, or can be completely unsaturated (e.g., in some case, aromatic). For the avoidance of doubt, the degree of unsaturation in the fused bicyclyl does not result in an aryl or heteroaryl moiety.

The term "heteroaryl" as used herein include radicals of aromatic ring systems, including, but not limited to, monocyclic, bicyclic and tricyclic rings, which have 3 to 12 atoms including at least one heteroatom, such as nitrogen, oxygen, or sulfur. For purposes of exemplification, which should not be construed as limiting the scope of this invention: aminobenzimidazole, benzimidazole, azaindolyl, benzo[b]thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g., methylene).

The term "heteroarylene," is art-recognized, and as used herein pertains to a diradical obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein some or all of the hydrogens are replaced with fluorines.

The term "haloalkylene," as used herein pertains to diradical obtained by removing two hydrogen atoms of an haloalkyl group, as defined above.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethyl-phenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenyl carbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy" are likewise defined.

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" or "phosphine" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H₃Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

The term "treating" as used herein, encompasses the administration and/or application of one or more compounds described herein, to a subject, for the purpose of providing prevention of or management of, and/or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" for purposes of treatment includes any human or animal subject who has been diagnosed with, has symptoms of or is at risk of developing a disorder. For methods of prevention the subject is any human or animal subject. To illustrate, for purposes of prevention, a subject may be a human subject who is at risk of or is genetically predisposed to obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds described herein are also useful for veterinary treatment of mammals, including companion animals and farm animals, such as, but not limited to dogs, cats, horses, cows, sheep, and pigs.

Except as otherwise indicated, standard methods can be used for the production of recombinant and synthetic polypeptides, fusion proteins, antibodies or antigen-binding fragments thereof, manipulation of nucleic acid sequences, production of transformed cells, and the like. Such techniques are known to those skilled in the art. See, e.g., Sambrook et al., *Molecular Cloning: A Laboratory Manual* 2nd Ed. (Cold Spring Harbor, N.Y., 1989); F. M. Ausubel et al., *Current Protocols in Molecular Biology* (Green Publishing Associates, Inc. and John Wiley & Sons, Inc., New York).

The term "DOT1L polypeptide" encompasses functional fragments of the full-length polypeptides and functional equivalents of either of the foregoing that have substantially similar or substantially identical amino acid sequences (at least about 75%, 80%, 85%, 90%, 95% 98% or more amino acid sequence similarity or identity), where the functional fragment or functional equivalent retains one or more of the functional properties of the native polypeptide.

By "functional" it is meant that the polypeptide (or nucleic acid) has the same or substantially similar activity with respect to one or more of the biological properties of the native polypeptide (or nucleic acid), e.g., at least about 50%, 75%, 85%, 90%, 95% or 98% or more of the activity of the native polypeptide (or nucleic acid).

The term "modulate" (and grammatical equivalents) refers to an increase or decrease in activity. In particular embodiments, the term "increase" or "enhance" (and grammatical equivalents) means an elevation by at least about 25%, 50%, 75%, 2-fold, 3-fold, 5-fold, 10-fold, 15-fold, 20-fold or more. In particular embodiments, the terms "decrease" or "reduce" (and grammatical equivalents) means a diminishment by at least about 25%, 40%, 50%, 60%, 75%, 80%, 85%, 90%, 95%, 98% or more. In some embodiments, the indicated activity, substance or other parameter is not detectable. Specifically provided are inhibitors of DOT1L.

The term "pharmacodynamic marker" refers to a molecular marker of drug response that can be measured in patients receiving the drug. The marker should be a direct measure of modulation of the drug target and be able to show quantitative changes in response to dose. A potential pharmacodynamic marker for a DOT1L inhibitor could be levels of histone H3K79 methylation in disease or surrogate tissue.

Exemplification

The invention now being generally described, it will be more readily understood by reference to the following examples, which are included merely for purposes of illustration of certain aspects and embodiments of the present invention, and are not intended to limit the invention.

| ABBREVIATIONS | |
|---|---|
| Abbreviation | Definition |
| AA | ammonium acetate |
| Ac | acetyl |
| ACN | acetonitrile |
| AcOH | acetic acid |
| atm | atmosphere |
| Bn | benzyl |
| BOC | tert-butoxy carbonyl |
| BOP | (benzotriazol-1-yloxy)tris(dimethylamino)phosphonium hexafluorophosphate |
| Cbz | benzyloxy carbonyl |
| COMU | (1-Cyano-2-ethoxy-2-oxoethylidenaminooxy)dimethylamino-morpholino-carbenium hexafluorophosphate |
| d | days |
| DBU | 1,8-diazabicyclo[5.4.0]undec-7-ene |
| DCE | 1,2 dichloroethane |
| DCM | dichloromethane |
| DEAD | Diethyl azodicarboxylate |
| DIAD | Diisopropyl azodicarboxylate |
| DiBAL-H | di-isobutyl aluminum hydride |
| DIPEA | N,N-diisopropylethylamine (Hunig's base) |
| DMAP | N,N-dimethyl-4-aminopyridine |

-continued

ABBREVIATIONS

| Abbreviation | Definition |
| --- | --- |
| DMB | 2,4 dimethoxy benzyl |
| DMF | dimethylformamide |
| DMSO | Dimethyl sulfoxide |
| DPPA | Diphenylphosphonic azide |
| EA or EtOAc | Ethyl acetate |
| EDC or EDCI | N-(3-Dimethylaminopropyl)-N'-ethylcarbodiimide |
| ELS | Evaporative Light Scattering |
| ESI− | Electrospray negative mode |
| ESI+ | Electrospray positive mode |
| $Et_2O$ | diethyl ether |
| $Et_3N$ or TEA | triethylamine |
| EtOH | ethanol |
| FA | formic acid |
| FC | Flash chromatography |
| h | hours |
| $H_2O$ | water |
| HATU | O-(7-Azabenzotriazol-1-yl)-N,N,N',N'-tetramethyluronium hexafluorophosphate |
| HCl | hydrochloric acid |
| HOAT | 1-Hydroxy-7-azabenzotriazole |
| HOBt | 1-Hydroxybenzotriazole |
| HO-Su | N-Hydroxysuccinimide |
| HPLC | High performance liquid chromatography |
| KHMDs | Potassium hexamethyldisilazide |
| LC/MS or LC-MS | liquid chromatography mass spectrum |
| LDA | Lithium diisopropylamide |
| LG | leaving group |
| LiHMDs | Lithium hexamethyldisilazide |
| M | Molar |
| m/z | mass/charge ratio |
| m-CPBA | meta-chloroperbenzoic acid |
| MeCN | Acetonitrile |
| MeOD | $d_4$-methanol |
| MeOH | methanol |
| $MgSO_4$ | magnesium sulfate |
| min | minutes |
| MS | Mass Spectrometry |
| Ms | Mesyl |
| MS | mass spectrum |
| MsCl | Mesyl chloride |
| MsO | Mesylate |
| MWI | microwave irradiation |
| $Na_2CO_3$ | sodium carbonate |
| $NaHCO_3$ | sodium bicarbonate |
| NaHMDs | Sodium hexamethyldisilazide |
| NaOH | sodium hydroxide |
| NIS | N-iodosuccinimide |
| NMR | Nuclear Magnetic Resonance |
| o/n or O/N | overnight |
| PE | Petroleum Ether |
| PG | protecting group |
| PMB | para methoxybenzyl |
| PPAA | 1-Propanephosphonic acid cyclic anhydride |
| ppm | parts per million |
| prep HPLC | preparative High performance liquid chromatography |
| prep TLC | preparative thin layer chromatography |
| p-TsOH | para-toluenesulfonic acid |
| rt or RT | room temperature |
| SEM | 2-(Trimethylsilyl)ethoxymethyl |
| SEMCl | -(Trimethylsilyl)ethoxymethyl chloride |
| SFC | Super critical chromatography |
| SGC | silica gel chromatography |
| STAB | Sodium triacetoxy borohydride |
| TBAF | tetra-n-butylammonium fluoride |
| TFA | trifluoroacetic acid |
| TfO | triflate |
| THF | tetrahydrofuran |
| THP | tetrahydropyran |
| TLC | thin layer chromatography |
| Ts | tosyl |
| TsOH | tosic acid |
| UV | ultraviolet |

General Methods

Cell Culture.

Human Leukemia cell lines THP-1, RS4; 11, and MV4-11 were obtained from ATCC, MOLM-13 cells were obtained from DSMZ. All lines were grown in RPMI 1640 containing 10% FBS and maintained using the vendors recommended cell densities and environmental conditions. Media was supplemented with non essential amino acids and L-Glutamine. THP-1 cells were also supplemented with 0.05 mM β-Mercaptoethanol.

Methylation Analysis.

Cells were seeded at $5 \times 10^5$ cells/mL in a 12 well plate at a final volume of 2 mLs. Cells were dosed with compounds to the appropriate concentration from a 50 mM DMSO stock solution. Compound and media were refreshed every two days over the course of seven day incubation by counting cells using trypan blue exclusion (Vicell), pelleting at 200 g for 5 minutes and resuspending in fresh media containing compound at a final cell concentration of $5 \times 10^5$ cells/mL. Following compound incubation, histones were extracted from $1 \times 10^6$ cells using a commercial histone extraction kit (Active Motif). Purified histones were quantitated using the BCA protein assay (Pierce) with a BSA standard curve. 400 ng of isolated histones were fractionated by SDS-PAGE on a 4-20% gel and transferred to nitrocellulose membranes. Membranes were incubated with various primary and secondary antibodies and imaged on the Licor imaging system (Odyssey). The H3K79-Me2 rabbit polyclonal was purchased from Abeam. Other rabbit polyclonal antibodies including H3K4-Me3, H3K9-Me3, H3K27-Me2, and H3K27-Me3 were purchased from Cell Signaling Technologies (CST). A mouse monoclonal total H3 antibody was used as a loading control (CST). Fluorescently labeled secondary antibodies were purchased from Odyssey.

Cell Growth and Viability Analysis.

Cells were harvested from exponentially growing cell cultures and seeded at $3 \times 10^4$ cells per well. Samples were maintained in a 96 well black walled clear bottom plate (Corning). A final concentration of 50 uM compound in 0.2% DMSO was added to the appropriate wells on Day 0. Treatment of MV4-11 and MOLM-13 lasted 14 days, while THP-1 cells were treated for 18 days. Compound and media were replaced every two days during incubation by transferring samples to a V-bottom plate (Corning), spinning at 200 g for 5 minutes in a room temperature rotor, resuspending in fresh media containing compound and transferring back to the assay plate. Cells were counted periodically using the Guava Viacount assay and read on the EasyCyte Plus instrument (Millipore). Assay plates were split when necessary to within recommended cell densities. Final cell counts were adjusted to take cell splits into account and reported as total viable cells/well HOXA9 (qPCR).

Cells were treated with compound for 7 days similar to methylation assay. Cell were pelleted at 200 g in a room temperature rotor and total RNA isolated using the Qiagen RNeasy kit. RNA concentration and quality was determined by using the Nanovue (GE Healthcare). Total RNA was reverse transcribed using a high capacity cDNA reverse transcription kit (Applied Biosystems). A predesigned labeled primer set for HOXA9 was purchased from Applied Biosystems. qPCR reactions contained 50 ng cDNA, 1× labeled primer and 1× Taqman universal PCR master mix (Applied Biosystems). Samples were run on a 7900 HT Fast Real Time PCR machine (Applied Biosystems) with PCR conditions of 2 min 50° C., 10 min 95° C., 40 cycles at 15 sec 95° C. and 1 min 60° C. HOXA9 cycle numbers were normalized to the house keeping gene B2 microglobulin (B2M predesigned control from Applied Biosystems). Percent of DMSO control was calculated with the equation, percent control= $(2^{\wedge-\Delta\Delta CT})*100$ where the ΔΔCT is the difference between normalized HOXA9 sample and control (ΔCT sample−ΔCT control=ΔΔCT).

Determination of $IC_{50}$.

Compound was serially diluted 3 fold in DMSO for 10 points and 1 μl was plated in a 384 well microtiter plate. Positive control (100% inhibition standard) was 2.5 uM final concentration of S-adenosyl-L-homocysteine and negative control (0% inhibition standard) contained 1 μl of DMSO. Compound was then incubated for 30 minutes with 40 μl per well of DOT1L(1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 μl per well of substrate mix (same assay buffer with 200 nM S-[methyl-$^3$H]-adenosyl-L methionine, 600 nM of unlabeled S-[methyl-$^3$H]-adenosyl-L methionine, and 20 nM oligonucleosome) was added to initiate the reaction. Reaction was incubated for 120 minutes at room temperature and quenched with 10 μl per well of 100 μM S-methyl-adenosyl-L methionine. For detection, substrate from 50 μl of reaction was immobilized on a 384 well Streptavidin coated Flashplate (Perkin Elmer) (also coated with 0.2% polyethyleneimine) and read on a Top Count scintillation counter (Perkin Elmer).

General Synthetic Schemes

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Scheme 1

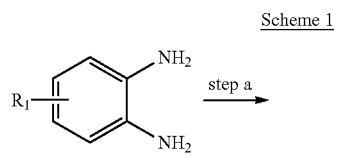

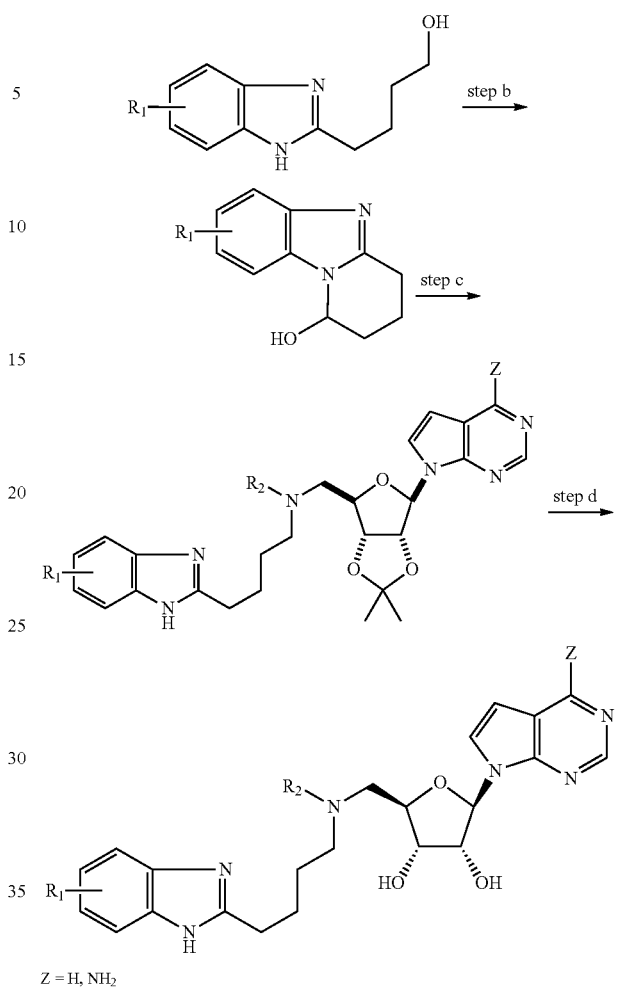

Z = H, NH₂

Scheme 1 shows the synthesis of modified deazapurine analogs following a general route that utilizes well-established chemistry. Condensation of and tetrahydropyran-2-one with an appropriately substituted diaminobenzene derivative would provide the benzimidazole (step a). Oxidation with a suitable reagent like IBX in ethyl acetate would give the modified benzimidazole (step b). Reductive amination with the amine using sodium acetoxyborohydride in dichloroethane would give coupled product (step c). Removal of the acetonide protecting group under acidic conditions using HCl in MeOH would give the desired diol (step d).

Scheme 2

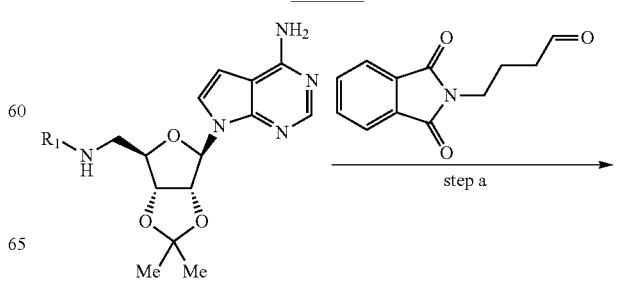

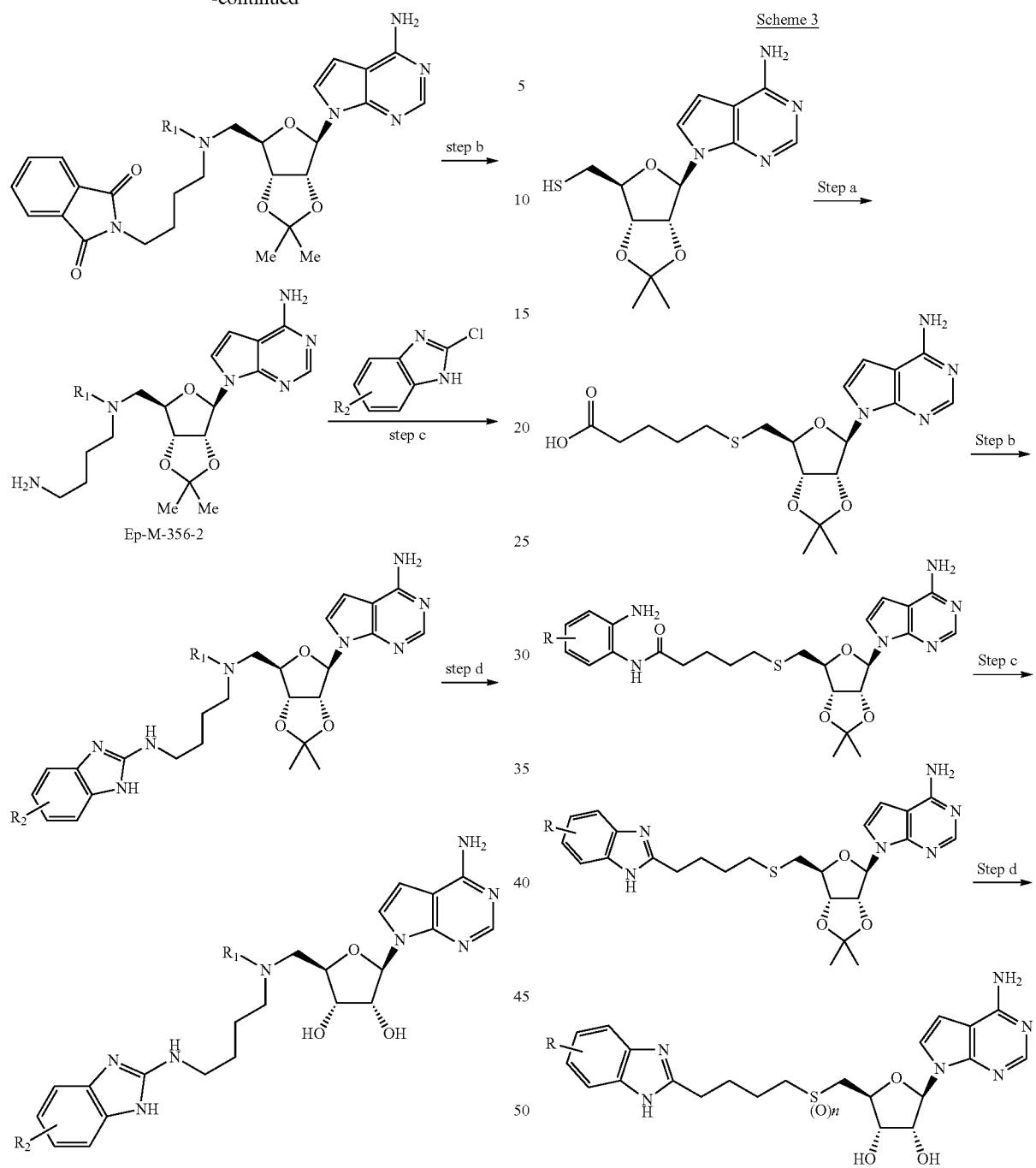

Scheme 2 details a synthesis of related deazapurine analogs containing an aminobenzamidazole moiety. Condensation of an amine with 4-(1,3-dioxoisoindolin-2-yl)butanal using sodium acetoxyborohydride in dichloroethane would give the protected amine (step a). Removal of the amine protecting group would be accomplished by treating this intermediate with hydrazine in refluxing ethanol and would give the free amine (step b). Condensation of the amine with an appropriately substituted 2-chlorobenzamidazole at elevated temperature in tert-butanol would give the desired aminobenzimidazole (step c). Removal of the acetonide protecting group under acidic conditions using HCl in MeOH would give the desired diol (step d).

Scheme 3 details a synthesis of related deazapurine analogs containing an amino-benzimidazole moiety with a sulfur containing linker. The starting thiol would be modified with an appropriate halo ester using a mild base like $K_2CO_3$ in a polar solvent like acetone to give the thioester that would be then saponified with a strong base like LiOH in a polar solvent like MeOH to give the desired acid (Step a). The acid would be coupled with an appropriate diamine using standard amide coupling conditions to give the desired amino amide (Step b). The amino amide would be cyclized to the benzimidazole using a mild acid like acetic acid as a reagent and solvent to give the benzimidazole (Step c). The oxidation state of the sulfur atom would be adjusted (n=0-2) with a variety of selective oxidation reagents like m-CPBA followed by removal of the acetonide protecting group by treatment with a strong acid like HCl in a polar solvent like MeOH to give the final product (Step d).

Scheme 4

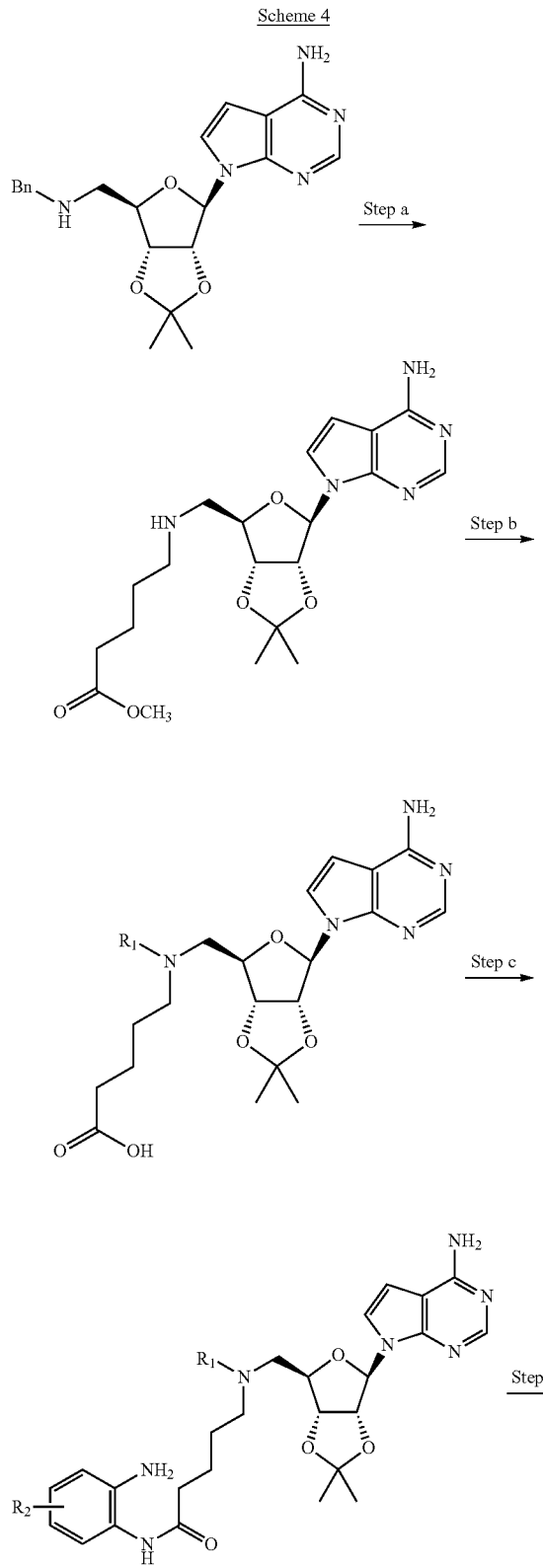

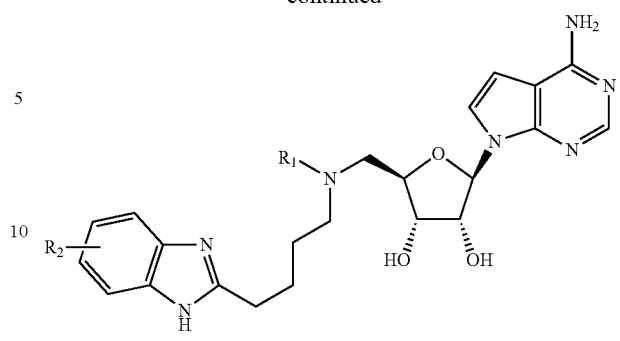

Scheme 4 details a synthesis of related deazapurine analogs containing an aminobenzimidazole moiety with a substituted amine containing linker. The benzyl protected amine would be alkylated with an appropriate halo ester in the presence of a mild base like $K_2CO_3$ in a polar solvent like acetone to give the desired ester that would be subjected to catalytic hydrogenation using hydrogen gas and an appropriate catalyst like palladium on carbon in a polar solvent like EtOH to give the free amine (Step a). A variety of substituents ($R_1$) would be introduced using either reductive amination conditions or alkylation conditions to give the $R_1$ substituted amine. The ester would be then hydrolyzed with a strong base like LiOH in a polar solvent like MeOH to give the acid (Step b). The acid would be coupled with an appropriate diamine using standard amide coupling conditions to give the desired amino amide (Step c). The amino amide would be cyclized to the benzimidazole using a mild acid like acetic acid as a reagent and solvent to give the benzimidazole and the acetonide protecting group would be removed using a strong acid like HCl in a polar solvent like MeOH to give the final product (Step d).

Scheme 5

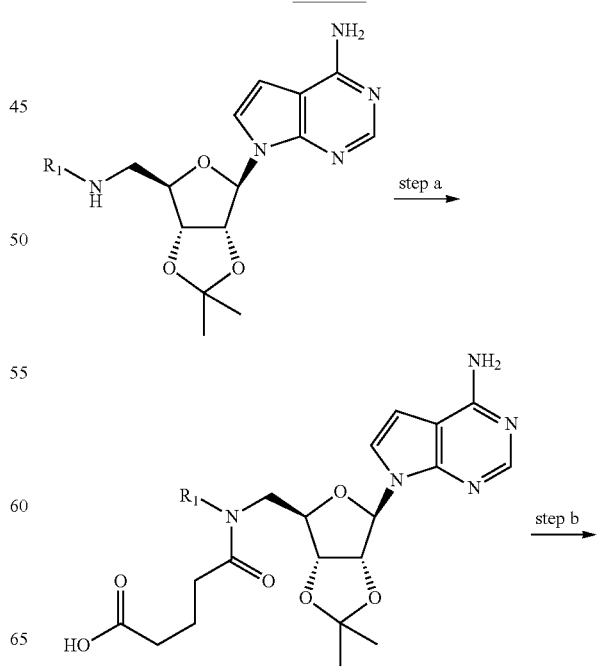

-continued

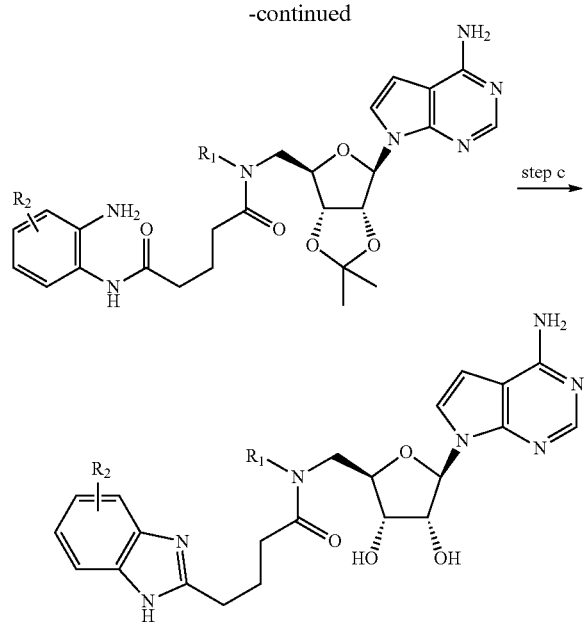

Scheme 5 details a synthesis of related deazapurine analogs containing an aminobenzimidazole moiety with a substituted amide containing linker. Starting with the amine that was previously described in Scheme 2 and treating with an appropriately substituted acid ester under standard amide coupling conditions would give the amide ester that would be hydrolyzed using a strong base like LiOH in a polar solvent like MeOH to give the acid (step a). The acid would be coupled with an appropriate diamine using standard amide coupling conditions to give the desired amino amide (step b). The amino amide would be cyclized to the benzimidazole using a mild acid like acetic acid as a reagent and solvent to give the benzimidazole and the acetonide protecting group would be removed using a strong acid like HCl in a polar solvent like MeOH to give the final product (Step c).

Preparation of Compounds 8 and 9

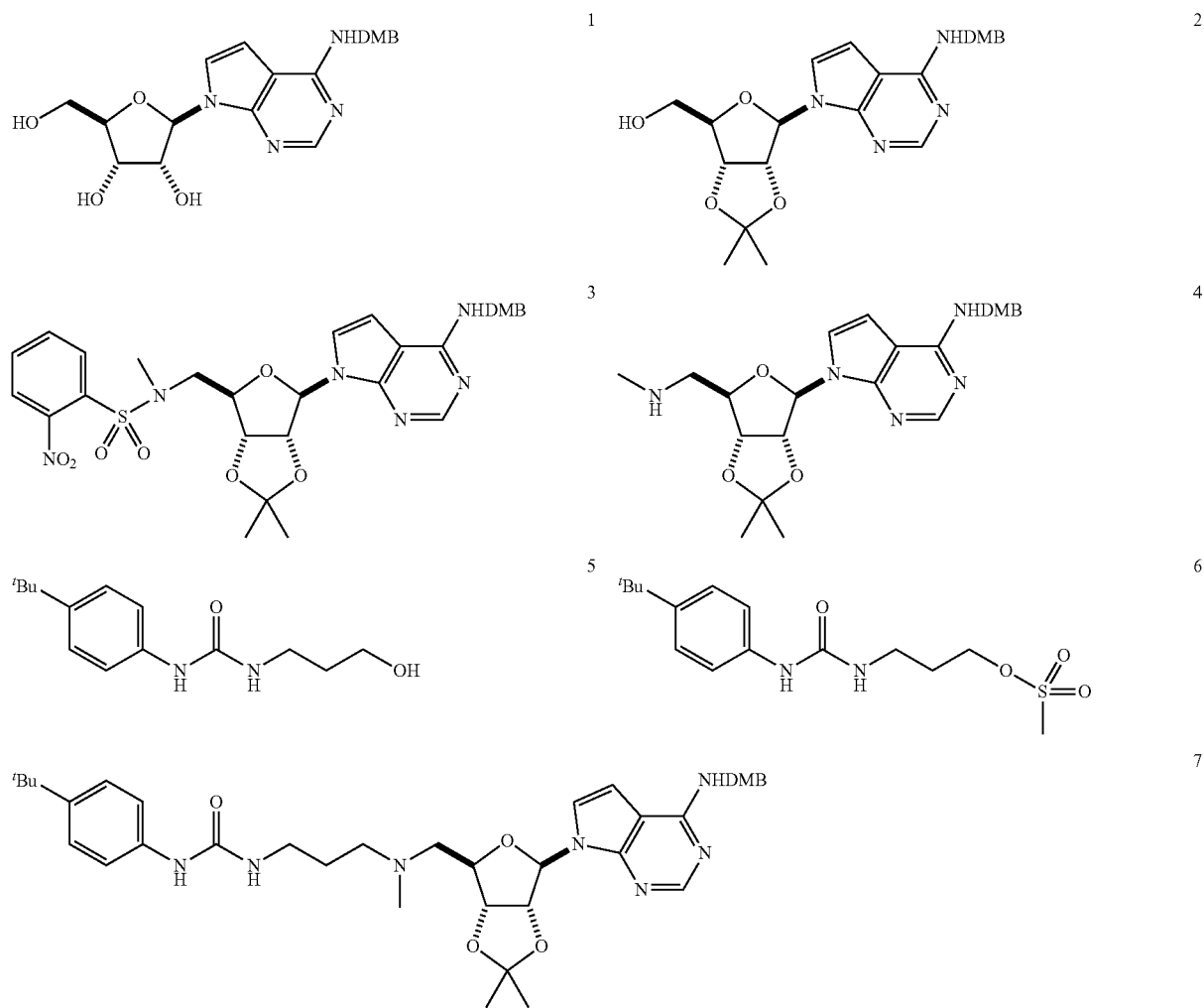

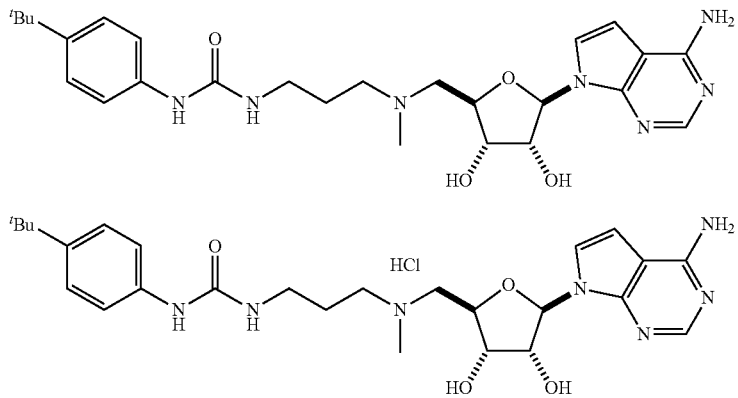

Figure 3:
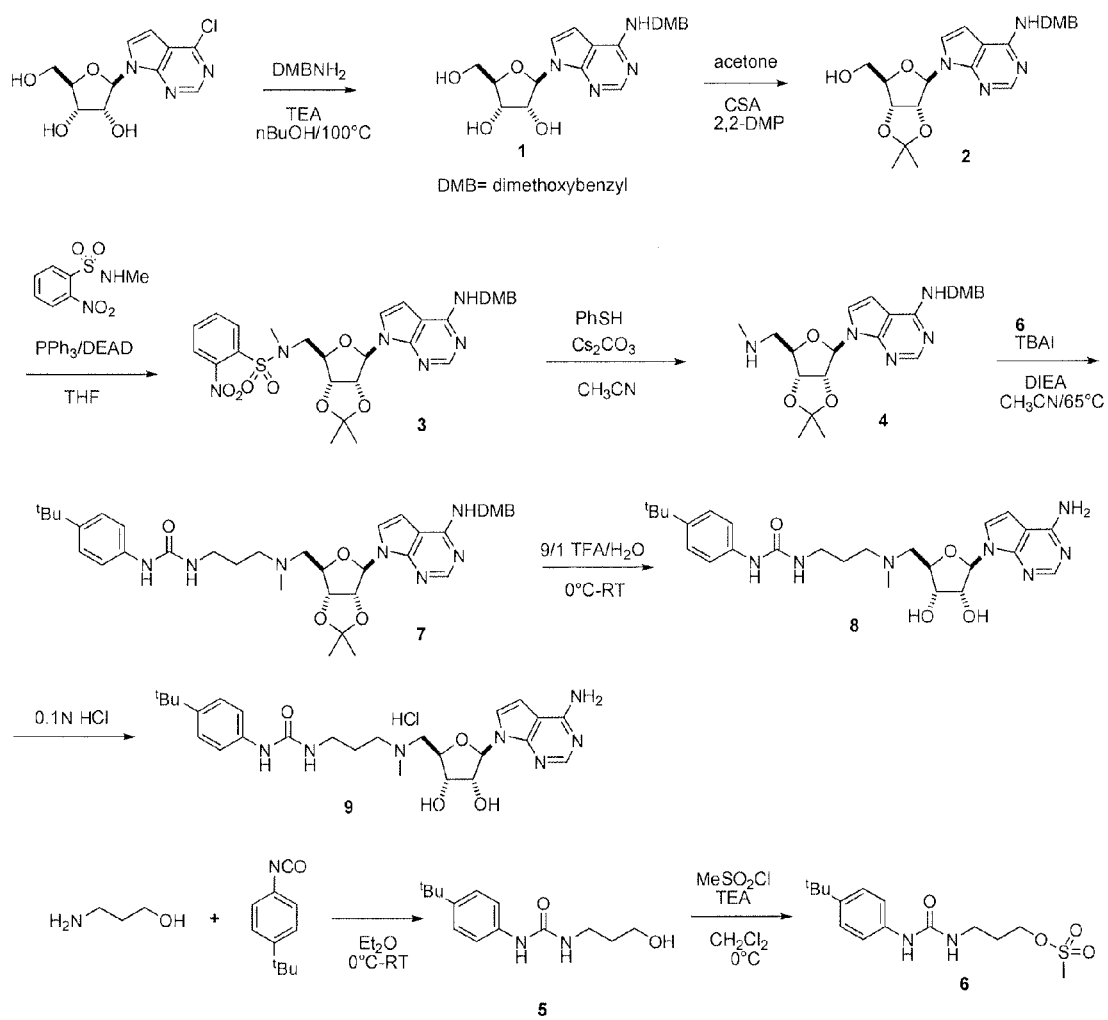
FIG. 3 depicts a route to compound 8 and its hydrochloride salt 9.

The following steps are graphically depicted in FIG. 3.

Step 1: (2R,3R,4S,5R)-2-(4-((2,4-dimethoxybenzyl)amino)-7H-pyrrolo[2,3-d]pyrimidin-7-yl)-5-(hydroxymethyl)tetrahydrofuran-3,4-diol A suspension of 7-chloro tubercidin (1.67 g, 5.84 mmol) in 1-butanol (16.0 mL) was treated with N,N-diisopropylethylamine (1.22 mL, 7.01 mmol) and 1-(2,4-dimethoxyphenyl)methanamine (1.05 mL, 7.01 mmol) and heated at 100-110° C. overnight. After 20 h, LCMS indicated a new product had formed and the starting material was consumed. The mixture was cooled to room temperature and the solvent removed under high vacuum. The material was purified by flash chromatography (200 g silica gel; 5-10% MeOH/CH$_2$Cl$_2$) to yield the title compound (2.19 g, 90%) as a foam: MS (ESI+) for C$_{20}$H$_{24}$N$_4$O$_6$ m/z 417.1 (M+H)$^+$.; (ESI−) for C$_{20}$H$_{24}$N$_4$O$_6$ m/z 415.2 (M−H)$^-$; HPLC purity 97% (ret. time, 2.41 min).

Step 2: ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol A solution of (2R,3R,4S,5R)-2-(4-((2,4-dimethoxybenzyl)amino)-7H-pyrrolo[2,3-d]pyrimidin-7-yl)-5-(hydroxymethyl)tetrahydrofuran-3,4-diol (3.30 g, 7.45 mmol) in acetone (76.5 mL) and 2,2-dimethoxypropane (16.5 mL, 134 mmol) was treated with 10-camphorsulfonic acid (1.73 g, 7.44 mmol) in one portion and the reaction was allowed to stir at room temperature. After 1 h, all SM was consumed by HPLC. The reaction was quenched by the addition of sodium bicarbonate (1.88 g, 22.3 mmol) and the reaction mixture was stirred for 30 minutes during which time a precipitate formed. The reaction mixture was partitioned between 200 mL CHCl$_3$ and 75 mL H$_2$O. The mixture was diluted with 15 mL brine, extracted and the phases separated. The aqueous phase was washed twice with 50 mL portions of CHCl$_3$ and the combined organic phase was dried over Na$_2$SO$_4$. The solution was filtered and concentrated to yield a foam. The crude product was taken up in methanol (130 mL, 3200 mmol) and treated with p-toluenesulfonic acid monohydrate (1.27 g, 6.70 mmol) in one portion. The mixture was stirred at room temperature for 2 h upon which time the reaction mixture was quenched with sodium bicarbonate (1.88 g, 22.3 mmol) and the mixture was stirred for 30 minutes. The solvent was removed in vacuo and the residue partitioned between 50 mL H$_2$O and 150 mL CH$_2$Cl$_2$ and extracted. The organic phase was washed with 50 mL sat NaHCO$_3$, dried over Na$_2$SO$_4$, filtered and concentrated to yield a foam. The product was isolated by flash chromatography (120 g silica gel, 60-80% EA/hept) to yield the title compound (2.83 g, 83%) as a light yellow stiff foam: MS (ESI+) for C$_{23}$H$_{28}$N$_4$O$_6$ m/z 457.4 (M+H)$^+$; (ESI−) for C$_{23}$H$_{28}$N$_4$O$_6$ m/z 455.2 (M−H)$^-$; HPLC purity 99% (ret. time, 3.08 min).

Step 3: N-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N-methyl-2-nitrobenzenesulfonamide A solution of ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol (1.52 g, 3.33 mmol) and triphenylphosphine (1.92 g, 7.32 mmol) in tetrahydrofuran (25 mL) was cooled at 0° C. and treated dropwise with diethyl azodicarboxylate (1.26 mL, 7.99 mmol). The now yellow solution was treated dropwise with a solution of N-methyl-2-nitrobenzenesulfonamide (1.01 g, 4.66 mmol) in tetrahydrofuran (9.9 mL, 120 mmol) over ~5 minutes and the solution was allowed to stir and slowly warm up to room temperature. After 24 h at room temperature, HPLC indicated that the starting material had been consumed. The reaction mixture was partially concentrated and the solution was purified by flash chromatography (175 g silica gel, 60-90% EA/hept) to yield the title compound (0.82 g, 38%) as a light yellow glass: MS (ESI+) for C$_{30}$H$_{34}$N$_6$O$_9$S m/z 655.3 (M+H)$^+$; (ESI−) for C$_{30}$H$_{34}$N$_6$O$_9$S m/z 653.3 (M−H)$^-$; HPLC purity 68% (ret. time, 3.94 min).

Step 4: N-(2,4-dimethoxybenzyl)-7-((3aR,4R,6R,6aR)-2,2-dimethyl-6-((methylamino)methyl)tetrahydrofuro[3,4-d][1,3]dioxol-4-yl)-7H-pyrrolo[2,3-d]pyrimidin-4-amine A suspension of N-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N-methyl-2-nitrobenzenesulfonamide (0.82 g, 1.2 mmol) and cesium carbonate (0.82 g, 2.5 mmol) in acetonitrile (23 mL, 440 mmol) was degassed by sparging with nitrogen gas for 10 minutes. The solution was treated dropwise with benzenethiol (0.26 mL, 2.5 mmol) and the mixture was allowed to stir at room temperature overnight. After 22 h, LCMS indicated the reaction was complete. The reaction mixture was partitioned between 60 mL 1N NaOH and 120 mL $CH_2Cl_2$, the layers separated and the aqueous phase was washed with three 25 mL portions of $CH_2Cl_2$. The combined organic phase was dried over $MgSO_4$, filtered, and concentrated to an oil. The material was purified by flash chromatography (80 g silica gel, 0-5% 7N $NH_3$ in $CH_3OH/CH_2Cl_2$) to yield the title compound (320 mg, 54%) as a foam: MS (ESI+) for $C_{24}H_{31}N_5O_6$ m/z 470.1 $(M+H)^+$; (ESI−) for $C_{24}H_{31}N_5O_6$ m/z 468.0 $(M-H)^-$; HPLC purity 99% (ret. time, 2.67 min).

Step 5:
1-(4-tert-butylphenyl)-3-(3-hydroxypropyl)urea

A solution of 3-amino-1-propanol (0.180 mL, 2.36 mmol) in diethylether (15 mL) was cooled at 0° C. and treated dropwise with 1-tert-butyl-4-isocyanatobenzene (0.400 mL, 2.25 mmol). The reaction mixture was allowed to slowly warm to room temperature. After 16 h the reaction was found to be complete by TLC (100% ethyl acetate) The reaction mixture was diluted with 10 mL portions of $Cl_2Cl_2$ and $Et_2O$ and washed with 15 mL portions of $H_2O$, 0.5N HCl and brine and dried over $Na_2SO_4$. The organic phase was filtered and concentrated to yield a colorless viscous oil which was dissolved in $PhCH_3$, concentrated and placed under high vac overnight to yield the title compound (600 mg, 110%) as a colorless viscous oil: MS (ESI+) for $C_{14}H_{22}N_2O_2$ m/z 251.0 $(M+H)^+$; (ESI−) for $O_{14}H_{22}N_2O_2$ m/z 249.3 $(M-H)^-$; HPLC purity 98% (ret. time, 3.43 min).

Step 6: 3-(3-(4-(tert-butyl)phenyl)ureido)propyl methanesulfonate

A solution of 1-(4-tert-butylphenyl)-3-(3-hydroxypropyl) urea (563 mg, 2.25 mmol) in methylene chloride (14 mL) was cooled at 0° C. and treated dropwise with triethylamine (0.376 mL, 2.70 mmol) followed by methanesulfonyl chloride (0.191 mL, 2.47 mmol) and the mixture was stirred at 0° C. until complete by TLC. After 30 minutes, the reaction was complete by TLC (100% EA). The reaction mixture was diluted with 15 mL $CH_2Cl_2$ and the organic phase was washed with 15 mL portions of 1N HCl, sat $NaHCO_3$ and $H_2O$ and dried over $MgSO_4$. The solution was filtered and concentrated to a viscous oil that was placed under high vacuum to yield the title compound (800 mg) as a colorless viscous oil that was stored in the freezer: MS (ESI+) for $C_{15}H_{24}N_2O_4S$ m/z 329.1 $(M+H)^+$; HPLC purity 93% (ret. time, 3.95 min).

Step 7: 1-(4-(tert-butyl)phenyl)-3-(3-((((3aR,4R,6R, 6aR)-6-(4-((2,4-dimethoxybenzyl)amino)-7¹'-pyrrolo[2,3-d]pyrimidin-7-yl)-2,2-dimethyltetrahydrofuro[3,4-d][1,3]dioxol-4-yl)methyl)(methyl)amino) propyl)urea A mixture of 3-(3-(4-(tert-butyl)phenyl)ureido)propyl methanesulfonate (224 mg, 0.682 mmol), tetra-n-butylammonium iodide (252 mg, 0.682 mmol) and N,N-diisopropylethylamine (120 µL, 0.67 mmol) was treated with N-(2,4-dimethoxybenzyl)-7-((3aR,4R,6R,6aR)-2,2-dimethyl-6-((methylamino)methyl)tetrahydrofuro[3,4-d][1,3]dioxol-4-yl)-7H-pyrrolo[2,3-d]pyrimidin-4-amine (320 mg, 0.68 mmol) in acetonitrile (7.8 mL, 150 mmol) and the solution was heated at 65° C. After 16.5 h at 65° C., HPLC indicated the reaction was about 78-85% complete. An additional 60 mg of mesylate (in 0.4 mL $CH_3CN$) and 67 mg of TBAI were added and continued heating for 7 h. The reaction mixture was cooled to room temperature and concentrated. The crude residue was purified by flash chromatography (60 g silica gel, 3-7% 7N $NH_3$ in $CH_3OH/CH_2Cl_2$) to yield the product contaminated with TBAI. The material was dissolved in 20 mL 1/1 ethyl acetate/ethyl ether and washed with three 10 mL portions of $H_2O$. The organic phase was dried over $Na_2SO_4$, filtered and concentrated to yield the title compound (295 mg, 62%) as a foam: MS (ESI+) for $C_{38}H_{51}N_7O_6$ m/z 702.2 $(M+H)^+$; (ESI−) for $C_{38}H_{51}N_7O_6$ m/z 700.3 $(M-H)^-$; HPLC purity 96% (ret. time, 3.69 min).

Step 8: 1-(4-(tert-butyl)phenyl)-3-(3-((((2R,3S,4R, 5R)-5-(4-((2,4-dimethoxybenzyl)amino)-7H-pyrrolo [2,3-d]pyrimidin-7-yl)-3,4-dihydroxytetrahydrofuran-2-yl)methyl)(methyl)amino)propyl)urea 1-(4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(methyl)amino)propyl)urea (295 mg, 0.420 mmol) was dissolved in trifluoroacetic acid (11 mL) and water (1 mL) which had been cooled at 0° C. and the resulting solution was stirred at 0° C. for 30 minutes, then warmed to room temperature. After 5 h, the reaction was found to be complete by HPLC. The reaction was concentrated in vacuo and the residue was taken up in 25 mL MeOH (slurry) and concentrated. This process was repeated twice and the residue was placed briefly on high vac. The material was taken up in 15 mL MeOH and the suspension was filtered through a medium frit. The filtrate was concentrated in vacuo, the residue was taken up in 40 mL 20% MeOH/EA and the solution was washed with 25 mL sat $NaHCO_3$. The aqueous layer was back extracted once with 10 mL EA and the combined organics were dried over $Na_2SO_4$. The solution was filtered and concentrated to yield a glass/foam. The product was isolated by preparative TLC (two 20 cm×20 cm×1.0 mm prep TLC plates, 15% 7N $NH_3$ in $CH_3OH/CH_2Cl_2$) to yield the title compound (90 mg, 43%) as a foam: $^1$H NMR (400 MHz, $d_4$-MeOH) ppm 8.08 (s, 1H), 7.26 (m, 3H), 7.21 (m, 2H), 6.63 (d, J=3.52 Hz, 1H), 6.12 (d, J=4.56 Hz, 1H), 4.49 (t, J=4.87 Hz, 1H), 4.21 (m, 1H), 4.17 (t, J=5.60 Hz, 1H), 3.22 (t, J=6.43 Hz, 2H), 2.96 (m, 2H), 2.72 (t, J=6.95 Hz, 2H), 2.46 (s, 3H), 1.76 (m, 2H), 1.28 (s, 9H); MS (ESI+) for $C_{26}H_{37}N_7O_4$ m/z 512.2 $(M+H)^+$; (ESI−) for $C_{26}H_{37}N_7O_4$ m/z 510.2 $(M-H)^-$; HPLC purity 97% (ret. time, 2.81 min).

Step 9: 1-(4-(tert-butyl)phenyl)-3-(3-((((2R,3S,4R, 5R)-5-(4-((2,4-dimethoxybenzyl)amino)-7H-pyrrolo [2,3-d]pyrimidin-7-yl)-3,4-dihydroxytetrahydrofuran-2-yl)methyl)(methyl)amino)propyl)urea hydrochloride A solution of 1-(4-(tert-butyl)phenyl)-3-(3-((((2R,3S,4R, 5R)-5-(4-((2,4-dimethoxybenzyl)amino)-7H-pyrrolo[2,3-d] pyrimidin-7-yl)-3,4-dihydroxytetrahydrofuran-2-yl)methyl) (methyl)amino)propyl)urea (20 mg, 0.039 mmol) in methanol (0.7 mL) was added to a mixture of 0.1N HCl (0.39 mL, 0.039 mmol) and water (2.0 mL). The colorless solution was concentrated in vacuo to remove the methanol. The solution was lyophilized to yield the title compound (20 mg, 93%) as a white solid: $^1$H NMR (400 MHz, $D_2O$) ppm 8.02 (s, 1H), 7.33 (d, 1=3.73 Hz, 1H), 7.21 (d, J=8.09 Hz, 2H), 6.90 (d, J=8.09 Hz, 2H), 6.69 (d, J=3.73 Hz, 1H), 6.13 (d, J=4.56 Hz, 1H), 4.47 (m, 2H), 4.24 (t, J=5.39 Hz, 1H), 3.67 (m, 1H), 3.54 (d, J=12.02 Hz, 1H), 3.33 (m, 1H), 3.22 (m, 1H), 3.11 (m, 1H), 2.94 (s, 3H), 1.90 (m, 2H), 1.20 (s, 9H); MS (ESI+) for $C_{26}H_{37}N_7O_4$ m/z 512.3 $(M+H)^+$; (ESI−) for $C_{26}H_{37}N_7O_4$ m/z 510.2 $(M-H)^-$; HPLC purity 97% (ret. time, 2.82 min). $IC_{50}$<10 nM.

Preparation of Compounds 16 and 17
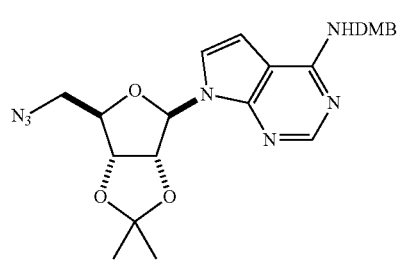
10
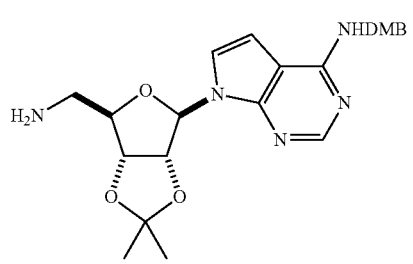
11
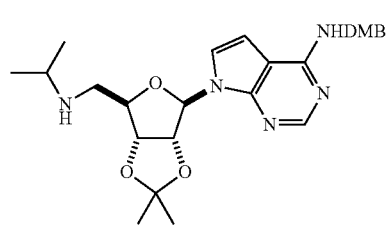
12
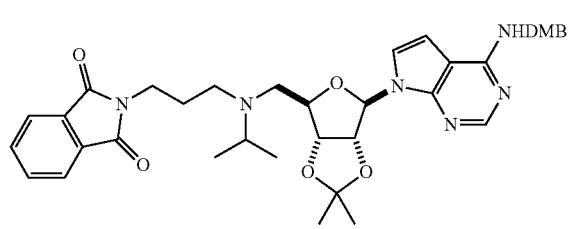
13
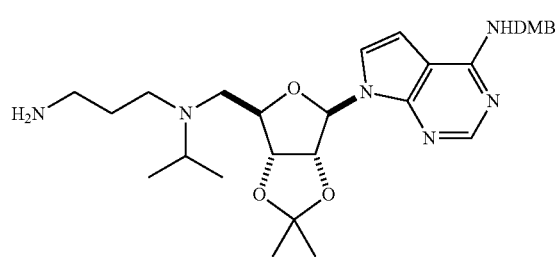
14
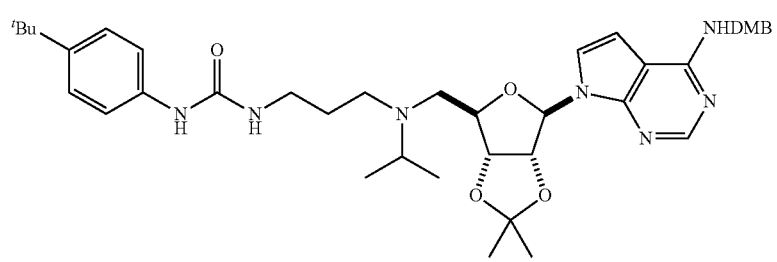
15
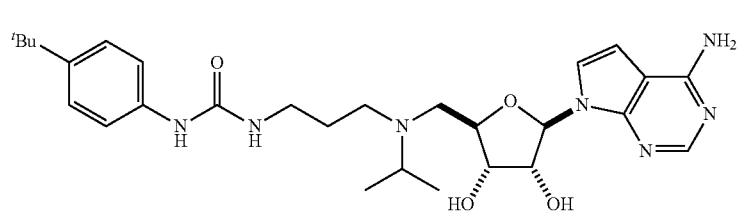
16
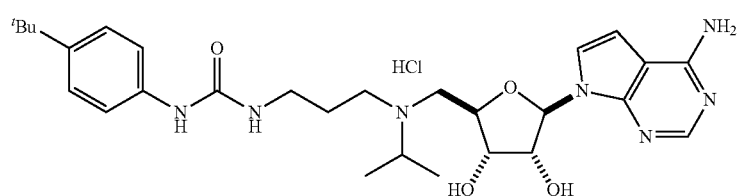
17

Figure 4:
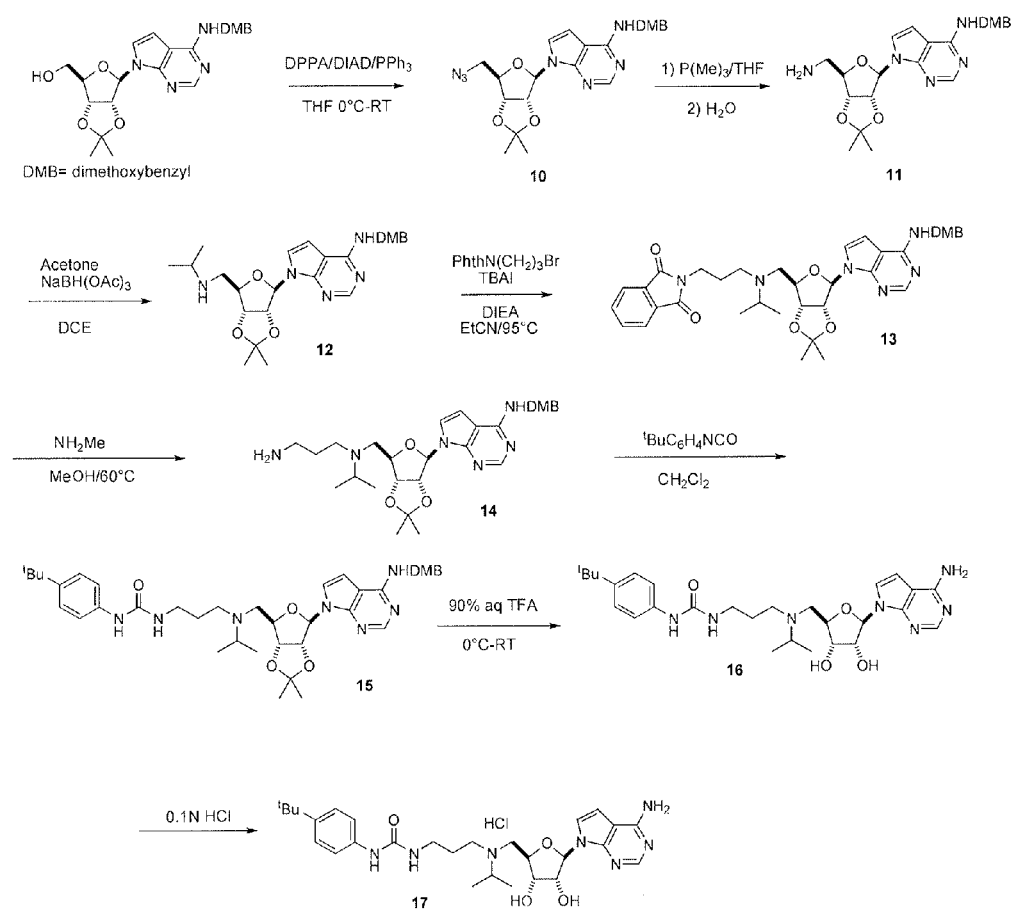
FIG. 4 depicts a route to compound 16 and its hydrochloride salt 17.

The following steps are graphically depicted in FIG. 4.

Step 1: 7-((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine A solution of ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol (2.83 g, 6.20 mmol) and triphenylphosphine (2.28 g, 8.68 mmol) in dry tetrahydrofuran (32 mL) was cooled at 0° C. in an ice/water bath. Diisopropyl azodicarboxylate (1.71 mL, 8.68 mmol) was added dropwise, followed by a solution of diphenylphosphonic azide (1.87 mL, 8.68 mmol) in tetrahydrofuran (5.3 mL, 66 mmol). Upon addition of the DPPA solution, a white milky precipitate formed. After about 30 minutes, the reaction mixture was allowed to warm to room temperature and stir overnight. After 24 h, HPLC indicated that all the starting material had been consumed. The reaction mixture was concentrated to about ½ the original volume and purified by flash chromatography (175 g silica gel, 10-55% EA/hept) to yield the title compound (2.49 g, 83%) as a slightly yellow stiff foam: MS (ESI+) for $C_{23}H_{27}N_7O_5$ m/z 482.2 (M+H)$^+$; (ESI−) for $C_{23}H_{27}N_7O_5$ m/z 480.1 (M+H) m/z 526.1 (M+CO$_2$H)$^-$; HPLC purity 97% (ret. time, 3.64 min).

Step 2: 7-((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine A solution of ((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (2.49 g, 5.17 mmol) in tetrahydrofuran (50 mL, 600 mmol) was treated dropwise with a solution of 1.0 M of trimethylphosphine in tetrahydrofuran (7.24 mL, 7.24 mmol) and the mixture was stirred at room temperature overnight. After 20 h all starting material was consumed by HPLC. The reaction mixture was treated with water (1.80 mL, 99.9 mmol) and stirred at rt for 2 h. The reaction mixture was concentrated, the crude product was taken up in 90 mL CH$_2$Cl$_2$ and washed with four 30 mL portions of H$_2$O and 15 mL brine. The solution was dried over Na$_2$SO$_4$, filtered and concentrated to yield an oil that under the application of a high vacuum became a foam. The crude material was purified by flash chromatography (120 g silica gel, 3-10% 7N NH$_3$ in CH$_3$OH/CH$_2$Cl$_2$) to yield the title compound (136 g, 75%) as a foam: MS (ESI+) for $C_{73}H_{29}N_5O_5$ m/z 456.2 (M+H)$^+$; (ESI−) for $C_{26}H_{35}N_5O_5$ m/z 454.1 (M−H)$^-$; HPLC purity 92% (ret. time, 2.65 min).

Step 3: N-(2,4-dimethoxybenzyl)-7-((3aR,4R,6R,6aR)-6-((isopropylamino)methyl)-2,2-dimethyltetrahydrofuro[3,4-d][1,3]dioxol-4-yl)-7H-pyrrolo[2,3-d]pyrimidin-4-amine A solution of ((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (1.76 g, 3.86 mmol) in 1,2-dichloroethane (34 mL) was treated with acetone (0.31 mL, 42 mmol) and acetic acid (0.22 mL, 3.9 mmol) dropwise followed by sodium triacetoxyborohydride (0.98 g, 4.6 mmol) and the mixture was stirred at room temperature till complete. After 1 h, HPLC indicated the starting material had been consumed and the reaction was complete. The reaction mixture was diluted with 60 mL CH$_2$Cl$_2$ and washed with 50 mL sat NaHCO$_3$. The aqueous phase was washed with 30 mL CH$_2$Cl$_2$ and the combined organic phase was washed with 40 mL brine and dried over Na$_2$SO$_4$. The solution was filtered and concentrated to yield the title compound (1.76 g, 92%) as a glass that was used directly in the next step: MS (ESI+) for $C_{26}H_{35}N_5O_5$ m/z 498.3 (M+H)$^+$; HPLC purity 90% (ret. time, 2.74 min).

Step 4: 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)isoindoline-1,3-dione A mixture of γ-bromopropylphthalimide (2.37 g, 8.85 mmol), tetra-n-butylammonium iodide (0.234 g, 0.632 mmol). N,N-diisopropylethylamine (1.40 mL, 8.04 mmol) and N-(2,4-dimethoxybenzyl)-7-(3aR,4R,6R,6aR)-6-((isopropylamino)methyl)-2,2-dimethyltetrahydrofuro[3,4-d][1,3]dioxol-4-yl)-7H-pyrrolo[2,3-d]pyrimidin-4-amine (3.42 g, 6.32 mmol) was taken up in propanenitrile (25 mL) and was heated at 95° C. After 48 h at 95° C., HPLC indicated that the reaction was nearly complete. The reaction mixture was cooled to room temperature, the mixture was diluted with 200 mL ethyl acetate and washed with two 100 mL portions of H$_2$O and 100 mL brine. The organic phase was dried over Na$_2$SO$_4$, filtered and concentrated to yield a glass. The crude material was purified by flash chromatography (250 g silica gel, 2-4% 7N NH$_3$ in CH$_3$OH/CH$_2$Cl$_2$) to yield the title compound (3.12 g, 72%) as a foam: MS (ESI+) for $C_{37}H_{44}N_6O_7$ m/z 685.2 (M+H)$^+$, (ESI−) for $C_{37}H_{44}N_6O_7$ m/z 729 (M+HCO$_2$)$^-$; HPLC purity 99% (ret. time, 3.17 min).

Step 5: N$^1$-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N$^1$-isopropylpropane-1,3-diamine 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)-propyl)isoindoline-1,3-dione (1.37 g, 2.00 mmol) was dissolved in 2M methylamine in methanol (30 mL, 60 mmol). The solution was stirred at room temperature for 5 minutes then heated at 55-60° C. After 1 h, the SM was consumed by HPLC. The reaction mixture was cooled to room temperature and concentrated in vacuo. The resultant tan oil was taken up in 20 mL MeOH and concentrated. The procedure was repeated to an oil. The material was placed on high vacuum to yield a solid which contained the title compound along with N-methylphthalimide and was used as is in the next step: MS (ESI+) for $C_{29}H_{42}N_6O_5$ m/z 555.4 (M+H)$^+$; HPLC ret. time 2.57 min.

Step 6: 1-(4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)urea A suspension of N$^1$-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N$^1$-isopropylpropane-1,3-diamine (1.11 g, 2.00 mmol, crude from step 6) in methylene chloride (40 mL) was treated dropwise with a solution of 1-tert-butyl-4-isocyanatobenzene (0.36 mL, 2.0 mmol) in methylene chloride (3.5 mL) and allowed to stir at room temperature. After 1 h, reaction was complete by HPLC. The reaction mixture was concentrated to yield a glass. The crude material was purified by flash chromatography (100 g silica gel, 2-4% 7N NH$_3$ in CH$_3$OH/CH$_2$Cl$_2$ to yield the title compound (1.07 g, 73%) as a foam: MS (ESI+) for C$_{40}$H$_{55}$N$_7$O$_6$ m/z 730.4 (M+H)$^+$; (ESI−) for C$_{40}$H$_{55}$N$_7$O$_6$ m/z 728.5 (M−H)$^-$; HPLC purity, 89% (ret. time, 3.78 min).

Step 7: 1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea 1-(4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)urea (1.07 g, 1.39 mmol) was dissolved in a mixture of trifluoroacetic acid (25 mL) and water (2.5 mL) which had been cooled at 0° C. and the resulting solution was stirred at 0° C. for 30 minutes, then warmed to room temperature. After 4 h, the reaction was found to be complete by HPLC. The reaction mixture was concentrated in vacuo and the residue was taken up in 25 mL MeOH (white slurry) and concentrated. This process was repeated three times and the resultant residue was placed under high vacuum. The material was taken up in 100 mL 10% MeOH/CH$_2$Cl$_2$ and washed with two 75 mL portions of sat NaHCO3 and 50 mL 1% aq Na$_2$CO$_3$. The organic phase was dried over Na$_2$SO$_4$, filtered and concentrated to yield a glass/solid. The crude material was purified by flash chromatography (100 g silica gel, 5-10% 7N NH$_3$ in CH$_3$OH/CH$_2$Cl$_2$) to yield the title compound (0.35 g, 46%) as a colorless glass: MS (ESI+) for C$_{28}$H$_{41}$N$_7$O$_4$ m/z 540.3 (M+H)$^+$; (ESI−) for C$_{28}$H$_{41}$N$_7$O$_4$ m/z 538.3 (M−H)$^-$, m/z 584.4 (M+HCO$_2$)$^-$; HPLC purity 98% (ret. time 2.86 min); $^1$H NMR (400 MHz, d$_4$-MeOH) ppm 8.05 (s, 1H), 7.27 (d, J=3.73 Hz, 1H), 7.24 (m, 2H), 7.18 (m, 2H), 6.63 (d, J=3.73 Hz, 1H), 6.15 (d, J=4.77 Hz, 1H), 4.46 (t, J=5.08 Hz, 1H), 4.18 (t, J=5.39 Hz, 1H), 4.11 (m, 1H), 3.22 (m, 2H), 3.07 (m, 1H), 2.85 (m, 1H), 2.72 (m, 1H), 2.60 (t, J=6.43 Hz, 2H), 1.68 (m, 2H), 1.28 (s, 9H), 1.05 (d, J=6.63 Hz, 3H), 1.01 (d, J=6.43 Hz, 3H).

Step 8: 1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea hydrochloride A solution of 1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea (1.64 g, 3.04 mmol) in 50 mL 50% aq methanol was treated with 1.0N of hydrogen chloride in water (3.87 mL, 3.04 mmol). The solution was concentrated to remove most of the methanol and lyophilized overnight. The cloudy mixture was filtered through a fine frit and the filtrate was concentrated in vacuo to remove the MeOH. The resultant solution was lyophilized overnight to yield the title compound (1.70 g, 97%) as a solid: MS (ESI+) for C$_{28}$H$_{41}$N$_7$O$_4$ m/z 540.4 (M+H)$^+$; MS (ESI+) for C$_{28}$H$_{41}$N$_7$O$_4$ m/z 538.4 (M+H)$^+$, m/z 574.4 (M+Cl)$^-$; HPLC purity 97% (ret. time, 2.88 min); $^1$H NMR (400 MHz, d$_4$-MeOH) ppm 8.12 (s, 1H), 7.29 (m, 2H), 7.23 (m, 3H), 6.68 (m, 1H), 6.09 (br. s., 1H), 4.57 (m, 1H), 4.35 (m, 2H), 3.79 (br. s., 1H), 3.55 (m, 2H), 3.26 (br. s., 4H), 1.94 (m, 2H), 1.35 (m, 6H), 1.29 (s, 9H). IC$_{50}$<10 nM.

Preparation of Compound 18

(2R,3R,4S,5R)-2-(4-amino-7H-pyrrolo[2,3-d]pyrimidin-7-yl)-5-(((4-(5-(tert-butyl)-1H-benzo[d]imidazol-2-yl)butyl)(isopropyl)amino)methyl)tetrahydrofuran-3,4-diol (18)

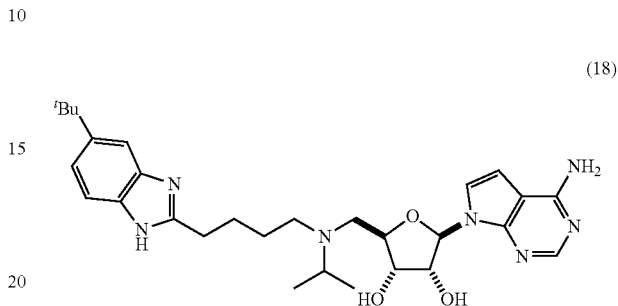

General

HPLC conditions: Agilent 1100 HPLC. Zorbax Eclipse XDB-C18 50×4.6 mm column. Solvent A—Water (0.1% TFA); Solvent B—Acetonitrile (0.07% TFA). Flow rate—1.50 mL/min. Gradient—5 min 95% A to 90% B, 1 min hold, then recycle (to 95% A over 1 min). UV detection @ 214 and 254 nm.

Step 1: Benzyl 5-bromopentanoate

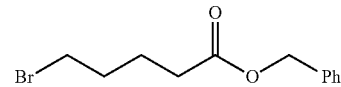 [SMILES: O=C(CCCCBr)OCc1ccccc1]

A solution of 5-bromopentanoic acid (1.00 g, 5.52 mmol) and benzyl alcohol (0.286 mL, 2.76 mmol) in methylene chloride (14 mL) was treated sequentially with N,N'-diisopropylcarbodiimide (0.523 g, 4.14 mmol) and 4-dimethylaminopyridine (43.9 mg, 0.359 mmol). The solution was allowed to stir at room temperature. A precipitate formed within 1 minute of the addition of the 4-dimethylaminopyridine. After ~65 h, the reaction mixture was filtered, the solid was washed with CH$_2$Cl$_2$ and the filtrate was washed with 20 mL portions of 1N HCl, sat NaHCO$_3$ and brine and dried over Na$_2$SO$_4$. The solution was filtered and concentrated to yield a nearly colorless liquid along with a solid (DIC urea). The material was taken up in 1/1 MTBE/heptane to yield a solution with a white precipitate. The mixture was filtered and concentrated and the crude material was purified by flash chromatography (75 g silica gel; 5-10% MTBE/hept) to yield the title compound (0.69 g, 92%) as a colorless liquid. HPLC purity>95° A) (ret. time, 4.73 min).

Step 2: Benzyl 5-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)pentanoate

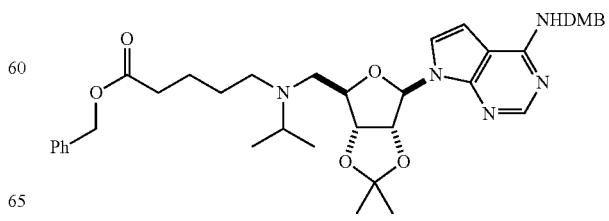

A mixture of benzyl 5-bromopentanoate (116 mg, 0.427 mmol), tetra-n-butylammonium iodide (11.3 mg, 0.0305 mmol), N,N-diisopropylethylamine (69.08 uL, 0.3966 mmol) and N-(2,4-dimethoxybenzyl)-7-(3aR,4R,6R,6aR)-6-((isopropylamino)methyl)-2,2-dimethyltetrahydrofuro[3,4-d][1,3]dioxol-4-yl)-7H-pyrrolo[2,3-d]pyrimidin-4-amine (165 mg, 0.305 mmol) was taken up in propanenitrile (1.0 mL) to give a light tan solution that was heated at 95° C. After 68 h at 95° C., HPLC indicated the starting material had been consumed. The reaction mixture was cooled to room temperature, diluted with 30 mL ethyl acetate and washed with two 25 mL portions of $H_2O$ and 25 mL brine. The organic phase was dried over $Na_2SO_4$, filtered and concentrated to yield a tan viscous glass. The crude material was purified by flash chromatography (40 g silica gel; 1.5% 7N $NH_3$ in $CH_3OH/CHCl_3$) to yield the title compound (151 mg, 72%) as a colorless glass: MS (ESI+) for $C_{38}H_{49}N_5O_7$ m/z 688.3 (M+H)$^+$; MS (ESI−) for $C_{38}H_{49}N_5O_7$ m/z 686.7 (M−H)$^−$; HPLC purity 95% (ret. time, 3.48 min).

Step 3: 5-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)pentanoic acid

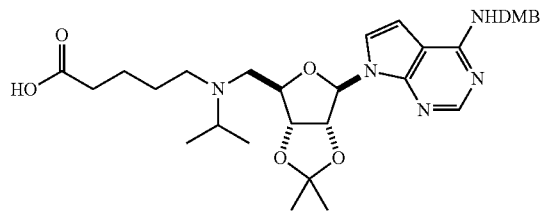

A solution of benzyl 5-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)pentanoate (151 mg, 0.220 mmol) in ethanol (4.1 mL) was treated with 10% palladium on carbon (51 mg, 0.048 mmol) and 1,4-cyclohexadiene (0.23 mL, 2.4 mmol). The mixture was heated at 85° C. until the starting material was consumed as indicated by HPLC. After about 1 h, the starting material was consumed as indicated by HPLC and the reaction mixture was cooled to room temperature. The mixture was filtered through a pad of celite and the pad was washed with 40 mL EtOH. The solution was concentrated to yield the title compound (136 mg, 104%) as a nearly colorless glass, which was taken up in toluene, concentrated and placed under high vac. The material was determined to be of sufficient purity to be used in the next step without purification: MS (ESI+) for $C_{31}H_{43}N_5O_7$ m/z 598.7 (M+H)$^+$; HPLC purity>95% (ret. time, 2.84 min).

Step 4: N-(2-amino-4-(tert-butyl)phenyl)-5-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)pentanamide

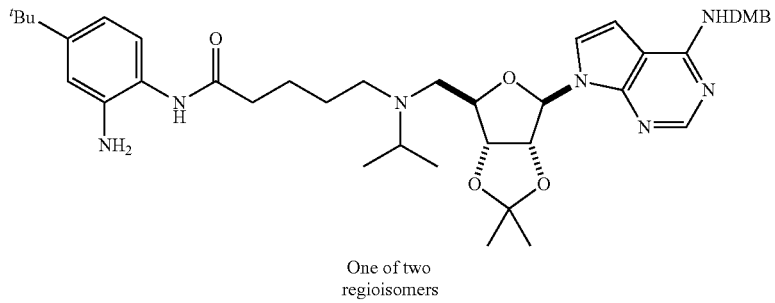

One of two regioisomers

A solution of 5-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)pentanoic acid (131 mg, 0.219 mmol) and 4-tert-butylbenzene-1,2-diamine (40 mg, 0.24 mmol) in N,N-dimethylformamide (2.2 mL) was treated with N,N-diisopropylethylamine (84 uL, 0.48 mmol) dropwise followed by PyBop reagent (120 mg, 0.24 mmol). The solution was allowed to stir at room temperature for 19 h, whereupon HPLC indicated the reaction was complete. The reaction mixture was concentrated under high vacuum. The residue was taken up in 40 mL $CH_2Cl_2$ and washed with 20 mL portions of $H_2O$, 5% citric acid, and brine. The organic phase was dried over $Na_2SO_4$, filtered and concentrated to yield a tan viscous glass. The crude material was purified by flash chromatography (40 g silica gel; 2% 7N $NH_3$ in $CH_3OH/CH_2Cl_2$ to yield the title compound (140 mg, 86%) was a slightly tan glass: MS (ESI+) for $C_{41}H_{57}N_7O_6$ m/z 744.9 (M+H)$^+$; HPLC purity (combined for the two regioisomers) 91% (ret. times, 3.25 and 3.28 min).

Step 5: 7-((3aR,4R,6R,6aR)-6-(((4-(5-(tert-butyl)-1H-benzo[d]imidazol-2-yl)butyl)(isopropyl)amino)methyl)-2,2-dimethyltetrahydrofuro[3,4-d][1,3]dioxol-4-yl)-N-(2,4-dimethoxybenzyl)-7H-pyrrolo[2,3-d]pyrimidin-4-amine

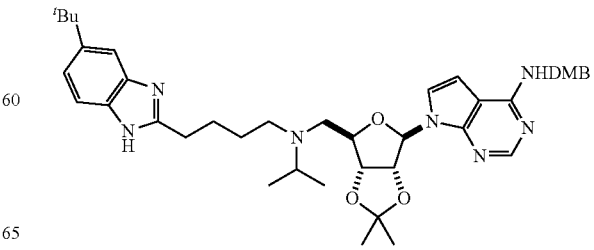

N-(2-amino-4-(tert-butyl)phenyl)-5-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)pentanamide (140 mg, mmol) was taken up in acetic acid (3.5 mL) and the solution was heated at 65° C. for 2 h, whereupon HPLC indicated the starting material had been consumed. The reaction mixture was cooled to room temperature and the solvent was removed under high vac. The residue was taken up in 30 mL $CH_2Cl_2$ and washed with 20 mL portions of sat $NaHCO_3$ and 2% $Na_2CO_3$ solution. The organic phase was dried over $Na_2SO_4$, filtered and concentrated to yield a light tan glass/stiff foam. The crude material was purified by flash chromatography (25 g silica gel; 3% 7N $NH_3$ in $CH_3OH/CH_2Cl_2$) to yield the title compound (120 mg, 88%) as a slightly tan glass: MS (ESI+) for $C_{41}H_{55}N_7O_5$ m/z 726.5 (M+H)$^+$; MS (ESI−) for $C_{41}H_{55}N_7O_5$ m/z 724.6 (M−H)$^-$; HPLC purity 90% (ret. time, 3.14 min).

Step 6: (2R,3R,4S,5R)-2-(4-amino-7H-pyrrolo[2,3-d]pyrimidin-7-yl)-5-((4-(5-(tert-butyl)-1H-benzo[d]imidazol-2-yl)butyl)(isopropyl)amino)methyl)tetrahydrofuran-3,4-diol

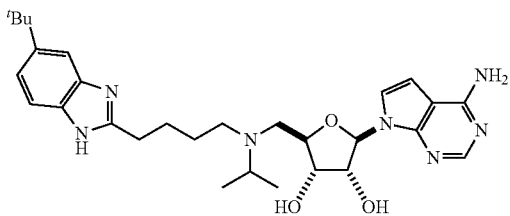

7-((3aR,4R,6R,6aR)-6-(((4-(5-(tert-butyl)-1H-benzo[d]imidazol-2-yl)butyl)(isopropyl)amino)methyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (120 mg, 0.16 mmol) was dissolved in a mixture of trifluoroacetic acid (5.0 mL) and water (0.5 mL) which had been precooled at 0° C. in an ice bath. The solution was stirred at 0° C. for 30 minutes, and then warmed to room temperature. After 4.5 h at room temperature, the reaction was found to be complete by HPLC and the now pink reaction mixture was concentrated. The residue was taken up in 10 mL MeOH and concentrated. This procedure was repeated twice and the residue placed on high vac for 1 h. The material was taken up in 6 mL MeOH and was treated with 100 mg $K_2CO_3$ and five drops of water. The mixture was stirred for 30 minutes during which time the mixture was found to be basic. The mixture was filtered through a fine frit, the solids were washed with 10 mL MeOH and the filtrate was concentrated to yield a nearly colorless solid. The crude material was purified by flash chromatography (20 g silica gel; 8% 7N $NH_3$ in $CH_3OH/CH_2Cl_2$) to yield the title compound (60 mg, 68%) as a colorless glass: MS (ESI+) for $C_{29}H_{41}N_7O_3$ m/z 536.5 (M+H)$^+$; MS (ESI−) for $C_{27}H_{41}N_7O_3$ m/z 534.5 (M−H)$^-$; HPLC purity>95% (ret. time, 2.53 min); $^1$H NMR (400 MHz, d4-MeOH) δ 8.07 (s, 1H), 7.48 (br. s., 1H), 7.38 (d, J=8.50 Hz, 1H), 7.27 (dd, J=8.50, 1.87 Hz, 1H), 7.22 (d, J=3.73 Hz, 1H), 6.61 (d, J=3.73 Hz, 1H), 6.11 (d, J=4.77 Hz, 1H), 4.43 (t, J=5.08 Hz, 1H), 4.14 (t, J=5.49 Hz, 1H), 4.04 (m, 1H), 3.00 (m, 1H), 2.83 (m, 3H), 2.67 (dd, J=14.10, 6.84 Hz, 1H), 2.53 (m, 2H), 1.80 (m, 2H), 1.52 (m, 2H), 1.36 (s, 9H), 1.01 (d, J=6.63 Hz, 3H), 0.97 (d, J=6.63 Hz, 3H).

Figure 7:
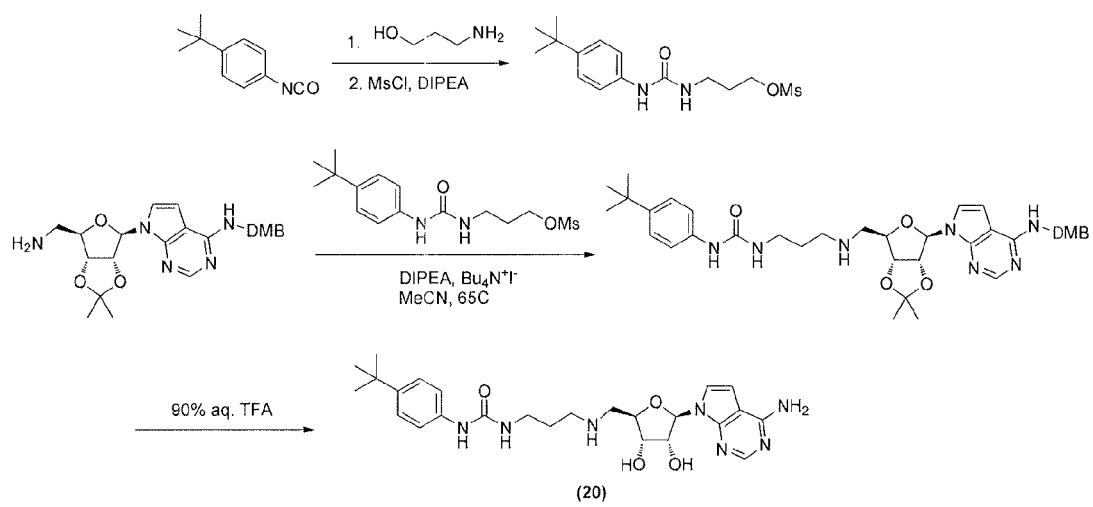
FIG. 7 depicts a route to compound 20.
Figure 8:
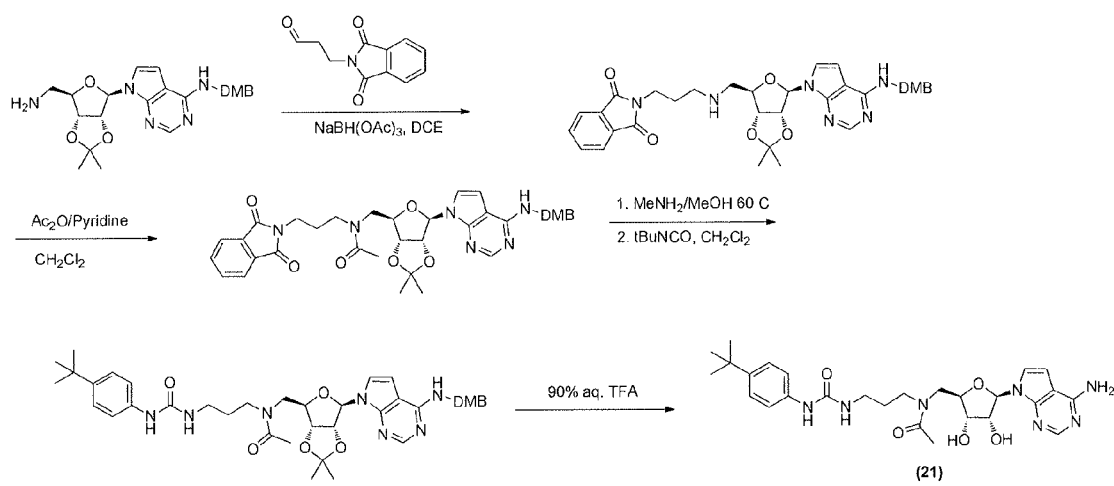
FIG. 8 depicts a route to compound 21.

Compounds 20 and 21 were synthesized by analogous procedures. See FIGS. 7 and 8, respectively.

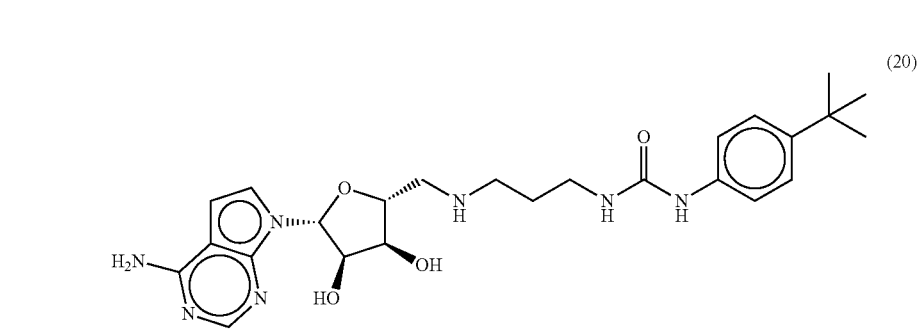

(20)

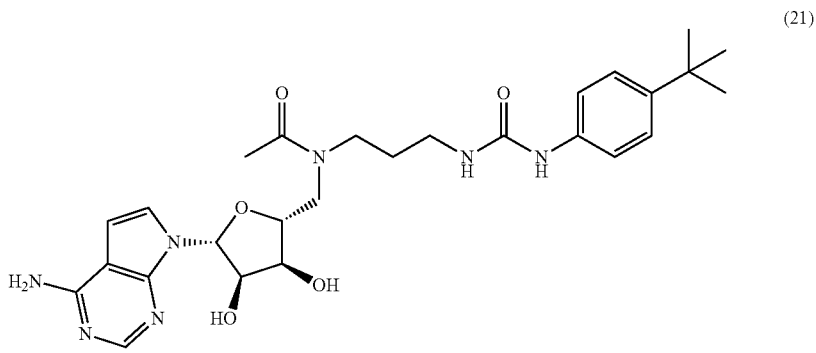

(21)

Inhibition of DOT1L

Compounds 9 and 17 are potent inhibitors of DOT1L in biochemical assays (see Table 1, below). To evaluate the ability of this compound to inhibit DOT1L in cells, its effect on cellular histone H3 lysine 79 (H3K79) methylation was examined. DOT1L is the only known histone methyltransferase capable of methylating H3K79, and so inhibition of cellular DOT1L should lead to a reduction of cellular H3K79 methylation.

TABLE 1

| Compound # | Biochemical $IC_{50}$ (nM) | H3K79 $IC_{50}$ MOLM-13 cells (nM) | Proliferation $IC_{50}$ MOLM-13 cells (μM) |
|---|---|---|---|
| 9 | 6 | 77 | 17.3 |
| 17 | <1 | 59 | 3.2 |
| 18 | <10 | | |
| 20 | <1,000 | | |
| 21 | <1,000 | | |

The data in Table 1 indicates that 9 and 17 can enter cells and inhibit DOT1L in a cellular context. The compound 9 and 17 also inhibited proliferation in the cells.

In summary, inhibition of DOT1L activity with 9 and 17 leads to depletion of H3K79 methylation and a dramatic decrease in growth and viability of MLL-rearranged leukemia cell lines.

Selective Killing of Mixed Lineage Leukemia Cells by Compound 16, A Potent Small-Molecule DOT1L Inhibitor Based on the chemical structures of the SAM substrate and S-adenosylhomocysteine (SAH) product, the reaction mechanism of DOT1L catalysis and the published crystal structure of the DOT1L active site, medicinal chemistry design tenets were established to facilitate mechanism-guided inhibitor discovery; chemical analogues thus designed were synthesized and tested as inhibitors of DOT1L enzymatic activity. From these efforts, compound 16 was identified. This compound demonstrates potent, concentration-dependent inhibition of DOT1L enzyme activity with an 1050 of 400±100 pM. The chemical structure of this compound retains the nucleoside core of the SAM substrate, and SAH product. As such it was designed to bind to the enzyme within the SAM binding pocket. Steady state kinetic analysis confirms that the compound binds to the enzyme competitively with SAM. For example, a distinguishing feature of competitive inhibition is a linear increase in the apparent IC50 of the compound as a function of substrate concentration; compound 16 displays this pattern when assayed as a function of SAM concentration relative to the KM of SAM. SAM is a common methyl group donor that is used by all histone methyltransferases (HMTs). Despite the universality of SAM utilization by HMTs, compound 16 displays remarkable selectivity for inhibition of DOT1L over other HMTs, as summarized in FIG. 5. Thus, the compound displays a minimum selectivity of >1000-fold for DOT1L relative to all HMTs that have been tested.

Compound 16 Selectively Inhibits Cellular H3K79 Methylation

Having established that compound 16 is a potent and highly selective DOT1L inhibitor in biochemical assays, we next tested the ability of compound 16 to inhibit DOT1L in cells by immunoblot analysis of extracted histones using an antibody specific for dimethylated H3K79 (H3K79me2). Treatment of human cell lines derived from MLL-rearranged acute myeloid leukemia (AML) (MOLM-13, MLL-AF9), MLL-rearranged biphenotypic leukemia (MV4-11, MLL-AF4), or non-MLL-rearranged T-cell acute leukemia (Jurkat) with compound 16 led to a concentration dependent reduction in global H3K79me2 levels. To understand the kinetics of compound 16-mediated cellular H3K79me2 depletion, we performed a time course analysis in MV4-11 cells incubated with 3 μM compound 16, a concentration sufficient for maximal cellular DOT1L inhibition. A modest reduction in H3K79me2 levels was apparent within one day of treatment, but full depletion took four to five days. There is no known histone demethylase enzyme specific for H3K79, so the decline in methylation at this residue following DOT1L inhibition is presumably due to incorporation into chromatin of unmethylated H3 through histone turnover and replacement.

To assess the specificity of compound 16 inhibitory activity in cells, we immunoblotted histones extracted from compound 16-treated MV4-11 cells with a panel of methyl-lysine and methyl-arginine residue specific antibodies. The only methyl marks affected by compound 16 treatment were H3K79me1 and H3K79me2, consistent with compound 16 being a highly specific DOT1L inhibitor in a cellular context.

Compound 16 Blocks MLL Fusion Target Gene Expression

We next tested whether compound 16 was able to inhibit expression of key MLL fusion target genes. HOXA9 and MEIS1 over expression is a hallmark of MLL, rearranged leukemias (Armstrong et al., 2002; Ferrando et al., 2003; Ross et al., 2004; Ross et al., 2003; Rozovskaia et al., 2001; Yeoh et al., 2002). Furthermore, both genes are bound by MLL fusion proteins, hypermethylated at H3K79 and down-regulated by DOT1L RNAi knockdown in MLL-rearranged cell lines, including MV4-11 (Guenther et al., 2008; Krivtsov et al., 2008; Lin et al., 2010; Milne et al., 2005; Monroe et al., 2010; Mueller et al., 2009; Okada et al., 2005; Thiel et al.; Yokoyama et al., 2010). We used quantitative real-time PCR (RT-PCR) to examine the effect of compound 16 on HOXA9 and MEIS1 transcript levels in MOLM-13 and MV4-11 cells. Treatment with compound 16 led to a concentration-dependent decrease of both transcripts in each cell line with IC50s of approximately 700 nM. We evaluated the kinetics of this decrease by measuring HOXA9 and MEIS1 mRNA levels over time in cells treated with 3 μM compound 16. Levels of both transcripts were significantly decreased within 48 hours of compound addition, and were maximally reduced after six to eight days of compound 16 treatment (fitting of these data yielded estimated half-lives of 2.3 and 3.3 days for HOXA9 and MEIS1 inhibition, respectively). This decrease was not due to a general inhibitory effect on gene expression since transcript levels of the housekeeping gene TBP were unaffected.

Compound 16 Selectively Inhibits Proliferation of MLL-Rearranged Cells

Having established that compound 16 can inhibit H3K79 methylation and block MLL fusion target gene expression, we investigated whether this translated into anti-proliferative activity in MLL-rearranged leukemic cells. We performed proliferation assays over several days with MV4-11 and MOLM-13 cells in the presence or absence of 3 μM compound 16. Jurkat cells were included as a non-MLL rearranged cell line control. The effect of extended compound 16 treatment was remarkably specific for the MLL-rearranged cell lines. The number of viable MV4-11 and MOLM-13 cells was dramatically reduced by compound 16, whereas the growth of Jurkat cells was unaffected. The lack of effect on Jurkat cells was not due to differences in the ability of compound 16 to inhibit DOT1L in these cells as measured by immunoblot for cellular H3K79me2 levels. This analysis also revealed a significant delay before the antiproliferative effects of compound 16 became apparent; both MLL-rearranged cell lines continued to proliferate at a normal rate for several days after exposure to the inhibitor. This may reflect the time required to reverse fully the aberrant expression of MLL fusion target genes following DOT1L inhibition, a process that presumably involves depletion of methylated H3K79, followed by decreased mRNA expression and reduced levels of gene products critical for leukemogenic growth. To expand our analysis of the differential sensitivity of MLL-rearranged cell lines to compound 16, we determined IC50 values for inhibition of proliferation in a panel of six MLL-rearranged and six non-rearranged human leukemia cell lines. The MLL rearranged panel (FIG. 6) included human cell lines derived from ALL, AML and biphenotypic leukemias harboring MLL-AF4, MLL-AF9 or MLL-ENL fusions. As shown in FIG. 6, IC50 values for MLL-rearranged cell lines were in the nanomolar to low micromolar range, whereas IC50s for non-MLL rearranged cell lines were always above 10 µM or undetermined due to lack of inhibition at the highest concentration tested (reported as IC50>50 µM in FIG. 6). We next determined whether these results would extend to primary murine hematopoietic progenitors transformed by retroviral expression of an MLL-AF9 fusion protein.

These results demonstrate that DOT1L methyltransferase activity is required for proliferation of MLL-rearranged cells and MLL fusion mediated transformation, but is not essential for proliferation and viability of non-MLL-rearranged cells in culture.

Compound 16 Causes Differentiation and Apoptosis in MLL-Rearranged Cells

To explore the mechanism of cell killing in more detail, we determined effects of compound 16 on the cell cycle and apoptosis in MV4-11 and MOLM-13 cells by flow cytometry for DNA content and Annexin V staining. In MV4-11 cells, a modest increase in G0/G1 phase, and a decrease in S-phase cells were apparent after four days of incubation with 3 µM compound 16. This was followed by an increase in sub-G1 and Annexin-positive cells over the next six days, consistent with apoptotic cell death. Similar results were obtained in MOLM-13 cells, although the percentage of Annexin-positive cells was significantly lower. We next analyzed whether compound 16 induced differentiation prior to cell death. MOLM-13 cells were treated with 3 µM compound 16 and monitored for cell surface expression of the myeloid differentiation marker CD14 by flow cytometry. Expression of CD14 was induced following 12 days of compound 16 treatment. Gene set enrichment analysis (GSEA) (Subramanian et al., 2005) of genes upregulated by compound 16 treatment of MOLM-13 cells (see below) also demonstrated significant enrichment for hematopoietic cell lineage markers, including CD14, (Normalized Enrichment Score (NES)=1.78, False Discovery Rate (FDR)=0.054). This provides further evidence that small-molecule inhibition of DOT1L promotes some degree of differentiation prior to cell killing.

Compound 16 Reverses the MLL-rearranged Gene Signature

To determine effects of compound 16 treatment on gene expression in MLL rearranged leukemia cell lines, RNA was isolated from MV4-11 cells and MOLM-13 cells treated with 3 µM compound 16 for up to six days, amplified and hybridized to Affymetrix microarrays. Statistically significant changes in gene expression (probes with statistically significant changes (q<0.15) and up or down-regulated at least 2-fold) were not observed until four days after inhibitor treatment, consistent with the relatively delayed effects of compound 16 on H3K79 methylation and proliferation. Among the genes down-regulated in MV4-11 and MOLM-13 cells following 6 days of compound 16 treatment are several that have been previously implicated in MLL fusion mediated leukemogenesis including multiple HOXA genes, MEIS1 and MEF2C. GSEA of genes down-regulated following 6 day compound 16 treatment of MOLM-13 cells demonstrated strong enrichment (NES=−1.74, FDR=0.014) for genes over expressed in MLL-rearranged human acute leukemias as compared to MLL-germline acute leukemias (Ross et al., 2004). This indicates that small-molecule inhibition of DOT1L is able to reverse the MLL-rearranged gene expression signature in MLL-rearranged cell lines. We next used GSEA to compare genes downregulated following 6 day compound 16 treatment of MOLM-13 (MLL-AF9) or MV4-11 (MLL-AF4) cells with genes identified as direct targets of MLL-AF9, or MLLAF4 (Guenther et al., 2008) through genome-wide chromatin immunoprecipitation coupled with large scale sequencing (ChIP-seq). Genes down-regulated by compound 16 in MOLM-13 cells were significantly enriched for direct MLL-AF9 targets (NES=−1.86, FDR: 0.007), whereas genes down-regulated by compound 16 in MV4-11 cells were enriched for direct MLL-AF4 targets (NES=−1.51, FDR: 0.081, FIG. 5D). Both results indicate that small-molecule inhibition of DOT1L decreases the expression of direct MLL fusion targets. Finally, we compared gene expression changes caused by compound 16 treatment of MOLM-13 (MLL-AF9) cells with those caused by genetic knockout of Dot1L in a mouse model of MLL-AF9 leukemia. We found significant overlap between these gene expression changes (NES=−1.58, FDR: 0.024, FIG. 5E) indicating that compound 16 treatment and genetic ablation of Dot1L cause cell killing of MLL-rearranged cells through similar pathways.

INCORPORATION BY REFERENCE

All of the U.S. patents and U.S. published patent applications cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:
1. A compound selected from

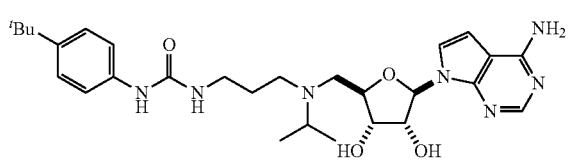

and pharmaceutically acceptable salts, hydrates, enantiomers and stereoisomers thereof.

2. A compound

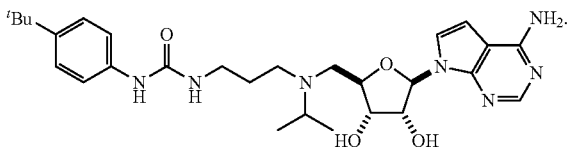

3. A pharmaceutically acceptable salt of

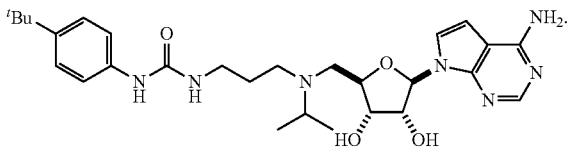

4. The pharmaceutically acceptable salt of claim 3, being

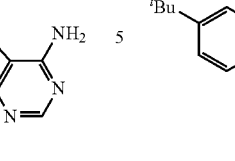

5. A pharmaceutical composition comprising a compound of claim 1 and a pharmaceutically acceptable diluent or carrier.

6. A pharmaceutical composition comprising a compound of claim 2 and a pharmaceutically acceptable diluent or carrier.

7. A pharmaceutical composition comprising a pharmaceutically acceptable salt of claim 3 and a pharmaceutically acceptable diluent or carrier.

8. A pharmaceutical composition comprising a pharmaceutically acceptable salt of claim 4 and a pharmaceutically acceptable diluent or carrier.

9. A kit comprising a compound of claim 1 and instructions for use thereof.

10. A kit comprising a compound of claim 2 and instructions for use thereof.

11. A kit comprising a pharmaceutically acceptable salt of claim 3 and instructions for use thereof.

12. A kit comprising a pharmaceutically acceptable salt of claim 4 and instructions for use thereof.

* * * * *